US010125358B2

(12) United States Patent
Francklyn et al.

(10) Patent No.: US 10,125,358 B2
(45) Date of Patent: Nov. 13, 2018

(54) METHODS AND COMPOUNDS FOR INCREASING THREONYL-TRNA SYNTHETASE ACTIVITY

(71) Applicant: UNIVERSITY OF VERMONT AND STATE AGRICULTURAL COLLEGE, Burlington, VT (US)

(72) Inventors: Christopher Francklyn, Burlington, VT (US); Karen M. Lounsbury, Essex Junction, VT (US); Jason Botten, Williston, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 467 days.

(21) Appl. No.: 14/416,365

(22) PCT Filed: Jul. 24, 2013

(86) PCT No.: PCT/US2013/051807
§ 371 (c)(1),
(2) Date: Jan. 22, 2015

(87) PCT Pub. No.: WO2014/018619
PCT Pub. Date: Jan. 30, 2014

(65) Prior Publication Data
US 2015/0166976 A1    Jun. 18, 2015

Related U.S. Application Data

(60) Provisional application No. 61/675,669, filed on Jul. 25, 2012.

(51) Int. Cl.
| | | |
|---|---|---|
| *A61K 38/43* | (2006.01) | |
| *A61K 45/06* | (2006.01) | |
| *C12N 9/00* | (2006.01) | |
| *A61K 38/53* | (2006.01) | |
| *G01N 33/50* | (2006.01) | |
| *A61K 48/00* | (2006.01) | |

(52) U.S. Cl.
CPC .............. *C12N 9/93* (2013.01); *A61K 38/43* (2013.01); *A61K 38/53* (2013.01); *A61K 45/06* (2013.01); *G01N 33/5064* (2013.01); *A61K 48/00* (2013.01); *C12Y 601/01003* (2013.01); *G01N 2333/82* (2013.01); *G01N 2333/9015* (2013.01); *G01N 2500/02* (2013.01)

(58) Field of Classification Search
CPC ...... A61K 38/43; A61K 38/53; C12Y 601/01; C12Y 601/01003
See application file for complete search history.

(56) References Cited

U.S. PATENT DOCUMENTS

| 5,795,757 A | 8/1998 | Hodgson et al. |
| 2012/0058133 A1 | 3/2012 | Whitman et al. |
| 2013/0129704 A1 | 5/2013 | Greene et al. |
| 2015/0177243 A1 | 6/2015 | Francklyn et al. |
| 2015/0210997 A1 | 12/2015 | Francklyn et al. |

FOREIGN PATENT DOCUMENTS

| EP | 1576160 B1 | 5/2007 |
| WO | 2011097031 A2 | 8/2011 |
| WO | 2011139801 A3 | 11/2011 |

OTHER PUBLICATIONS

Even-Zohar, N. et al., "Nutrition-induced catch-up growth increases hypoxia inducible factor 1 α RNA levels in the growth plate", Bone, 2008, vol. 42, pp. 505-515.
Greenberg, Y. et al., "The novel fragment of tyrosyl tRNA synthetase, mini-TyrRS, is secreted to induce an angiogenic response in endothelial cells", The FASEB Journal, May 2008, vol. 22, pp. 1597-1605.
Howard, O.M. Z. et al., "Histidyl-tRNA Synthetase and Asparaginyl-tRNA Synthetase, Autoantigens in Myositis, Activate Chemokine Receptors on T Lymphocytes and Immature Dendritic Cells", The Journal of Experimental Medicine, Sep. 16, 2002, vol. 196, pp. 781-791.
Kawamura, T. et al., "Anti-angiogenesis Effects of Borrelidin are Mediated through Distinct Pathways: Threonyl-tRNA Synthetase and Caspases are Independently Involved in Suppression of Proliferation and Induction of Apoptosis in Endothelial Cells", The Journal of Antibiotics, Aug. 2003, vol. 56, pp. 709-715.
NCBI, GenBank accession No. NM-152295.4, Jun. 27, 2012.
Olano,C. et al., "Biosynthesis of the Angiogenesis Inhibitor Borrelidin by Streptomyces parvulus Tü4055: Cluster Analysis and Assignment of Functions", Chemistry & Biology, Jan. 2004, vol. 11, pp. 87-97.
Park, S. et al., "Aminoacyl tRNA systhetases and their connections to disease", PNAS, Aug. 12, 2008, vol. 105, pp. 11043-11049.
Ruan, B. et al., "A Unique Hydrophobic Cluster Near the Active Site Contributes to Differences in Borrelidin Inhibition among Threonyl-tRNA Sythetases", The Journal of Biological Chemistry, Jan. 7, 2005, vol. 280, pp. 571-577.
Williams, T. et al., "Secreted Threonyl-tRNA synthetase stimulates endothelial cell migration and angiogenesis", Scientific Reports, Feb. 21, 2013, vol. 3:1317, pp. 1-7.
International Search Report and the Written Opinion of the International Searching Authority dated Oct. 10, 2013 for International Patent Application No. PCT/US2013/051806, 15 pages.

(Continued)

*Primary Examiner* — Kagnew H Gebreyesus
(74) *Attorney, Agent, or Firm* — Pierce Atwood LLP

(57) ABSTRACT

The invention includes, in part, methods and compounds for treating diseases and conditions characterized by reduced threonyl-tRNA synthetase (TARS) activity, which include, but are not limited to diseases and conditions in which angiogenesis is reduced as compared to normal. In some embodiments of the invention, a level of a TARS molecule is determined and compared to a control level of TARS to assess a treatment for a disease or condition characterized by reduced TARS activity.

17 Claims, 18 Drawing Sheets

Specification includes a Sequence Listing.

(56) References Cited

OTHER PUBLICATIONS

International Preliminary Report on Patentability dated Jan. 27, 2015 for the International Patent Application No. PCT/US2013/051806, 5 pages.
International Search Report and the Written Opinion of the International Searching Authority dated Oct. 24, 2013 for International Patent Application No. PCT/US2013/051808, 17 pages.
International Preliminary Report on Patentability dated Feb. 5, 2015 for the International Patent Application No. PCT/US2013/051808, 10 pages.
International Search Report and the Written Opinion of the International Searching Authority dated Oct. 22, 2013 for International Patent Application No. PCT/US2013/051807, 15 pages.
International Preliminary Report on Patentability dated Feb. 5, 2015 for the International Patent Application No. PCT/US2013/051807, 12 pages.
Ahmed, S. A., et al., "A new rapid and simple non-radioactive assay to monitor and determine the proliferation of lymphocytes: an alternative to [3H]thymidine incorporation assay." J Immunol Methods, 1994, vol. 170, pp. 211-224.
Altundag, K., et al.,"CA125 Nadir values as a prognostic factor in epithelial ovarian cancer." J Clin Oncol, 2005, vol. 23, pp. 2435-2436.
Arnaoutova, I. and H. K. Kleinman, "In vitro angiogenesis: endothelial cell tube formation on gelled basement membrane extract." Nat Protoc, 2010, vol. 5, pp. 628-635.
Cassavaugh, J. M., et al., "Negative regulation of HIF-1alpha by an FBW7-mediated degradation pathway during hypoxia." J Cell Biochem, 2011, vol. 112, pp. 3882-3890.
Ewing, R. M., et al., "Large-scale mapping of human protein-protein interactions by mass spectrometry." Mol Syst Biol, 2007, vol. 3, p. 89.
Francklyn, C. S., et al., "Methods for kinetic and thermodynamic analysis of aminoacyl-tRNA synthetases." Methods, 2008, vol. 44, pp. 100-118.
Longair, M. H., et al., "Simple Neurite Tracer: open source software for reconstruction, visualization and analysis of neuronal processes." Bioinformatics, 2011, vol. 27, pp. 2453-2454.
Lounsbury, K. M., et al., "A family of proteins that stabilize the Ran/TC4 GTPase in its GTP-bound conformation." J Biol Chem, 1994, vol. 269, pp. 11285-11290.
Mor, G., et al., "Serum protein markers for early detection of ovarian cancer." Proc Natl Acad Sci U S A, 2005, vol. 102, pp. 7677-7682.
Ribatti, D., et al., "The gelatin sponge-chorioallantoic membrane assay." Nat Protoc, 2006, vol. 1, pp. 85-91.
Strausberg, R. L., "The Cancer Genome Anatomy Project: new resources for reading the molecular signatures of cancer." J Pathol, 2001, vol. 195, pp. 31-40.
Svensson, K. J., et al., "Hypoxia triggers a proangiogenic pathway involving cancer cell microvesicles and PAR-2-mediated heparin-binding EGF signaling in endothelial cells." Proc Natl Acad Sci U S A, 2011, vol. 108, pp. 13147-13152.
Tomlins, S. A., et al., "Integrative molecular concept modeling of prostate cancer progression." Nat Genet, 2007, vol. 39, pp. 41-51.
Uhlen, M., et al., "Towards a knowledge-based Human Protein Atlas." Nat Biotechnol, 2010, vol. 28, pp. 1248-1250.
Wakasugi, K. and P. Sshimmel, "Two distinct cytokines released from a human aminoacyl-tRNA synthetase." Science, 1999, vol. 284, pp. 147-151.
Wilkinson, B., et al., "Separation of anti-angiogenic and cytotoxic activities of borrelidin by modification at the C17 side chain." Bioorg Med Chem Lett, 2006, vol. 16, pp. 5814-5817.
Wong, C., et al., "VEGF and HIF-1alpha expression are increased in advanced stages of epithelial ovarian cancer." Gynecol Oncol, 2003, vol. 91, pp. 513-517.
Bikfalvi, A. and Bicknell, R., "Recent advances in angiogenesis, anti-angiogenesis and vascular targeting", Trends in Pharmacological Sciences, Dec. 2002, vol. 23, pp. 576-582.
Bonfils, G.M. et al., "Leucyl-tRNA synthetase controls TORC1 via the EGO complex", Molecular Cell, 2012, vol. 46, pp. 105-110.
Brown, M.V. et al., "Mammalian aminoacyl-tRNA synthetases: cell signaling functions of the protein translation machinery", Vascul Pharmacol, 2010, vol. 52, pp. 21-26.
Chang, H., et al., "Agonist and antagonist effects of diadenosine tetraphosphate, a platelet dense granule constituent, on platelet P2Y1, P2Y12 and P2X1 receptors", Thromb Res, 2010, vol. 125, pp. 159-165.
Conant, JL. et al., "Sarcomatiod renal cell carcinoma is an examples fo epithelial-mesenchymal transition", J. Clin. Pat., 2011, vol. 64, pp. 1088-1092.
Delicado, E.G. et al., "Dinucleoside polyphosphates and their interaction with other nucleotide signaling pathways", Pfluger Arch, 2006, vol. 452, pp. 563-572.
Dieterich, D.C. et al., "Labeling, detection and identification of newly synthesized proteomes with bioorthogonal non-canonical amino-acid tagging", Nat Protoc, 2007, vol. 2, pp. 532-540.
Folkman, J., "Angiogenesis-dependent diseases", Semin Oncol, Dec. 2001, vol. 28, pp. 536-452.
Guo, R.T. et al., "Crystal structures and biochemical analyses suggest a unique mechanism and role for human glycyl-tRNA synthetase in Ap4A homeostasis" J Biol Chem, 2009, vol. 284, pp. 28968-28976.
Han, J.M. et al., "Leucyl-tRNA synthetase is an intracellular leucine sensor for the mTORC1-signaling pathway", Cell, 2012, vol. 149, pp. 410.-424.
Lee, Y.N. et al., "The function of lysyl-tRNA synthetase and Ap4A as signaling regulators of MITF activity in FcepsilonRI-activated mast cells", Immunity, 2004, vol. 20, pp. 145-151.
Liao, D and Johnson, Rs., "Hypoxia a key regulator of angiogenesis in cancer", Cancer and Metastasis Reviews, 2007, vol. 26, pp. 281-290.
McLennan, A.G. "Dinucleoside ployphosphates—friend or foe?" Pharmacol Ther, 2000, vol. 87, pp. 73-89.
Ofir-Birin, Y. et al., "Structural Switch of Lysyl-tRNA Synthetase between Translation and Transcription", Mol Cell, 2013, vol. 49, pp. 30-42.
Olsson, A.K. et al., "VEGF receptor signalling—in control of vascular function", Nat Rev Mol Cell Biol, 2006, vol. 7, pp. 359-371.
Roedersheimer, M. et al., "Complementary effects of extracellular nucleotides and platelet-derived extracts on angiogenesis of vasa vasorum endothelial cells in vitro and subcutaneous Matrigel plugs in vivo", Vasc Cell, 2011, vol. 3, p. 4.
Mehta, R. et al "Proteosomal Regulation of the Hypoxic Response modulates aging in C. elegans" Science, May 2009, vol. 324, pp. 1196-1198.
Eastwood, EL. and SE. Schaus, "Borrelidin induces the transcription of amino acid biosynthetic enzymes via a GCN4-dependent pathway", Bioorg. Med. Chem. Lett., Jul. 2003, vol. 13, pp. 2235-2237.
Funahashi, Y. et al., "Establishment of a quantitative mouse dorsal air sac model and its application to evaluate a new angiogenesis inhibitor", Oncol. Res., 1999, vol. 11, pp. 319-329.
Moss, S.J. et al., "Biosynthesis of the angiogenesis inhibitor borrelidin:directed biosynthesis of novel analogues", Chem. Communications, Jun. 14, 2006, vol. 22, pp. 2341-2343.
Tsuchiya, E. et al., "Borrelidin inhibits a Cyclin-dependent kinase (CDK), Cdc28/Cln2 of *Saccharomyces cerevisiae*", J. of Antibiotics, Jan. 2011, vol. 54. pp. 84-90.
Wakabayashi, T. et al., "Borrelidin is an angiogenesis inhibitor; disruption of angiogenic capillary vessels in rat aorta matrix culture model" J. antibiotics, Aug. 1997, vol. 50, pp. 671-676.
Gantt, J.S. et al., "Increased levels of threonyl-tRNA synthetase in a borrelidin resistant Chinese hamster ovary cell line" PNAS, Sep. 1981, vol. 78, pp. 5367-5370.
Herzog, W. et al., "Genetic evidence for a non-canonical function of seryl-tRNA synthetase in vascular development", Circulation Research, Jun. 5, 2009, vol. 104, pp. 1260-1266.
Kontis, K. and S. Arfin, "Isolation of a cDNA clone for human threonyl-tRNA synthetase: amplification of the structural gene in

(56) References Cited

OTHER PUBLICATIONS borrelidin-resistant cell lines", Molecular and Cellular Biology, May 1989, vol. 9, pp. 1832-1838.

Nass, G. and K. Poralla, "Genetics of borrelidin resistant mutants of *Saccharomyces cerivisiae* and properties of their threonyl-tRNA-synthetase", Mol. Gen. Genet., Aug. 1976, vol. 10, pp. 39-43.

Seibold, M. et al., "Homoserine and threonine pools of borrelidin resistant *Saccharomyces cerivisiae* mutants with an altered aspartokinase", Arch Microbiol., Jul. 1981, vol. 129, pp. 368-370.

Habibi, D. et al., "Borrelidin, a small molecule nitrile-containing macrolide inhibitor of threonyl-tRNA synthetase, is a potent inducer of apoptosis in acute lymphoblastic leukemia", Springer, Jun. 17, 2011, pp. 1-10.

Nagamitsu, T. et al., "Total Synthesis of Borrelidin", J. Org. Chem., 2007, vol. 72, pp. 2744-2756.

Vong, B.G. et al., "Stereoselective Total Syntheis of (−)-Borrelidin", Angew. Chem. Int. Ed., 2004, vol. 43, pp. 3947-3951.

Woolard, J. et al., "Borrelidin modulates the alternative splicing of VEGF in favour of anti-angiogenic isoforms", Chemical Science, 2011, vol. 2, pp. 273-278.

Chandran, U.R. et al., "Gene expression profiles of prostate cancer reveal involvement of multiple molecular pathways in the metastatic process", BMC Cancer, Apr. 12, 2007, vol. 7, pp. 1-21.

Fox, P.L. et al., "Noncanonical Functions of Aminoacyl-tRNA Synthetases in Translational Control", Translational Control in Biology and Medicine, 2007, vol. 29, pp. 829-854.

Ghanipour, A. et al., "The Prognostic Significance of Tryptophanyl-tRNA Synthetase in Colorectal Cancer", Cancer Epidemiol Biomarkers, Nov. 2009, vol. 18, pp. 2949-2956.

Harisi, R. et al., "Differential Inhibition of Single and Cluster Type Tumor Cell Migration", AntiCancer Research, 2009, vol. 29, pages.

Kim, S. et al., "Aminoacyl-tRNA synthetases and tumorigenesis: more than housekeeping", Nature, Oct. 2011, vol. 11, pp. 708-719.

Mathews, M.B. et al., "Anti-Threonyl-tRNA Synthetase, a Second Myositis-Related Autoantibody", J. ExP. Med, Aug. 1984, vol. 160, pp. 420-434, Downloaded from jem.rupress.org on Jan. 29, 2013.

Simirnova, E.V. et al., "Noncanonical Functions of Amino-acyltRNA Synthetases", Biochemisty (Moscow), 2012, vol. 77, pp. 15-25.

Vazquez-Mena, O. et al., "Amplified Genes May Be Overexpressed, Unchanged, or Downregulated in Cervical Cancer Cell Lines", PLoS ONE, Mar. 2012, vol. 7, pp. 1-17.

Vellaichamy, A. et al., "Proteomic Interrogation of Androgen Action in Prostate Cancer Cells Reveals Roles of Aminoacyl tRNA Synthetases", PLos ONE, Sep. 2009, vol. 4, pp. 1-12.

Zampieri, S. et al., "Polymyositis, dermatomyositis and malignancy: A further intriguing link", Autoimmunity Reviews, 2010, vol. 9, pp. 449-453.

Guo, M. et al., "New functions of aminoacyl-tRNA synthetases beyond translation", Nature Reviews, Sep. 2010, vol. 11, pp. 668-674.

Ko, Y.G. et al., "Glutamine-dependent Antiapoptotic Interaction of Human Glutaminyl-tRNA Synthetase with Apoptosis Signal-regulating Kinase 1*", The Journal of Biological Chemistry, Feb. 2001, vol. 276, pp. 6030-6036.

Selected Interaction from affinity purified TARS identified by mass spectrometry

| Prey Gene Names | XC Score | # Peptides ID'd | Condition | Gene Function |
|---|---|---|---|---|
| TARSL2 | 38.28 | 4 | 1,2 | Threonyl-tRNA Synthetase (second cytoplasmic paralog) |
| EPRS | 30.19 | 4 | 1 | Bifunctional GluProRS |
| PARP | 30.16 | 4 | 2 | Poly [ADP ribose] polymerase |
| eEF1A1 | 10.16 | 2 | 1,2 | Elongation factor 1-alpha 1 |
| GAPDH | 10.16 | 1 | 2 | Glyceraldehyde-3-phosphate dehydrogenase |
| ENO1 | 10.15 | 1 | 2 | Alpha-enolase |
| MARS | 10.15 | 1 | 1 | Methionyl-tRNA synthetase (cytoplasmic) |
| NUP107 | 10.15 | 1 | 1 | Nuclear pore complex |
| VHL-1 | 10.1 | 1 | 2 | Von Hippel Lindau Tumor Suppressor |
| VHL-3 | 10.1 | 1 | 2 | Von Hippel Lindau Tumor Suppressor |
| LARS | 10.14 | 1 | 2 | Leucyl-tRNA synthetase (cytoplasmic) |
| eEF1G | 10.11 | 1 | 2 | Elongation Factor 1-gamma |
| TARS2 | 8.13 | 1 | 1,2 | Threonyl-tRNA Synthetase (mitochondrial) |

1. Condition 1: over expressed TARS; Condition 2: over-expressed TARS and over-expressed VHL

FIGURE 16

SEQUENCE LISTING

<160> NUMBER OF SEQ ID NOS: 9

<210> SEQ ID NO 1
<211> LENGTH: 2888
<212> TYPE: DNA
<213> ORGANISM: Homo sapiens

<400> SEQUENCE: 1

```
ggtcagcgga gagtaggcat gtagcttctg cagttgctcc tcctcaccct ccgcgacctg      60
atttcctaga agggctctgt cacccgaaaa gattttccac tggcttagag gagggagggc     120
ccgccttccc ccgttatcca ttggctgctc gttccgccgc aagttggggg cggggttagg     180
gcgcctttcg attgcatcag ctggtccagc cgaggccaag tcccgggcgc tagcccacct     240
cccacccgcc tcttggctcc tctcctctag gccgtcgctt tcgggttctc tcatcgcttc     300
gtcgttcgcc aatgtttgag gagaaggcca gcagtccttc agggaagatg ggaggcgagg     360
agaagccgat tggtgctggt gaagagaagc aaaaggaagg aggcaaaaag aagaacaaag     420
aaggatctgg agatggaggt cgagctgagt tgaatccttg gcctgaatat atttacacac     480
gtcttgagat gtataatata ctaaaagcag aacatgattc cattctggca gaaaaggcag     540
aaaaagatag caagccaatt aaagtcactt tgcctgatgg taaacaggtt gatgcggaat     600
cttggaaaac tacaccatat caaattgcct gtggaattag tcaaggcctg gccgacaaca     660
ccgttattgc taaagtaaat aatgttgtgt gggacctgga ccgccctctg gaagaagatt     720
gtaccttgga gcttctcaag tttgaggatg aggaagctca ggcagtgtat tggcactcta     780
gtgctcacat aatgggtgaa gccatggaaa gagtctatg tggatgttta tgctacggtc     840
cgccaataga aaatggattc tattatgaca tgtacctcga agaaggggggt gtgtctagca     900 atgatttctc ttctctggag gctttgtgta agaaaatcat taaagaaaaa caagcttttg     960
aaagactgga agttaagaaa gaaactttac tggcaatgtt taagtacaac aagttcaaat    1020
gccggatatt gaatgaaaag gtgaatactc caactaccac agtctataga tgtggccctt    1080
tgatagatct ctgccggggt cctcatgtta gacacacggg caaaattaag gctttaaaaa    1140
tacacaaaaa ttcctccacg tactgggaag gcaaagcaga tatggagact ctccagagaa    1200
tttatggcat ttcattccca gatcctaaaa tgttgaaaga gtgggagaag ttccaagagg    1260
```

```
aagctaaaaa ccgagatcat aggaaaattg gcagggacca agaactatat ttctttcatg    1320
aactcagccc tggaagttgc ttttttctgc caaaaggagc ctacatttat aatgcactta    1380
ttgaattcat taggagcgaa tataggaaaa gaggattcca ggaggtagtc accccaaaca    1440
tcttcaacag ccgactctgg atgacctcgg gccactggca gcactacagc gagaacatgt    1500
tctcctttga ggtggagaag gagctgtttg ccctgaaacc catgaactgc ccaggacact    1560
gccttatgtt tgatcatcgg ccaaggtcct ggcgagaact gcctctgcgg ctagctgatt    1620
ttggggtact tcataggaac gagctgtctg gagcactcac aggactcacc cgggtacgaa    1680
gattccaaca ggatgatgct cacatattct gtgccatgga gcagattgaa gatgaaataa    1740
aaggttgttt ggattttcta cgtacggtat atagcgtatt tggattttct tttaaactaa    1800
acctttctac tcgcccggaa aaattccttg agatatcga agtatgggat caagctgaga    1860
aacaacttga aacagtctg aatgaatttg gtgaaaagtg ggagttaaac tctggagatg    1920
gagctttcta tggcccaaag attgacatac agattaaaga tgcgattggg cggtaccacc    1980
agtgtgcaac catccagctg gatttccagt tgcccatcag atttaatctt acttatgtaa    2040
gccatgatgg tgatgataag aaaaggccag tgattgttca tcgagccatc ttgggatcag    2100
tggaaagaat gattgctatc ctcacagaaa actatggggg caaatggccc ttttggctgt    2160
cccctcgcca ggtaatggta gttccagtgg gaccaacctg tgatgaatat gcccaaaagg    2220
tacgacaaca attccacgat gccaaattca tggcagacat tgatctggat ccaggctgta    2280
cattgaataa aaagattcga aatgcacagt tagcacagta taacttcatt ttagttgttg    2340
gtgaaaaaga gaaaatcagt ggcactgtta atatccgcac aagagacaat aaggtccacg    2400
gggaacgcac catttctgaa actatcgagc ggctacagca gctcaaagag ttccgcagca    2460
aacaggcaga agaagaattt taatgaaaaa attcccaga ttggctccat ggaaaaggag    2520
gaacagcgtt tccgtaaaat tgactttgta ctctgaaaac gtcaatttat attgaacttg    2580
gaggagtttg gcaaagtctg aataggtcaa cctgcaggcg taactatttt tgacctagtc    2640 agttttttaaa caatgtgcat ttgaaggagt taattaaaag agagccaata aaatgatttt    2700
actcattcag tatctgagta ctggaagtga acatgagga atgctttagt gtaatgtggg    2760 agaactttt tgtaaattta atgcaattga aaagtttttc aaattcaatt aagataacta    2820
gaattggatt atggtgtaaa aataaaaaaa aaatttattc acataaaaaa aaaaaaaaa    2880 aaaaaaaa                                                             2888
```

<210> SEQ ID NO 2
<211> LENGTH: 723
<212> TYPE: PRT
<213> ORGANISM: Homo sapiens

<400> SEQUENCE: 2

```
Met Phe Glu Glu Lys Ala Ser Ser Pro Ser Gly Lys Met Gly Gly Glu
1               5                   10                  15

Glu Lys Pro Ile Gly Ala Gly Glu Glu Lys Gln Lys Glu Gly Gly Lys
            20                  25                  30

Lys Lys Asn Lys Glu Gly Ser Gly Asp Gly Gly Arg Ala Glu Leu Asn
        35                  40                  45

Pro Trp Pro Glu Tyr Ile Tyr Thr Arg Leu Glu Met Tyr Asn Ile Leu
    50                  55                  60

Lys Ala Glu His Asp Ser Ile Leu Ala Glu Lys Ala Glu Lys Asp Ser
65                  70                  75                  80
```

-continued

Lys Pro Ile Lys Val Thr Leu Pro Asp Gly Lys Gln Val Asp Ala Glu
                85                  90                  95

Ser Trp Lys Thr Thr Pro Tyr Gln Ile Ala Cys Gly Ile Ser Gln Gly
                100                 105                 110

Leu Ala Asp Asn Thr Val Ile Ala Lys Val Asn Asn Val Val Trp Asp
                115                 120                 125

Leu Asp Arg Pro Leu Glu Glu Asp Cys Thr Leu Glu Leu Leu Lys Phe
        130                 135                 140

Glu Asp Glu Glu Ala Gln Ala Val Tyr Trp His Ser Ser Ala His Ile
145                 150                 155                 160

Met Gly Glu Ala Met Glu Arg Val Tyr Gly Gly Cys Leu Cys Tyr Gly
                165                 170                 175

Pro Pro Ile Glu Asn Gly Phe Tyr Tyr Asp Met Tyr Leu Glu Glu Gly
                180                 185                 190

Gly Val Ser Ser Asn Asp Phe Ser Ser Leu Glu Ala Leu Cys Lys Lys
        195                 200                 205

Ile Ile Lys Glu Lys Gln Ala Phe Glu Arg Leu Glu Val Lys Lys Glu
        210                 215                 220

Thr Leu Leu Ala Met Phe Lys Tyr Asn Lys Phe Lys Cys Arg Ile Leu
225                 230                 235                 240

Asn Glu Lys Val Asn Thr Pro Thr Thr Val Tyr Arg Cys Gly Pro
                245                 250                 255

Leu Ile Asp Leu Cys Arg Gly Pro His Val Arg His Thr Gly Lys Ile
                260                 265                 270

Lys Ala Leu Lys Ile His Lys Asn Ser Ser Thr Tyr Trp Glu Gly Lys
        275                 280                 285

Ala Asp Met Glu Thr Leu Gln Arg Ile Tyr Gly Ile Ser Phe Pro Asp
        290                 295                 300

Pro Lys Met Leu Lys Glu Trp Glu Lys Phe Gln Glu Glu Ala Lys Asn
305                 310                 315                 320

Arg Asp His Arg Lys Ile Gly Arg Asp Gln Glu Leu Tyr Phe Phe His
                325                 330                 335

Glu Leu Ser Pro Gly Ser Cys Phe Phe Leu Pro Lys Gly Ala Tyr Ile
                340                 345                 350

Tyr Asn Ala Leu Ile Glu Phe Ile Arg Ser Glu Tyr Arg Lys Arg Gly
        355                 360                 365

Phe Gln Glu Val Val Thr Pro Asn Ile Phe Asn Ser Arg Leu Trp Met
        370                 375                 380

Thr Ser Gly His Trp Gln His Tyr Ser Glu Asn Met Phe Ser Phe Glu
385                 390                 395                 400

Val Glu Lys Glu Leu Phe Ala Leu Lys Pro Met Asn Cys Pro Gly His
                405                 410                 415

Cys Leu Met Phe Asp His Arg Pro Arg Ser Trp Arg Glu Leu Pro Leu
                420                 425                 430

Arg Leu Ala Asp Phe Gly Val Leu His Arg Asn Glu Leu Ser Gly Ala
        435                 440                 445

Leu Thr Gly Leu Thr Arg Val Arg Arg Phe Gln Gln Asp Asp Ala His
        450                 455                 460

Ile Phe Cys Ala Met Glu Gln Ile Glu Asp Glu Ile Lys Gly Cys Leu
465                 470                 475                 480

Asp Phe Leu Arg Thr Val Tyr Ser Val Phe Gly Phe Ser Phe Lys Leu
                485                 490                 495

Asn Leu Ser Thr Arg Pro Glu Lys Phe Leu Gly Asp Ile Glu Val Trp
              500                 505                 510

Asp Gln Ala Glu Lys Gln Leu Glu Asn Ser Leu Asn Glu Phe Gly Glu
        515                 520                 525

Lys Trp Glu Leu Asn Ser Gly Asp Gly Ala Phe Tyr Gly Pro Lys Ile
    530                 535                 540

Asp Ile Gln Ile Lys Asp Ala Ile Gly Arg Tyr His Gln Cys Ala Thr
545                 550                 555                 560

Ile Gln Leu Asp Phe Gln Leu Pro Ile Arg Phe Asn Leu Thr Tyr Val
                565                 570                 575

Ser His Asp Gly Asp Lys Lys Arg Pro Val Ile Val His Arg Ala
            580                 585                 590

Ile Leu Gly Ser Val Glu Arg Met Ile Ala Ile Leu Thr Glu Asn Tyr
            595                 600                 605

Gly Gly Lys Trp Pro Phe Trp Leu Ser Pro Arg Gln Val Met Val Val
    610                 615                 620

Pro Val Gly Pro Thr Cys Asp Glu Tyr Ala Gln Lys Val Arg Gln Gln
625                 630                 635                 640

Phe His Asp Ala Lys Phe Met Ala Asp Ile Asp Leu Asp Pro Gly Cys
                645                 650                 655

Thr Leu Asn Lys Lys Ile Arg Asn Ala Gln Leu Ala Gln Tyr Asn Phe
            660                 665                 670

Ile Leu Val Val Gly Glu Lys Glu Lys Ile Ser Gly Thr Val Asn Ile
        675                 680                 685

Arg Thr Arg Asp Asn Lys Val His Gly Glu Arg Thr Ile Ser Glu Thr
690                 695                 700

Ile Glu Arg Leu Gln Gln Leu Lys Glu Phe Arg Ser Lys Gln Ala Glu
705                 710                 715                 720

Glu Glu Phe

<210> SEQ ID NO 3
<211> LENGTH: 722
<212> TYPE: PRT
<213> ORGANISM: Mus musculus

<400> SEQUENCE: 3

Met Ser Gln Glu Lys Ala Ser Ser Pro Ser Gly Lys Met Asp Gly Glu
1               5                   10                  15

Lys Pro Val Asp Ala Ser Glu Glu Lys Arg Lys Glu Gly Gly Lys Lys
            20                  25                  30

Lys Ser Lys Asp Gly Gly Gly Asp Gly Gly Arg Ala Glu Leu Asn Pro
        35                  40                  45

Trp Pro Glu Tyr Ile Asn Thr Arg Leu Asp Met Tyr Asn Lys Leu Lys
    50                  55                  60

Ala Glu His Asp Ser Ile Leu Ala Glu Lys Ala Lys Asp Ser Lys
65                  70                  75                  80

Pro Ile Lys Val Thr Leu Pro Asp Gly Lys Gln Val Asp Ala Glu Ser
                85                  90                  95

Trp Lys Thr Thr Pro Tyr Gln Ile Ala Cys Gly Ile Ser Gln Gly Leu
            100                 105                 110

Ala Asp Asn Thr Val Val Ala Lys Val Asn Lys Val Val Trp Asp Leu
        115                 120                 125

Asp Arg Pro Leu Glu Thr Asp Cys Thr Leu Glu Leu Leu Lys Phe Glu
    130                 135                 140

-continued

```
Asp Glu Glu Ala Gln Ala Val Tyr Trp His Ser Ala His Ile Met
145                 150                 155                 160

Gly Glu Ala Met Glu Arg Val Tyr Gly Gly Cys Leu Cys Tyr Gly Pro
                165                 170                 175

Pro Ile Glu Asn Gly Phe Tyr Tyr Asp Met Tyr Leu Glu Glu Gly Gly
            180                 185                 190

Val Ser Ser Asn Asp Phe Ser Ser Leu Glu Thr Leu Cys Lys Lys Ile
        195                 200                 205

Ile Lys Glu Lys Gln Thr Phe Glu Arg Leu Glu Lys Lys Glu Thr
210                 215                 220

Leu Leu Glu Met Phe Lys Tyr Asn Lys Phe Lys Cys Arg Ile Leu Asn
225                 230                 235                 240

Glu Lys Val Asn Thr Pro Thr Thr Thr Val Tyr Arg Cys Gly Pro Leu
                245                 250                 255

Ile Asp Leu Cys Arg Gly Pro His Val Arg His Thr Gly Lys Ile Lys
            260                 265                 270

Thr Leu Lys Ile His Lys Asn Ser Ser Thr Tyr Trp Glu Gly Lys Ala
        275                 280                 285

Asp Met Glu Thr Leu Gln Arg Ile Tyr Gly Ile Ser Phe Pro Asp Pro
290                 295                 300

Lys Leu Leu Lys Glu Trp Glu Lys Phe Gln Glu Ala Lys Asn Arg
305                 310                 315                 320

Asp His Arg Lys Ile Gly Arg Asp Gln Glu Leu Tyr Phe Phe His Glu
                325                 330                 335

Leu Ser Pro Gly Ser Cys Phe Phe Leu Pro Lys Gly Ala Tyr Ile Tyr
            340                 345                 350

Asn Thr Leu Met Glu Phe Ile Arg Ser Glu Tyr Arg Lys Arg Gly Phe
        355                 360                 365

Gln Glu Val Val Thr Pro Asn Ile Phe Asn Ser Arg Leu Trp Met Thr
370                 375                 380

Ser Gly His Trp Gln His Tyr Ser Glu Asn Met Phe Ser Phe Glu Val
385                 390                 395                 400

Glu Lys Glu Gln Phe Ala Leu Lys Pro Met Asn Cys Pro Gly His Cys
                405                 410                 415

Leu Met Phe Asp His Arg Pro Arg Ser Trp Arg Glu Leu Pro Leu Arg
            420                 425                 430

Leu Ala Asp Phe Gly Val Leu His Arg Asn Glu Leu Ser Gly Ala Leu
        435                 440                 445

Thr Gly Leu Thr Arg Val Arg Arg Phe Gln Gln Asp Asp Ala His Ile
450                 455                 460

Phe Cys Ala Met Glu Gln Ile Glu Asp Glu Ile Lys Gly Cys Leu Asp
465                 470                 475                 480

Phe Leu Arg Thr Val Tyr Ser Val Phe Gly Phe Ser Phe Lys Leu Asn
                485                 490                 495

Leu Ser Thr Arg Pro Glu Lys Phe Leu Gly Asp Ile Glu Ile Trp Asn
            500                 505                 510

Gln Ala Glu Lys Gln Leu Glu Asn Ser Leu Asn Glu Phe Gly Glu Lys
        515                 520                 525

Trp Glu Leu Asn Pro Gly Asp Gly Ala Phe Tyr Gly Pro Lys Ile Asp
530                 535                 540

Ile Gln Ile Lys Asp Ala Ile Gly Arg Tyr His Gln Cys Ala Thr Ile
545                 550                 555                 560

Gln Leu Asp Phe Gln Leu Pro Ile Arg Phe Asn Leu Thr Tyr Val Ser
```

-continued

```
                565                 570                 575
His Asp Gly Asp Asp Lys Lys Arg Pro Val Ile Val His Arg Ala Ile
            580                 585                 590

Leu Gly Ser Val Glu Arg Met Ile Ala Ile Leu Thr Glu Asn Tyr Gly
        595                 600                 605

Gly Lys Trp Pro Phe Trp Leu Ser Pro Arg Gln Val Met Val Val Pro
    610                 615                 620

Val Gly Pro Thr Cys Asp Glu Tyr Ala Gln Lys Val Arg Gln Gln Phe
625                 630                 635                 640

His Asp Ala Lys Phe Met Ala Asp Thr Asp Leu Asp Pro Gly Cys Thr
            645                 650                 655

Leu Asn Lys Lys Ile Arg Asn Ala Gln Leu Ala Gln Tyr Asn Phe Ile
        660                 665                 670

Leu Val Val Gly Glu Lys Glu Lys Ala Ser Gly Thr Val Asn Ile Arg
    675                 680                 685

Thr Arg Asp Asn Lys Val His Gly Glu Arg Thr Val Glu Glu Thr Val
690                 695                 700

Arg Arg Leu Gln Gln Leu Lys Gln Thr Arg Ser Lys Gln Ala Glu Glu
705                 710                 715                 720

Glu Phe

<210> SEQ ID NO 4
<211> LENGTH: 725
<212> TYPE: PRT
<213> ORGANISM: Caenorhabditis elegans

<400> SEQUENCE: 4

Met Arg Leu Asn Cys Phe Arg Ile Phe Val His Ile Gln Lys Pro Thr
1               5                   10                  15

Gln Ile Phe Lys Pro Phe Tyr Arg Ser Leu Ser Ser Glu Ala Ser Asp
            20                  25                  30

Lys Tyr His Phe Val Asn Gly His Lys Met Ser Lys Ala Pro Thr Asp
        35                  40                  45

Met Ala Pro Trp Pro Ala Phe Ile Glu Glu Arg Ile Lys Leu Trp Asp
    50                  55                  60

Lys Leu Lys Ala Glu Tyr Asp Ala Glu Ile Ala Ala Lys Glu Ser Glu
65                  70                  75                  80

Pro Ile Gln Ile Thr Leu Pro Asp Gly Lys Ile His Glu Gly Lys Thr
                85                  90                  95

Trp Arg Thr Thr Pro Phe Glu Ile Ala Glu Arg Ile Ser Lys Gly Leu
            100                 105                 110

Ala Glu Ala Ala Val Ile Ala Lys Val Asn Gly Ala Val Trp Asp Leu
        115                 120                 125

Asp Arg Pro Phe Glu Gly Asn Ala Lys Leu Glu Leu Leu Lys Phe Asp
    130                 135                 140

Asp Asp Glu Ala Lys Gln Val Phe Trp His Ser Ser Ala His Val Leu
145                 150                 155                 160

Gly Glu Ala Met Glu Arg Tyr Cys Gly Gly His Leu Cys Tyr Gly Pro
                165                 170                 175

Pro Ile Gln Glu Gly Phe Tyr Tyr Asp Met Trp His Glu Asn Arg Thr
            180                 185                 190

Ile Cys Pro Asp Asp Phe Pro Lys Ile Asp Gln Ile Val Lys Ala Ala
        195                 200                 205

Val Lys Asp Lys Gln Lys Phe Glu Arg Leu Glu Met Thr Lys Glu Asp
```

```
              210                 215                 220
Leu Leu Glu Met Phe Lys Tyr Asn Glu Phe Lys Val Arg Ile Ile Thr
225                 230                 235                 240

Glu Lys Ile His Thr Pro Lys Thr Thr Val Tyr Arg Cys Gly Pro Leu
                245                 250                 255

Ile Asp Leu Cys Arg Gly Pro His Val Arg His Thr Gly Lys Val Lys
                260                 265                 270

Ala Met Ala Ile Thr Lys Asn Ser Ser Ser Tyr Trp Glu Gly Lys Ala
            275                 280                 285

Asp Ala Glu Ser Leu Gln Arg Leu Tyr Gly Ile Ser Phe Pro Asp Ser
            290                 295                 300

Lys Gln Leu Lys Glu Trp Gln Lys Leu Gln Glu Glu Ala Ala Lys Arg
305                 310                 315                 320

Asp His Arg Lys Leu Gly Lys Glu His Asp Leu Phe Phe His Gln
                325                 330                 335

Leu Ser Pro Gly Ser Ala Phe Trp Tyr Pro Lys Gly Ala His Ile Tyr
                340                 345                 350

Asn Lys Leu Val Asp Phe Ile Arg Lys Gln Tyr Arg Arg Gly Phe
            355                 360                 365

Thr Glu Val Ile Thr Pro Asn Met Tyr Asn Lys Lys Leu Trp Glu Thr
            370                 375                 380

Ser Gly His Trp Gln His Tyr Ser Glu Asp Met Phe Lys Ile Glu Val
385                 390                 395                 400

Glu Lys Glu Glu Phe Gly Leu Lys Pro Met Asn Cys Pro Gly His Cys
                405                 410                 415

Leu Met Phe Gly His Met Pro His Thr Tyr Asn Glu Leu Pro Phe Arg
                420                 425                 430

Phe Ala Asp Phe Gly Val Leu His Arg Asn Glu Met Ser Gly Ala Leu
                435                 440                 445

Thr Gly Leu Thr Arg Val Arg Arg Phe Gln Gln Asp Asp Ala His Ile
            450                 455                 460

Phe Cys Arg Gln Asp Gln Ile Ser Glu Glu Ile Lys Gln Cys Leu Asp
465                 470                 475                 480

Phe Leu Glu Tyr Ala Tyr Glu Lys Val Phe Gly Phe Thr Phe Lys Leu
                485                 490                 495

Asn Leu Ser Thr Arg Pro Glu Gly Phe Leu Gly Asn Ile Glu Thr Trp
                500                 505                 510

Asp Lys Ala Glu Ala Asp Leu Thr Asn Ala Leu Asn Ala Ser Gly Arg
                515                 520                 525

Lys Trp Val Leu Asn Pro Gly Asp Gly Ala Phe Tyr Gly Pro Lys Ile
            530                 535                 540

Asp Ile Thr Ile Gln Asp Ala Leu Lys Arg Asn Phe Gln Cys Ala Thr
545                 550                 555                 560

Ile Gln Leu Asp Phe Gln Leu Pro Asn Gln Phe Asp Leu Ser Tyr Phe
                565                 570                 575

Asp Glu Lys Gly Glu Lys Gln Arg Pro Val Met Ile His Arg Ala Val
                580                 585                 590

Leu Gly Ser Val Glu Arg Met Thr Ala Ile Leu Thr Glu Ser Tyr Gly
            595                 600                 605

Gly Lys Trp Pro Phe Trp Leu Ser Pro Arg Gln Cys Lys Ile Ile Thr
            610                 615                 620

Val His Glu Ser Val Arg Asp Tyr Ala Asn Asp Val Lys Lys Gln Ile
625                 630                 635                 640
```

Phe Glu Ala Gly Phe Glu Ile Glu Tyr Glu Glu Asn Cys Gly Asp Thr
                645                 650                 655

Met Asn Lys Gln Val Arg Lys Ala Gln Leu Ala Gln Phe Asn Phe Ile
            660                 665                 670

Leu Val Ile Gly Ala Lys Glu Lys Glu Asn Gly Thr Val Asn Val Arg
            675                 680                 685

Thr Arg Asp Asn Ala Val Arg Gly Val Ala Leu Asp Lys Leu Ile
        690                 695                 700

Ser Lys Phe Arg Arg Phe Ala Asp Glu Tyr Val Ala Asp Thr Glu Lys
705                 710                 715                 720

Ser Glu Glu Trp Ala
            725

<210> SEQ ID NO 5
<211> LENGTH: 734
<212> TYPE: PRT
<213> ORGANISM: Saccharomyces cerevisiae

<400> SEQUENCE: 5

Met Ser Ala Ser Glu Ala Gly Val Thr Glu Gln Val Lys Lys Leu Ser
1               5                   10                  15

Val Lys Asp Ser Ser Asn Asp Ala Val Lys Pro Asn Lys Lys Glu Asn
            20                  25                  30

Lys Lys Ser Lys Gln Gln Ser Leu Tyr Leu Asp Pro Glu Pro Thr Phe
        35                  40                  45

Ile Glu Glu Arg Ile Glu Met Phe Asp Arg Leu Gln Lys Glu Tyr Asn
50                  55                  60

Asp Lys Val Ala Ser Met Pro Arg Val Pro Leu Lys Ile Val Leu Lys
65                  70                  75                  80

Asp Gly Ala Val Lys Glu Ala Thr Ser Trp Glu Thr Thr Pro Met Asp
                85                  90                  95

Ile Ala Lys Gly Ile Ser Lys Ser Leu Ala Asp Arg Leu Cys Ile Ser
            100                 105                 110

Lys Val Asn Gly Gln Leu Trp Asp Leu Asp Arg Pro Phe Glu Gly Glu
        115                 120                 125

Ala Asn Glu Glu Ile Lys Leu Glu Leu Leu Asp Phe Glu Ser Asp Glu
130                 135                 140

Gly Lys Lys Val Phe Trp His Ser Ser Ala His Val Leu Gly Glu Ser
145                 150                 155                 160

Cys Glu Cys His Leu Gly Ala His Ile Cys Leu Gly Pro Pro Thr Asp
                165                 170                 175

Asp Gly Phe Phe Tyr Glu Met Ala Val Arg Asp Ser Met Lys Asp Ile
            180                 185                 190

Ser Glu Ser Pro Glu Arg Thr Val Ser Gln Ala Asp Phe Pro Gly Leu
        195                 200                 205

Glu Gly Val Ala Lys Asn Val Ile Lys Gln Lys Gln Lys Phe Glu Arg
210                 215                 220

Leu Val Met Ser Lys Glu Asp Leu Leu Lys Met Phe His Tyr Ser Lys
225                 230                 235                 240

Tyr Lys Thr Tyr Leu Val Gln Thr Lys Val Pro Asp Gly Gly Ala Thr
                245                 250                 255

Thr Val Tyr Arg Cys Gly Lys Leu Ile Asp Leu Cys Val Gly Pro His
            260                 265                 270

Ile Pro His Thr Gly Arg Ile Lys Ala Phe Lys Leu Leu Lys Asn Ser

```
            275                 280                 285
Ser Cys Tyr Phe Leu Gly Asp Ala Thr Asn Asp Ser Leu Gln Arg Val
290                 295                 300
Tyr Gly Ile Ser Phe Pro Asp Lys Lys Leu Met Asp Ala His Leu Lys
305                 310                 315                 320
Phe Leu Ala Glu Ala Ser Met Arg Asp His Arg Lys Ile Gly Lys Glu
                325                 330                 335
Gln Glu Leu Phe Leu Phe Asn Glu Met Ser Pro Gly Ser Cys Phe Trp
            340                 345                 350
Leu Pro His Gly Thr Arg Ile Tyr Asn Thr Leu Val Asp Leu Leu Arg
        355                 360                 365
Thr Glu Tyr Arg Lys Arg Gly Tyr Glu Glu Val Ile Thr Pro Asn Met
370                 375                 380
Tyr Asn Ser Lys Leu Trp Glu Thr Ser Gly His Trp Ala Asn Tyr Lys
385                 390                 395                 400
Glu Asn Met Phe Thr Phe Glu Val Glu Lys Glu Thr Phe Gly Leu Lys
                405                 410                 415
Pro Met Asn Cys Pro Gly His Cys Leu Met Phe Lys Ser Arg Glu Arg
            420                 425                 430
Ser Tyr Arg Glu Leu Pro Trp Arg Val Ala Asp Phe Gly Val Ile His
        435                 440                 445
Arg Asn Glu Phe Ser Gly Ala Leu Ser Gly Leu Thr Arg Val Arg Arg
    450                 455                 460
Phe Gln Gln Asp Asp Ala His Ile Phe Cys Thr His Asp Gln Ile Glu
465                 470                 475                 480
Ser Glu Ile Glu Asn Ile Phe Asn Phe Leu Gln Tyr Ile Tyr Gly Val
                485                 490                 495
Phe Gly Phe Glu Phe Lys Met Glu Leu Ser Thr Arg Pro Glu Lys Tyr
            500                 505                 510
Val Gly Lys Ile Glu Thr Trp Asp Ala Ala Glu Ser Lys Leu Glu Ser
        515                 520                 525
Ala Leu Lys Lys Trp Gly Gly Asn Trp Glu Ile Asn Ala Gly Asp Gly
    530                 535                 540
Ala Phe Tyr Gly Pro Lys Ile Asp Ile Met Ile Ser Asp Ala Leu Arg
545                 550                 555                 560
Arg Trp His Gln Cys Ala Thr Ile Gln Leu Asp Phe Gln Leu Pro Asn
                565                 570                 575
Arg Phe Glu Leu Glu Phe Lys Ser Lys Asp Gln Asp Ser Glu Ser Tyr
            580                 585                 590
Glu Arg Pro Val Met Ile His Arg Ala Ile Leu Gly Ser Val Glu Arg
        595                 600                 605
Met Thr Ala Ile Leu Thr Glu His Phe Ala Gly Lys Trp Pro Phe Trp
    610                 615                 620
Leu Ser Pro Arg Gln Val Leu Val Pro Val Gly Val Lys Tyr Gln
625                 630                 635                 640
Gly Tyr Ala Glu Asp Val Arg Asn Lys Leu His Asp Ala Gly Phe Tyr
                645                 650                 655
Ala Asp Val Asp Leu Thr Gly Asn Thr Leu Gln Lys Lys Val Arg Asn
            660                 665                 670
Gly Gln Met Leu Lys Tyr Asn Phe Ile Phe Ile Val Gly Glu Gln Glu
        675                 680                 685
Met Asn Glu Lys Ser Val Asn Ile Arg Asn Arg Asp Val Met Glu Gln
    690                 695                 700
```

```
Gln Gly Lys Asn Ala Thr Val Ser Val Glu Val Leu Lys Gln Leu
705                 710                 715                 720

Arg Asn Leu Lys Asp Glu Lys Arg Gly Asp Asn Val Leu Ala
                725                 730
```

<210> SEQ ID NO 6
<211> LENGTH: 723
<212> TYPE: PRT
<213> ORGANISM: Homo sapiens

<400> SEQUENCE: 6

```
Met Phe Glu Glu Lys Ala Ser Ser Pro Ser Gly Lys Met Gly Gly Glu
1               5                   10                  15

Glu Lys Pro Ile Gly Ala Gly Glu Glu Lys Gln Lys Glu Gly Gly Lys
            20                  25                  30

Lys Lys Asn Lys Glu Gly Ser Gly Asp Gly Arg Ala Glu Leu Asn
        35                  40                  45

Pro Trp Pro Glu Tyr Ile Tyr Thr Arg Leu Glu Met Tyr Asn Ile Leu
    50                  55                  60

Lys Ala Glu His Asp Ser Ile Leu Ala Glu Lys Ala Glu Lys Asp Ser
65                  70                  75                  80

Lys Pro Ile Lys Val Thr Leu Pro Asp Gly Lys Gln Val Asp Ala Glu
                85                  90                  95

Ser Trp Lys Thr Thr Pro Tyr Gln Ile Ala Cys Gly Ile Ser Gln Gly
            100                 105                 110

Leu Ala Asp Asn Thr Val Ile Ala Lys Val Asn Asn Val Val Trp Asp
        115                 120                 125

Leu Asp Arg Pro Leu Glu Glu Asp Cys Thr Leu Glu Leu Leu Lys Phe
130                 135                 140

Glu Asp Glu Glu Ala Gln Ala Val Tyr Trp His Ser Ser Ala His Ile
145                 150                 155                 160

Met Gly Glu Ala Met Glu Arg Val Tyr Gly Gly Cys Leu Cys Tyr Gly
                165                 170                 175

Pro Pro Ile Glu Asn Gly Phe Tyr Tyr Asp Met Tyr Leu Glu Glu Gly
            180                 185                 190

Gly Val Ser Ser Asn Asp Phe Ser Ser Leu Glu Ala Leu Cys Lys Lys
        195                 200                 205

Ile Ile Lys Glu Lys Gln Ala Phe Glu Arg Leu Glu Val Lys Lys Glu
210                 215                 220

Thr Leu Leu Ala Met Phe Lys Tyr Asn Lys Phe Lys Cys Arg Ile Leu
225                 230                 235                 240

Asn Glu Lys Val Asn Thr Pro Thr Thr Thr Val Tyr Arg Cys Gly Pro
                245                 250                 255

Leu Ile Asp Leu Cys Arg Gly Pro His Val Arg His Thr Gly Lys Ile
            260                 265                 270

Lys Ala Leu Lys Ile His Lys Asn Ser Ser Thr Tyr Trp Glu Gly Lys
        275                 280                 285

Ala Asp Met Glu Thr Leu Gln Arg Ile Tyr Gly Ile Ser Phe Pro Asp
290                 295                 300

Pro Lys Met Leu Lys Glu Trp Glu Lys Phe Gln Glu Glu Ala Lys Asn
305                 310                 315                 320

Arg Asp His Arg Lys Ile Gly Arg Asp Gln Glu Leu Tyr Phe Phe His
                325                 330                 335

Glu Leu Ser Pro Gly Ser Cys Phe Phe Leu Pro Lys Gly Ala Tyr Ile
```

```
            340             345             350
Tyr Asn Ala Leu Ile Glu Phe Ile Arg Ser Glu Tyr Arg Lys Arg Gly
            355             360             365
Phe Gln Glu Val Val Thr Pro Asn Ile Phe Asn Ser Arg Leu Trp Met
        370             375             380
Thr Ser Gly His Trp Gln His Tyr Ser Glu Asn Met Phe Ser Phe Glu
385             390             395             400
Val Glu Lys Glu Leu Phe Ala Leu Lys Pro Met Asn Cys Pro Gly His
                405             410             415
Cys Leu Met Phe Asp His Arg Pro Arg Ser Trp Arg Glu Leu Pro Leu
            420             425             430
Arg Leu Ala Asp Phe Gly Val Leu His Arg Asn Glu Leu Ser Gly Ala
        435             440             445
Leu Thr Gly Leu Thr Arg Val Arg Arg Phe Gln Gln Asp Asp Ala His
    450             455             460
Ile Phe Cys Ala Met Glu Gln Ile Glu Asp Glu Ile Lys Gly Cys Leu
465             470             475             480
Asp Phe Leu Arg Thr Val Tyr Ser Val Phe Gly Phe Ser Phe Lys Leu
                485             490             495
Asn Leu Ser Thr Arg Pro Glu Lys Phe Leu Gly Asp Ile Glu Val Trp
            500             505             510
Asp Gln Ala Glu Lys Gln Leu Glu Asn Ser Leu Asn Glu Phe Gly Glu
        515             520             525
Lys Trp Glu Leu Asn Ser Gly Asp Gly Ala Phe Tyr Gly Pro Lys Ile
    530             535             540
Asp Ile Gln Ile Lys Asp Ala Ile Gly Arg Tyr His Gln Cys Ala Thr
545             550             555             560
Ile Gln Leu Asp Phe Gln Leu Pro Ile Arg Phe Asn Leu Thr Tyr Val
                565             570             575
Ser His Asp Gly Asp Asp Lys Lys Arg Pro Val Ile Val His Arg Ala
            580             585             590
Ile Leu Gly Ser Val Glu Arg Met Ile Ala Ile Leu Thr Glu Asn Tyr
        595             600             605
Gly Gly Lys Trp Pro Phe Trp Leu Ser Pro Arg Gln Val Met Val Val
    610             615             620
Pro Val Gly Pro Thr Cys Asp Glu Tyr Ala Gln Lys Val Arg Gln Gln
625             630             635             640
Phe His Asp Ala Lys Phe Met Ala Asp Ile Asp Leu Asp Pro Gly Cys
                645             650             655
Thr Leu Asn Lys Lys Ile Arg Asn Ala Gln Leu Ala Gln Tyr Asn Phe
            660             665             670
Ile Leu Val Val Gly Glu Lys Glu Lys Ile Ser Gly Thr Val Asn Ile
        675             680             685
Arg Thr Arg Asp Asn Lys Val His Gly Glu Arg Thr Ile Ser Glu Thr
    690             695             700
Ile Glu Arg Leu Gln Gln Leu Lys Glu Phe Arg Ser Lys Gln Ala Glu
705             710             715             720
Glu Glu Phe

<210> SEQ ID NO 7
<211> LENGTH: 100
<212> TYPE: PRT
<213> ORGANISM: Homo sapiens
```

```
<400> SEQUENCE: 7

Arg Ala Glu Leu Asn Pro Trp Pro Glu Tyr Ile Tyr Thr Arg Leu Glu
1               5                   10                  15

Met Tyr Asn Ile Leu Lys Ala Glu His Asp Ser Ile Leu Ala Glu Lys
            20                  25                  30

Ala Glu Lys Asp Ser Lys Pro Ile Lys Val Thr Leu Pro Asp Gly Lys
        35                  40                  45

Gln Val Asp Ala Glu Ser Trp Lys Thr Thr Pro Tyr Gln Ile Ala Cys
    50                  55                  60

Gly Ile Ser Gln Gly Leu Ala Asp Asn Thr Val Ile Ala Lys Val Asn
65                  70                  75                  80

Asn Val Val Trp Asp Leu Asp Arg Pro Leu Glu Glu Asp Cys Thr Leu
                85                  90                  95

Glu Leu Leu Lys
            100

<210> SEQ ID NO 8
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 8
caccagtgtg caaccatcca gctggatttc caggtgccca tcagatttaa tc        52

<210> SEQ ID NO 9
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 9
gattaaatct gatgggccac tggaaatcca gctggatggt tgcacactgg tg        52
```

METHODS AND COMPOUNDS FOR INCREASING THREONYL-TRNA SYNTHETASE ACTIVITY

RELATED APPLICATIONS

This application is a National Stage Filing under U.S.C. § 371 of PCT International Application PCT/US2013/51807, filed Jul. 24, 2013 which was published under PCT Article 21(2) in English, which claims benefit under 35 U.S.C. § 119(e) of U.S. Provisional Application No. 61/675,669, filed Jul. 25, 2012 and the content of each of which is incorporated by reference herein in its entirety.

GOVERNMENT INTEREST

This invention was made with government support under RO1 GM54899 and by training grant T32 ES007122-23 both awarded by the National Institutes of Health. The Government has certain rights in the invention.

FIELD OF THE INVENTION

The invention relates, in part, to methods and compounds for increasing threonyl-tRNA synthetase (TARS) activity in cells and tissues.

BACKGROUND

Angiogenesis plays a role in diseases such as cancer and other proliferative disorders. For example, a small solid tumor may be able to survive in the absence of vascularization, but to provide sufficient nutrients and oxygen and to remove waste products from cells that make up larger tumors, vascularization of the tissue is necessary. Triggers and regulators of angiogenesis in cells and tissues are not fully understood, but it is thought that hypoxia and lack of adequate nutritional access in cells in tumors greater than approximately 2 $cm^3$ in size may result in angiogenesis, which supports further tumor growth with increased delivery of oxygen and nutrients. Angiogenesis may be a factor in the progression of a tumor or cancer, not only by providing nutrient support for a tumor to continue to grow in size, but angiogenesis may also play a role in metastatic activity in some cancers.

Angiogenesis has emerged as a target for cancer therapy due to the reliance of many cancers on new vessels and the poor prognosis associated with cancers that have advanced angiogenesis (Folkman, J. (2001) *Semin Oncol* 28 (6), 536-542). Angiogenesis is normally suppressed by angiopoietin-1 which is secreted by vascular pericytes and inhibits endothelial cell proliferation. There are many factors involved in the tumor angiogenic switch, but initiation of angiogenesis by hypoxic tumor cells is primarily through induction of hypoxia inducible factor-1α (HIF-1α) which stimulates expression of vascular endothelial growth factor (VEGF). VEGF acts in combination with other growth factors and receptors to increase activation of the Ras/MAP kinase and phosphoinositide 3 kinase (PI3 kinase) pathways in endothelial cells. These pathways are involved in induction of genes involved in endothelial cell proliferation and migration. (Bikfalvi, A. and Bicknell, R. (2002) *Trends in Pharmacological Sciences* 23 (12), 576-582; Liao, D. and Johnson, R. (2007) *Cancer and Metastasis Reviews* 26 (2), 281-290; and Olsson, A. K. et al. (2006) *Nat Rev Mol Cell Biol* 7 (5), 359-371).

Cell and tissue growth, for example vascular growth in angiogenesis, are known to involve protein synthesis but processes involved in the initiation, regulation, and modulation of protein synthesis in angiogenesis appear to be quite complex and are not well understood. The lack of understanding of the complex pathways and interactive regulatory events necessary to trigger and support angiogenesis in cells limits approaches to treat disorders that are characterized, in part, by insufficient angiogenesis.

SUMMARY OF THE INVENTION

The invention includes, in part, methods and compounds for treating diseases and conditions characterized by and/or associated with altered threonyl-tRNA synthetase (TARS) activity, which include, but are not limited to diseases and conditions in which angiogenesis is altered. It has now been shown for the first time that TARS is a potent angiogenic inducer in vitro and in vivo affecting endothelial cell migration and tube formation. TARS is also shown to be secreted by endothelial cells in response to angiogenic or inflammatory signaling, indicating its novel role as a pro-angiogenic chemokine. Furthermore, an association is revealed between TARS levels and both ovarian and prostate cancers in human patient samples.

According to an aspect of the invention, methods of increasing angiogenesis in at least one cell are provided. The methods include contacting a plurality of cells with an effective amount of a TARS-activity-enhancing compound to increase angiogenesis at least one cell of the plurality of cells. In some embodiments, the TARS-activity-enhancing compound mediates IL-6 and/or increases STAT3 levels. In certain embodiments, the TARS-activity-enhancing compound includes TNF-a, which causes TARS to be secreted from HUVEC cells. In some embodiments, the TARS-activity-enhancing compound includes a threonyl-tRNA synthetase (TARS) molecule or variant thereof. In some embodiments, the plurality of cells is in culture. In some embodiments, the culture is an organ culture. In certain embodiments, the plurality of cells is in a subject and contacting the cells includes administering the TARS-activity-enhancing compound to the subject. In some embodiments, the TARS-activity-enhancing compound is threonyl-tRNA synthetase (TARS) molecule or variant thereof. In some embodiments, the subject has or is at risk of having an angiogenesis-associated disease or condition. In some embodiments, the angiogenesis-associated disease or condition is a tissue implant, organ implant, ischemia, cardiac infarction, tissue trauma, cartilage to bone transformation, stroke, surgery, pregnancy, macular degeneration, vascular occlusion, or conditions for which it is desirable to have a stronger immune response such as in (a) certain types of cancers; (b) viral infection, particularly HIV infected individuals with weakened immune systems; (b) bacterial or eukaryotic pathogen infection, etc. In some embodiments, the method also includes contacting the plurality of cells with one or more additional angiogenesis-enhancing compounds. In some embodiments, contacting the plurality of cells with the TARS-activity-enhancing compound and one or more of the additional angiogenesis-enhancing compounds results in a synergistic increase in angiogenesis in the plurality of cells. In some embodiments, the TARS-activity-enhancing compound is administered to the subject as a pharmaceutical composition. In certain embodiments, the pharmaceutical composition includes a TARS-activity-enhancing compound and a pharmaceutically acceptable carrier. In some embodiments, the TARS-activity-enhancing compound includes a threonyl-tRNA synthetase (TARS) molecule or a variant thereof. In some embodiments, the subject is a human. In certain embodiments, the TARS-activity-enhancing compound is administered orally, parenterally, intraperitoneally, subcutaneously, intranasally, intravenously, intrathecally, intramuscularly, intracranially, transmucosally, vaginally, via instillation, rectally, or topically. In some embodiments, the TARS molecule has the nucleic acid sequence set forth as SEQ ID NO:1 or a fragment thereof. In some embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In some embodiments, the TARS molecule has the amino acid sequence set forth as SEQ ID NO:2 or a fragment thereof. In certain embodiments, the TARS fragment has the amino acid sequence of SEQ ID NO:2 with at least 1, 2, 3, 4, 5, 6, 7, 8, 9, 10, or more amino acid deletions. In some embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In some embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In some embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequences set forth as SEQ ID NO:2. In certain embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2. In some embodiments, the plurality of cells includes one or more pre-vascular cells, angioblasts, endothelial cells, vascular cells, immune system cells. In some embodiments, the threonyl-tRNA synthetase (TARS) molecule, fragment, or variant thereof, is administered after diagnosis of an angiogenesis-associated disease or condition.

According to another aspect of the invention, methods of increasing angiogenesis in a subject are provided. The methods include administering to the subject in need of such treatment an effective amount of a TARS-activity-enhancing compound to increase angiogenesis in the subject. In certain embodiments, the TARS-activity-enhancing compound is threonyl-tRNA synthetase (TARS) molecule or variant thereof. In some embodiments, the TARS-activity-enhancing compound mediates IL-6 and/or increases STAT3 levels. In some embodiments, the TARS-activity-enhancing compound includes TNF-a, which causes TARS to be secreted from HUVEC cells. In certain embodiments, the subject has or is at risk of having an angiogenesis-associated disease or condition. In some embodiments, the angiogenesis-associated disease or condition is a tissue implant, organ implant, ischemia, cardiac infarction, tissue trauma, cartilage to bone transformation, stroke, surgery, pregnancy, macular degeneration, vascular occlusion, conditions for which it is desirable to have a stronger immune response such as in some types of cancers; viral infections, subjects with HIV infections and weakened immune systems; bacterial or eukaryotic pathogen infections. In some embodiments, the method also includes administering one or more additional angiogenesis-enhancing compounds to the subject. In some embodiments, administering the TARS-activity enhancing compound and the one or more of the additional angiogenesis-enhancing compounds results in a synergistic increase in angiogenesis in the subject. In certain embodiments, the TARS-activity-enhancing compound is administered to the subject as a pharmaceutical composition including the TARS-activity-enhancing compound and a pharmaceutically acceptable carrier. In some embodiments, the threonyl-tRNA synthetase (TARS) molecule or variant thereof is administered to the subject as a pharmaceutical composition. In some embodiments, the pharmaceutical composition includes a threonyl-tRNA synthetase (TARS) molecule or variant thereof, and a pharmaceutically acceptable carrier. In certain embodiments, the subject is a human. In some embodiments, the TARS-activity-enhancing compound is administered orally, parenterally, intraperitoneally, subcutaneously, intranasally, intravenously, intrathecally, intramuscularly, intracranially, transmucosally, vaginally, via instillation, rectally, or topically. In some embodiments, the TARS molecule has the nucleic acid sequence set forth as SEQ ID NO:1 or a fragment thereof. In some embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In certain embodiments, the TARS molecule has the amino acid sequence set forth as SEQ ID NO:2 or a fragment thereof. In some embodiments, the TARS fragment has the amino acid sequence of SEQ ID NO:2 with at least 1, 2, 3, 4, 5, 6, 7, 8, 9, 10, or more amino acid deletions. In some embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In some embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In certain embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequences set forth as SEQ ID NO:2. In some embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2. In some embodiments, the threonyl-tRNA synthetase (TARS) molecule, fragment, or variant thereof, is administered after diagnosis of an angiogenesis-associated disease or condition.

According to another aspect of the invention, methods of increasing angiogenesis in a plurality of cells are provided. The methods include contacting the plurality of cells with a compound that increases an interaction of threonyl-tRNA synthetase (TARS) with VHL in at least one cell in the plurality of cells, wherein the increase in the interaction increases angiogenesis in the plurality of cells. In certain embodiments, the interaction of TARS with VHL includes the formation, maintenance, or activity of a TARS/VHL complex. In some embodiments, increasing the interaction of the TARS/VHL complex includes increasing the formation of a TARS/VHL complex in the plurality of cells. In some embodiments, increasing the interaction of the TARS/VHL complex includes increasing the activity of a TARS/VHL complex in the plurality of cells. In some embodiments, increasing the interaction of the TARS/VHL complex includes increasing the maintenance of a TARS/VHL complex in the plurality of cells. In certain embodiments, increasing the maintenance of the TARS/VHL complex activity includes reducing disassociation of the TARS/VHL complex. In some embodiments, the plurality of cells is in culture. In some embodiments, the culture is an organ culture. In some embodiments, the compound includes a threonyl-tRNA synthetase (TARS) molecule or variant thereof. In certain embodiments, the TARS-activity-enhancing compound mediates IL-6 and/or increases STAT3 levels. In some embodiments, the wherein the TARS-activity-enhancing compound includes TNF-a, which causes TARS to be secreted from HUVEC cells. In some embodiments, the plurality of cells is in a subject and contacting the cells includes administering a threonyl-tRNA synthetase (TARS) molecule or variant thereof to the subject. In some embodiments, the subject has or is at risk of having an angiogenesis-associated disease or condition. In some embodiments, the angiogenesis-associated disease or condition is a tissue implant, organ implant, ischemia, cardiac infarction, tissue trauma, cartilage to bone transformation, stroke, surgery, pregnancy, macular degeneration, vascular occlusion, or conditions for which it is desirable to have a stronger immune response such as in (a) certain cancers; viral infections, HIV, bacterial or eukaryotic pathogen infections. In some embodiments, the method also includes contacting the plurality of cells with one or more additional angiogenesis-enhancing compounds. In some embodiments, contacting the plurality of cells with the TARS-activity-enhancing compound and one or more of the additional angiogenesis-enhancing compounds results in a synergistic increase in angiogenesis in the plurality of cells. In some embodiments, the TARS-activity-enhancing compound is administered to the subject as a pharmaceutical composition. In some embodiments, the pharmaceutical composition includes a TARS-activity-enhancing compound and a pharmaceutically acceptable carrier. In certain embodiments, the TARS-activity-enhancing compound includes a threonyl-tRNA synthetase (TARS) molecule or a variant thereof. In some embodiments, the subject is a human. In some embodiments, the TARS-activity-enhancing compound is administered orally, parenterally, intraperitoneally, subcutaneously, intranasally, intravenously, intrathecally, intramuscularly, intracranially, transmucosally, vaginally, via instillation, rectally, or topically. In some embodiments, the TARS molecule has the nucleic acid sequence set forth as SEQ ID NO:1 or a fragment thereof. In some embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In some embodiments, the TARS molecule has the amino acid sequence set forth as SEQ ID NO:2 or a fragment thereof. In certain embodiments, the TARS fragment has the amino acid sequence of SEQ ID NO:2 with at least 1, 2, 3, 4, 5, 6, 7, 8, 9, 10, or more amino acid deletions. In some embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In some embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In some embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequence set forth as SEQ ID NO:2. In some embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2.

According to yet another aspect of the invention, methods of assisting in the selection of a treatment to increase angiogenesis in a subject are provided. The methods include obtaining a cell sample from a subject having or at risk of having an angiogenesis-associated disease or condition; determining the threonyl-tRNA synthetase (TARS)/von Hippel Lindau factor (VHL) interaction in the cell sample; comparing the determined TARS/VHL interaction to a control TARS/VHL interaction; and selecting a treatment for the angiogenesis-associated disease or condition in the subject based at least in part on the difference between the determined TARS/VHL interaction and the control TARS/VHL interaction, wherein if the determined TARS/VHL interaction is lower than the control interaction, the selected treatment increases the TARS/VHL interaction in the subject and increases angiogenesis in the subject. In some embodiments, the interaction of TARS with VHL includes the formation, maintenance, or activity of a TARS/VHL complex. In certain embodiments, increasing the interaction of the TARS/VHL complex includes increasing the formation of a TARS/VHL complex in the subject. In some embodiments, increasing the interaction of the TARS/VHL complex includes increasing the activity of a TARS/VHL complex in the subject. In some embodiments, increasing the interaction of the TARS/VHL complex includes increasing the maintenance of a TARS/VHL complex in the subject. In certain embodiments, increasing the maintenance of the TARS/VHL complex activity includes reducing disassociation of the TARS/VHL complex. In some embodiments, the control TARS/VHL interaction is a predetermined standard TARS/VHL. In some embodiments, the control is a normal control. In some embodiments, determining the interaction includes determining the level of the TARS/VHL complex in a tissue sample from the subject. In certain embodiments, selecting the treatment includes comparing the level of the TARS/VHL complex with a control level of TARS/VHL complex and basing the selection at least in part on the comparison. In some embodiments, selecting the treatment is based at least in part on monitoring the GTPase activity of eEF1 to assess TARS function, and its effect on VHL. In some embodiments, the treatment for the angiogenesis-associated disease or condition includes administering to the subject an effective amount of a TARS-activity-enhancing compound to increase angiogenesis in the subject. In certain embodiments, the TARS-activity-enhancing compound includes threonyl-tRNA synthetase (TARS) molecule or a variant thereof. In some embodiments, the TARS-activity-enhancing compound mediates IL-6 and/or increases STAT3 levels. In some embodiments, the TARS-activity-enhancing compound includes TNF-a, which causes TARS to be secreted from HUVEC cells. In some embodiments, the TARS molecule has the nucleic acid sequence set forth as SEQ ID NO:1 or a fragment thereof. In some embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In certain embodiments, the TARS molecule has the amino acid sequence set forth as SEQ ID NO:2 or a fragment thereof. In some embodiments, the TARS fragment has the amino acid sequence of SEQ ID NO:2 with at least 1, 2, 3, 4, 5, 6, 7, 8, 9, 10, or more amino acid deletions. In some embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In some embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In some embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequences set forth as SEQ ID NO:2. In certain embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2.

According to another aspect of the invention, methods of identifying a candidate compound to increase angiogenesis in a plurality of cells are provided. The methods include contacting a plurality of cells with a candidate compound and determining the effect of the contact on a TARS/VHL interaction in the plurality of cells, wherein a compound that increases the TARS/VHL interaction in the plurality of cells, is a candidate angiogenesis-increasing compound. In some embodiments, the interaction of TARS with VHL includes the formation, maintenance, or activity of a TARS/VHL complex. In some embodiments, increasing the interaction of the TARS/VHL complex includes increasing the formation of TARS/VHL complex in the plurality of cells. In certain embodiments, increasing the interaction of the TARS/VHL complex includes increasing the activity of a TARS/VHL complex in the plurality of cells. In some embodiments, increasing the interaction of the TARS/VHL complex includes increasing the maintenance of a TARS/VHL complex in the plurality of cells. In some embodiments, increasing the maintenance of the TARS/VHL complex activity includes reducing disassociation of the TARS/VHL complex. In certain embodiments, the method also includes comparing the TARS/VHL interaction in the plurality of cells with a control TARS/VHL interaction in a plurality of cells not contacted with the candidate compound, wherein the an increase in the TARS/VHL interaction in the plurality of cells compared to the control level indicates that the candidate compound is a candidate angiogenesis-increasing compound. In some embodiments, determining the TARS/VHL interaction includes determining the level of the TARS/VHL complex in the plurality of cells. In some embodiments, the plurality of cells is in culture. In certain embodiments, the plurality of cells is from a sample obtained from a subject. In some embodiments, the subject has or is suspected of having an angiogenesis-associated disease or condition. In some embodiments, the angiogenesis-associated disease or condition is a tissue implant, organ implant, ischemia, cardiac infarction, tissue trauma, cartilage to bone transformation, stroke, surgery, pregnancy, macular degeneration, vascular occlusion, or conditions for which it is desirable to have a stronger immune response such as some types of cancers; viral infection, HIV in an infected individual with a weakened immune system; a bacterial infection or a eukaryotic pathogen infection.

According to yet another aspect of the invention, pharmaceutical compositions that include a TARS-activity-enhancing compound and a pharmaceutically acceptable carrier are provided. In certain embodiments, the TARS-activity-enhancing compound mediates IL-6 and/or increases STAT3 levels. In some embodiments, the TARS-activity-enhancing compound includes TNF-a, which causes TARS to be secreted from HUVEC cells. In some embodiments, the TARS-activity-enhancing compound includes threonyl-tRNA synthetase (TARS) molecule or variant thereof. In some embodiments, the TARS molecule has the nucleic acid sequence set forth as SEQ ID NO:1 or a fragment thereof. In certain embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In some embodiments, the TARS molecule has the amino acid sequence set forth as SEQ ID NO:2 or a fragment thereof. In some embodiments, the TARS fragment has the amino acid sequence of SEQ ID NO:2 with at least 1, 2, 3, 4, 5, 6, 7, 8, 9, 10, or more amino acid deletions. In some embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In certain embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In some embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequences set forth as SEQ ID NO:2. In some embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2. In certain embodiments, the pharmaceutical composition also includes one or more additional angiogenesis-enhancing compounds. In some embodiments, the composition is formulated for oral, parenteral, nasal, intravenous, intrathecal, intramuscular, intracranial, transmucosal, vaginal, instillation, rectal, or topical administration.

According to another aspect of the invention, methods of immune system enhancement in a subject are provided. The methods include administering to the subject in need of such treatment an effective amount of a TARS-activity-enhancing compound to enhance the immune system in the subject. In some embodiments, the TARS-activity-enhancing compound mediates IL-6 and/or increases STAT3 levels. In some embodiments, the TARS-activity-enhancing compound includes TNF-a, which causes TARS to be secreted from HUVEC cells. In certain embodiments, the TARS-activity-enhancing compound is threonyl-tRNA synthetase (TARS) molecule or variant thereof. In some embodiments, the subject has or is at risk of having an immune system-associated disease or condition. In some embodiments, enhancing the immune system includes increasing T cell development in the subject. In some embodiments, the methods also include administering one or more additional immune system-enhancing compounds to the subject. In certain embodiments, administering the TARS-activity enhancing compound and the one or more of the additional immune system-enhancing compounds results in a synergistic enhancement in the immune system in the subject. In some embodiments, the TARS-activity-enhancing compound is administered to the subject as a pharmaceutical composition including the TARS-activity-enhancing compound and a pharmaceutically acceptable carrier. In some embodiments, the threonyl-tRNA synthetase (TARS) molecule or variant thereof is administered to the subject as a pharmaceutical composition. In certain embodiments, the pharmaceutical composition includes a threonyl-tRNA synthetase (TARS) molecule or variant thereof, and a pharmaceutically acceptable carrier. In some embodiments, the subject is a human. In some embodiments, the TARS-activity-enhancing compound is administered orally, parenterally, intraperitoneally, subcutaneously, intranasally, intravenously, intrathecally, intramuscularly, intracranially, transmucosally, vaginally, via instillation, rectally, or topically. In some embodiments, the TARS molecule has the nucleic acid sequence set forth as SEQ ID NO:1 or a fragment thereof. In certain embodiments, the nucleic acid sequence of the TARS fragment has the nucleic acid sequence of SEQ ID NO:1 with at least 1, 2, 3, 4, 5, 6, 7, 8, 9, 10, or more nucleic acid deletions. In some embodiments, the TARS molecule has the amino acid sequence set forth as SEQ ID NO:2 or a fragment thereof. In some embodiments, the TARS fragment has the amino acid sequence of SEQ ID NO:2 with at least 1, 2, 3, 4, 5, 6, 7, 8, 9, 10, or more amino acid deletions. In certain embodiments, the TARS molecule variant has a nucleic acid sequence that is at least 75%, 80%, 85%, 90%, 95%, 97%, 98%, 99% identical to the nucleic acid sequence set forth as SEQ ID NO:1 or a fragment thereof. In some embodiments, the TARS molecule variant has an amino acid sequence that is at least 75%, 80%, 85%, 90%, 95%, 97%, 98%, 99% identical to the amino acid sequence set forth as SEQ ID NO:2 or a fragment thereof. In some embodiments, the variant of the TARS molecule includes the nucleic acid sequence set forth as SEQ ID NO:1, or a fragment thereof, modified to encode a TARS polypeptide having one, two, three, four, five, or more conservative amino acid changes in the amino acid sequences set forth as SEQ ID NO:2. In some embodiments, the variant of the TARS molecule includes the amino acid sequence set forth as SEQ ID NO:2, or a fragment thereof modified to have one, two, three, four, five, or more conservative amino acid changes in the amino acid sequence set forth as SEQ ID NO:2. In certain embodiments, the threonyl-tRNA synthetase (TARS) molecule, fragment, or variant thereof, is administered after diagnosis of an immune system-associated disease or condition.

BRIEF DESCRIPTION OF THE DRAWINGS

FIG. 1B shows results from 10 nM BC194, and FIG. 1C shows results from 1000 nM BC194. Scale bar=100 µm. Graph in FIG. 1D shows quantification of branches over a range of BC194 concentrations using the Simple Neurite Tracer plug-in on ImageJ software. Numbers represent average data from 3 separate experiments performed in duplicate. Multiple comparisons of one-way ANOVA were performed using the Tukey Test; n=3, *p<0.05.

FIG. 4A is a graph showing effects of BC194 on cell viability. HUVECs were exposed to the indicated concentrations of BC194, and live cells were quantified by trypan blue exclusion and normalized to the untreated control; n=3, *p<0.05. FIG. 4B is a graph showing effects of BC194 on proliferation. HUVECs were exposed to the indicated concentrations of BC194 and proliferation was quantified over time using an Alamar Blue™ assay (a measure of NADPH oxidase activity). n=3, *p<0.05. FIG. 4C is a flow cytometry analysis, and FIG. 4D is an SDS-PAGE showing lack of effects of BC194 on nascent protein synthesis. Cells were exposed to the indicated concentrations of BC194 and new protein synthesis was detected using a Click-iT® metabolic labeling kit. Proteins were separated by SDS-PAGE and visualized using streptavidin-HRP. Cycloheximide (CHX, 50 µM) was used as a control for complete inhibition of protein synthesis.

FIG. 5A shows results using Coomassie stain of TARS and L567V TARS proteins separated by SDS-PAGE indicating purified intact proteins. FIG. 5B is a graph showing that purified TARS exhibits aminoacyl synthetase activity and activity is not compromised in the borrelidin-resistant mutant L567V. TARS activity was comparable to E. coli TARS and commercially available human TARS expressed in CHO cells (Francklyn, First et al. 2008).

FIGS. 6A, 6B, and 6C show results using low serum, full serum, and low serum+TARS, respectively. HUVECs were plated onto Matrigel in low serum (LS, 0.2% fetal bovine serum) or EGM-2 full serum media (FS, 5% FBS). Where indicated, 100 nM purified recombinant human TARS was added to the media. Tubes were imaged and analyzed after 6 h as in FIG. 1, Scale bar=100 µm. FIG. 6D is a histograph of quantified branches; n=3, *p<0.01 compared to low serum. FIG. 6E is a histogram of quantified branches for TARS effect; mean±standard error of the mean, n=3, *P, 0.01 compared to Low Serum (Student's test). FIG. 6F is a histogram of quantified branches for a range of BC194 concentrations added to Full Serum media. Numbers represent mean±standard error of the mean, n=3, *P<0.05 (one-way ANOVA, Tukey test).

(FIG. 7A) BC194 (10 nM) was applied to the CAM along with PBS (Control), bFGF (40 µg/ml), and VEGF (2 µg/ml). The angiostatic control retinoic acid (RA) was used at 100 µg/ml. Representative images for (FIG. 7A) are shown in FIG. 8B, and FIG. 8C. Purified recombinant TARS, BC194-resistant mutant TARS (L567V) and BC194 were applied at 100 µg/ml. FIG. 7C shows representative CAM images over time; arrows denote spoke-wheel response. Scale bar=1.0 mm. FIG. 7B is a histogram of change in CAM vascularity score over 72 h; n≥14, *p<0.001 compared to PBS control; #p<0.001 compared to TARS.

FIG. 9A shows Coomassie stain of 2 µg LARS separated by SDS-PAGE. FIG. 9B shows a graph indicating that LARS exhibits enzyme activity as measured by conversion of $^{32}$P-ATP to AMP. Numbers represent labeled AMP determined by thin layer chromatography followed by phosphorimaging. FIGS. 9C and 9D indicate that LARS has no effect on angiogenesis measured in the CAM assay. Purified LARS (100 ng/sponge) was added to CAMs as in FIG. 8. FIG. 9C provides representative images showing no effect of LARS on CAM vascularity; Scale bar=1.0 mm. FIG. 9D provides a graph representing the average CAM vascularity score over 72 h as compared to PBS or TARS; n=5, *p<0.05.

In FIG. 10A HUVECs were treated with VEGF or TNF-α (50 ng/ml) where indicated. After 6 h the level of TARS in the supernatant was determined by ELISA. Graph represents an average of 3 experiments; *p<0.05. FIG. 10B shows cell membrane integrity for the experiments in (A and C) using the lactate dehydrogenase assay CytoTox-ONE™ at 6 h and 16 h. Numbers represent percent cytotoxicity relative to a lysis control. For FIG. 10C HUVECs grown on a 10 cm dish were exposed to 50 ng/ml of VEGF or TNF-α in 0% serum EGM-2 media for 16 h. Shown is a representative TARS Western blot of cell lysates and media samples, n=4. Media was concentrated 20-fold to accommodate 25% onto the gel and compared to 5% of the cell lysate. Purified TARS was used to estimate the TARS concentration within samples. β-tubulin was measured as a loading and lysis control. FIG. 10D shows that VEGF and TNF-α do not induce TARS transcription. HUVECs were exposed to 50 ng/ml of VEGF or TNF-α followed by RNA extraction and RT-qPCR to measure TARS mRNA levels. Shown are Rq values relative to a β-2 macroglobulin control; n=3. FIG. 10E shows that TARS does not induce VEGF secretion. HUVECs were exposed to the indicated concentrations of purified recombinant human TARS for 24 h and the level of VEGF in the supernatant determined by ELISA; n=3.

FIG. 11A shows results indicating that TARS does not significantly affect cell proliferation. HUVECs were cultured in low serum (0.2% FBS) media containing 50 ng/ml VEGF and 10 nM BC194 where indicated; relative proliferation was measured over time using an Alamar Blue™ assay; n=3. FIGS. 11B and C show VEGF and TARS-mediated migration. HUVEC migration was measured using a trans-well assay. The migration compartment contained 50 ng/ml VEGF, 100 nM LARS or 100 nM TARS and 10 nM BC194 where indicated. Shown in FIG. 11B are representative images of DAPI stained nuclei from migrated cells after 4 h. FIG. 11C shows a histogram representing number of migrated cells after 4 h for the conditions indicated; n≥3, *p<0.05 compared to Control, #p<0.05 compared to VEGF.

FIG. 13B presents a graph representing statistical analysis of TARS expression score as related to tumor diagnosis. Slides were scored by at least two pathologists, with a third tie breaker when necessary. Values within bars represent number of patients. *p<0.0001. FIG. 13C presents a table describing TARS serum measurements in four age matched control subjects and ten prostate cancer patients in various stages of diagnosis and treatment.

FIG. 16 lists the putative interacting partners of TARS, as determined from an affinity purification-mass spectrometry experiment. In all experiments, TARS was over-expressed (with a biotinylatable tag tail) and then affinity purified on streptavidin-conjugated beads. The bound proteins were then removed from the beads by boiling, resolved on SDS polyacrylamide gels, and then extracted from individual gel slices. The experiment was performed under two conditions. In Condition 1, only TARS was overexpressed; in Condition 2, both TARS and VHL were overexpressed.

FIG. 17A is a graph comparing the aminoacylation progress curves of wild and R442A mutant TARS. Based on the results of this assay, R442A TARS has virtually negligible aminoacylation function. FIG. 17B compares the change in CAM vascularity score for wild type, BC-194 resistant L567V TARS and aminoacylation-deficient R442A TARS. The histograms represent the change in vascularity score over 72 hour; *p<0.001 compared to PBS control; #P<0.001 compared to TARS. FIG. 17C is a graph comparing the progress curves of Ap4A formation for human TARS, R442A TARS, and TARS in the presence of BC194 or borrelidin. FIG. 17D is a graph comparing the progress curves of Ap4A formation for human TARS, R442A TARS, and TARS in the presence of (10 µM) BC194 or borrelidin (10 µM). FIGS. 17C and 17D indicate that Ap4A and Ap4G synthesis is blocked in R442A TARS, and its synthesis is at least partially inhibited by borrelidin and BC914. FIG. 17E is a graph comparing the progress curves of GTP hydrolysis for human TARS, R442A TARS, and $E.\ coli$ ThrRS in the presence of (10 mM) BC194 or borrelidin. This plot indicates that wild type human and R442 TARS both possess potent GTPase activities, but the bacterial enzyme does not. FIG. 17F is a graph comparing the progress curves of GTP hydrolysis for human TARS in the presence of substrates that are specific for the aminoacylation reaction. The key result is that when ATP and aminoacylation substrates are present, GTPase function is severely inhibited.

AMINO ACID AND NUCLEOTIDE SEQUENCES

SEQ ID NO: 1

Figure 1:
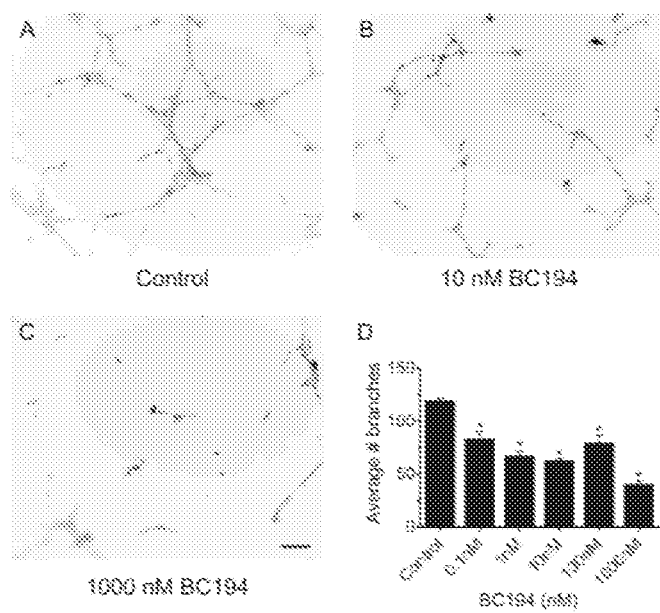
FIG. 1 provides photomicrographic images and a graph providing evidence that a subnanomolar concentration of the TARS inhibitor BC194 inhibits endothelial tube formation. Human umbilical vein endothelial cells (HUVECs) were seeded on Matrigel™ in full serum media (2% FBS) along with the indicated concentrations of BC194. After 6 h, cells were fixed and stained with Oregon Green 488 Phalloidin. Shown are representative images using the full serum media response as Control (FIG. 1A)

Human TARS nucleic acid sequence is provided as GENBANK ™ Accession No. NM_152295. mRNA.

```
ggtcagcggagagtaggcatgtagcttctgcagttgctcctcctcaccaccgcgacctgatttcctagaagggctctgtcacccg aaaagatttccactggcttagaggagggagggcccgccttcccccgttatccattggctgctcgttccgccgcaagttggggc gggggttagggcgcctttcgattgcatcagctggtccagccgaggccaagtcccgggcgctagcccacctcccaccccgcctcttg gctcctctcctctaggccgtcgctttcgggttctctcatcgcttcgtcgttcgccaatgtttgaggagaaggccagcagtccttcagg gaagatgggaggcgaggagaagccgattggtgctggtgaagagaagcaaaaggaaggaggcaaaaagaagaacaaagaa ggatctggagatggaggtcgagctgagttgaatccttggcctgaatatatttacacacgtcttgagatgtataatatactaaaagca gaacatgattccattctggcagaaaaggcagaaaaagatagcaagccaattaaagtcactttgcctgatggtaaacaggttgatg cggaatcttggaaaactacaccatatcaaattgcctgtggaattagtcaaggcctggccgacaacaccgttattgctaaagtaaata atgttgtgtgggacctggaccgccactggaagaagattgtaccttggagcttctcaagtttgaggatgaggaagctcaggcagt gtattggcactctagtgctcacataatgggtgaagccatggaaagagtctatggtggatgtttatgctacggtccgccaatagaaa atggattctattatgacatgtacctcgaagaagggggtgtgtctagcaatgatttctcttctctggaggctttgtgtaagaaaatcatta aagaaaaacaagcttttgaaagactggaagttaagaaagaaactttactggcaatgtttaagtacaacaagttcaaatgccggatat tgaatgaaaaggtgaatactccaactaccacagtctatagatgtggcccttttgatagatctctgccggggtcctcatgttagacaca cgggcaaaattaaggcttaaaaatacacaaaaattcctccacgtactgggaaggcaaagcagatatggagactctccagagaat ttatggcatttcattcccagatcctaaaatgttgaaagagtgggagaagttccaagaggaagctaaaaaccgagatcataggaaa attggcagggaccaagaactatatttctttcatgaactcagccctggaagttgattttctgccaaaaggagcctacatttataatgc acttattgaattcattaggagcgaatataggaaaagaggattccaggaggtagtcaccccaaacatcttcaacagccgactctgga tgacctcgggccactggcagcactacagcgagaacatgttctcctttgaggtggagaaggagctgtttgccctgaaacccatgaa
```

-continued ctgcccaggacactgccttatgtttgatcatcggccaaggtcctggcgagaactgcctctgcggctagctgattttggggtacttca taggaacgagctgtctggagcactcacaggactcacccgggtacgaagattccaacaggatgatgctcacatattctgtgccatg gagcagattgaagatgaaataaaaggttgtttggattttctacgtacggtatatagcgtatttggattttcttttaaactaaacctttctac tcgcccggaaaaattccttggagatatcgaagtatgggatcaagctgagaaacaacttgaaaacagtctgaatgaatttggtgaaa agtgggagttaaactctggagatggagctttctatggcccaaagattgacatacagattaaagatgcgattgggcggtaccacca gtgtgcaaccatccagctggatttccagttgcccatcagatttaatcttacttatgtaagccatgatggtgatgataagaaaaggcca gtgattgttcatcgagccatcttgggatcagtggaagaatgattgctatcctcacagaaaactatgggggcaaatggccctttttgg ctgtcccctcgccaggtaatggtagttccagtgggaccaacctgtgatgaatatgcccaaaaggtacgacaacaattccacgatg ccaaattcatggcagacattgatctggatccaggctgtacattgaataaaaagattcgaaatgcacagttagcacagtataacttca ttttagttgttggtgaaaaagagaaaatcagtggcactgttaatatccgcacaagagacaataaggtccacggggaacgcaccatt tctgaaactatcgagcggctacagcagctcaaagagttccgcagcaaacaggcagaagaagaattttaatgaaaaaattaccca gattggctccatggaaaaggaggaacagcgtttccgtaaaattgactttgtactctgaaaacgtcaatttatattgaacttggagga gtttggcaaagtctgaataggtcaacctgcaggcgtaactatttttgacctagtcagttttaaacaatgtgcatttgaaggagttaatt aaaagagagccaataaaatgattttactcattcagtatctgagtactggaagtgaaacatgaggaatgctttagtgtaatgtgggag aactttttgtaaatttaatgcaattgaaaaagttttcaaattcaattaagataactagaattggattatggtgtaaaaataaaaaaaaaa tttattcacataaaaaaaaaaaaaaaaaaaaaaaa.

SEQ ID NO: 2
A human TARS protein sequence is provided as GENBANK ™ Accession
No. P26639, which is also the amino acid sequence encoded by SEQ ID NO: 1, which is
set forth under GENBANK ™ Accession No. NM_152295
MFEEKASSPSGKMGGEEKPIGAGEEKQKEGGKKKNKEGSGDGGRAELNPWPEYI

YTRLEMYNILKAEHDSILAEKAEKDSKPIKVTLPDGKQVDAESWKTTPYQIACGI

SQGLADNTVIAKVNNVVWDLDRPLEEDCTLELLKFEDEEAQAVYWHSSAHIMG

EAMERVYGGCLCYGPPIENGFYYDMYLEEGGVSSNDFSSLEALCKKIIKEKQAFE

RLEVKKETLLAMFKYNKFKCRILNEKVNTPTTTVYRCGPLIDLCRGPHVRHTGKI

KALKIHKNSSTYWEGKADMETLQRIYGISFPDPKMLKEWEKFQEEAKNRDHRKI

GRDQELYFFHELSPGSCFFLPKGAYIYNALIEFIRSEYRKRGFQEVVTPNIFNSRLW

MTSGHWQHYSENMFSFEVEKELFALKPMNCPGHCLMFDHRPRSWRELPLRLAD

FGVLHRNELSGALTGLTRVRRFQQDDAHIFCAMEQIEDEIKGCLDFLRTVYSVFG

FSFKLNLSTRPEKFLGDIEVWDQAEKQLENSLNEFGEKWELNSGDGAFYGPKIDI

QIKDAIGRYHQCATIQLDFQLPIRFNLTYVSHDGDDKKRPVIVHRAILGSVERMIAI

LTENYGGKWPFWLSPRQVMVVPVGPTCDEYAQKVRQQFHDAKFMADIDLDPG

CTLNKKIRNAQLAQYNFILVVGEKEKISGTVNIRTRDNKVHGERTISETIERLQQL

KEFRSKQAEEEF.

SEQ ID NO: 3
Mus musculus TARS polypeptide sequence having GENBANK ™
Accession No. Q9D0R2.
MSQEKASSPSGKMDGEKPVDASEEKRKEGGKKKSKDGGGDGGRAELNPWPEYI

NTRLDMYNKLKAEHDSILAEKAAKDSKPIKVTLPDGKQVDAESWKTTPYQIACG

ISQGLADNTVVAKVNKVVWDLDRPLETDCTLELLKFEDEEAQAVYWHSSAHIM

GEAMERVYGGCLCYGPPIENGFYYDMYLEEGGVSSNDFSSLETLCKKIIKEKQTF

ERLEVKKETLLEMFKYNKFKCRILNEKVNTPTTTVYRCGPLIDLCRGPHVRHTGK

IKTLKIHKNSSTYWEGKADMETLQRIYGISFPDPKLLKEWEKFQEEAKNRDHRKI

GRDQELYFFHELSPGSCFFLPKGAYIYNTLMEFIRSEYRKRGFQEVVTPNIFNSRL

-continued

```
WMTSGHWQHYSENMFSFEVEKEQFALKPMNCPGHCLMFDHRPRSWRELPLRLA

DFGVLHRNELSGALTGLTRVRRFQQDDAHIFCAMEQIEDEIKGCLDFLRTVYSVF

GFSFKLNLSTRPEKFLGDIEIWNQAEKQLENSLNEFGEKWELNPGDGAFYGPKIDI

QIKDAIGRYHQCATIQLDFQLPIRFNLTYVSHDGDDKKRPVIVHRAILGSVERMIAI

LTENYGGKWPFWLSPRQVMVVPVGPTCDEYAQKVRQQFHDAKFMADTDLDPG

CTLNKKIRNAQLAQYNFILVVGEKEKASGTVNIRTRDNKVHGERTVEETVRRLQ

QLKQTRSKQAEEEF.
```

SEQ ID NO: 4

C Elegans TARS polypeptide sequence having GENBANK™ Accession
No. P52709.
```
MRLNCFRIFVHIQKPTQIFKPFYRSLSSEASDKYHFVNGHKMSKAPTDMAPWPAF

IEERIKLWDKLKAEYDAEIAAKESEPIQITLPDGKIHEGKTWRTTPFEIAERISKGL

AEAAVIAKVNGAVWDLDRPFEGNAKLELLKFDDDEAKQVFWHSSAHVLGEAM

ERYCGGHLCYGPPIQEGFYYDMWHENRTICPDDFPKIDQIVKAAVKDKQKFERL

EMTKEDLLEMFKYNEFKVRIITEKIHTPKTTVYRCGPLIDLCRGPHVRHTGKVKA

MAITKNSSSYWEGKADAESLQRLYGISFPDSKQLKEWQKLQEEAAKRDHRKLGK

EHDLFFFHQLSPGSAFWYPKGAHIYNKLVDFIRKQYRRRGFTEVITPNMYNKKL

WETSGHWQHYSEDMFKIEVEKEEFGLKPMNCPGHCLMFGHMPHTYNELPRFA

DFGVLHRNEMSGALTGLTRVRRFQQDDAHIFCRQDQISEEIKQCLDFLEYAYEKV

FGFTFKLNLSTRPEGFLGNIETWDKAEADLTNALNASGRKWVLNPGDGAFYGPK

IDITIQDALKRNFQCATIQLDFQLPNQFDLSYFDEKGEKQRPVMIHRAVLGSVERM

TAILTESYGGKWPFWLSPRQCKIITVHESVRDYANDVKKQIFEAGFEIEYEENCGD

TMNKQVRKAQLAQFNFILVIGAKEKENGTVNVRTRDNAVRGEVALDKLISKFRR

FADEYVADTEKSEEWA.
```

SEQ ID NO: 5

S cerevisiae TARS polypeptide sequence having GENBANK™ Accession
No. P04801.
```
MSASEAGVTEQVKKLSVKDSSNDAVKPNKKENKKSKQQSLYLDPEPTFIEERIEM

FDRLQKEYNDKVASMPRVPLKIVLKDGAVKEATSWETTPMDIAKGISKSLADRL

CISKVNGQLWDLDRPFEGEANEEIKLELLDFESDEGKKVFWHSSAHVLGESCECH

LGAHICLGPPTDDGFFYEMAVRDSMKDISESPERTVSQADFPGLEGVAKNVIKQK

QKFERLVMSKEDLLKMFHYSKYKTYLVQTKVPDGGATTVYRCGKLIDLCVGPHI

PHTGRIKAFKLLKNSSCYFLGDATNDSLQRVYGISFPDKKLMDAHLKFLAEASM

RDHRKIGKEQELFLFNEMSPGSCFWLPHGTRIYNTLVDLLRTEYRKRGYEEVITP

NMYNSKLWETSGHWANYKENMFTFEVEKETFGLKPMNCPGHCLMFKSRERSY

RELPWRVADFGVIHRNEFSGALSGLTRVRRFQQDDAHIFCTHDQIESEIENIFNFL

QYIYGVFGFEFKMELSTRPEKYVGKIETWDAAESKLESALKKWGGNWEINAGDG

AFYGPKIDIMISDALRRWHQCATIQLDFQLPNRFELEFKSKDQDSESYERPVMIHR

AILGSVERMTAILTEHFAGKWPFWLSPRQVLVVPVGVKYQGYAEDVRNKLHDA

GFYADVDLTGNTLQKKVRNGQMLKYNFIFIVGEQEMNEKSVNIRNRDVMEQQG

KNATVSVEEVLKQLRNLKDEKRGDNVLA.
```

SEQ ID NO: 6

Homo sapiens TARS cytoplasmic isoform 1 having GENBANK ™
Accession No NP_689508.
MFEEKASSPSGKMGGEEKPIGAGEEKQKEGGKKKNKEGSGDGGRAELNPWPEYI

YTRLEMYNILKAEHDSILAEKAEKDSKPIKVTLPDGKQVDAESWKTTPYQIACGI

SQGLADNTVIAKVNNVVWDLDRPLEEDCTLELLKFEDEEAQAVYWHSSAHIMG

EAMERVYGGCLCYGPPIENGFYYDMYLEEGGVSSNDFSSLEALCKKIIKEKQAFE

RLEVKKETLLAMFKYNKFKCRILNEKVNTPTTTVYRCGPLIDLCRGPHVRHTGKI

KALKIHKNSSTYWEGKADMETLQRIYGISFPDPKMLKEWEKFQEEAKNRDHRKI

GRDQELYFFHELSPGSCFFLPKGAYIYNALIEFIRSEYRKRGFQEVVTPNIFNSRLW

MTSGHWQHYSENMFSFEVEKELFALKPMNCPGHCLMFDHRPRSWRELPLRLAD

FGVLHRNELSGALTGLTRVRRFQQDDAHIFCAMEQIEDEIKGCLDFLRTVYSVFG

FSFKLNLSTRPEKFLGDIEVWDQAEKQLENSLNEFGEKWELNSGDGAFYGPKIDI

QIKDAIGRYHQCATIQLDFQLPIRFNLTYVSHDGDDKKRPVIVHRAILGSVERMIAI

LTENYGGKWPFWLSPRQVMVVPVGPTCDEYAQKVRQQFHDAKFMADIDLDPG

CTLNKKIRNAQLAQYNFILVVGEKEKISGTVNIRTRDNKVHGERTISETIERLQQL

KEFRSKQAEEEF.

SEQ ID NO: 7 is a portion of the sequence set forth in GENBANK ™ Accession No.:
NM_152295.
RAELNPWPEYIYTRLEMYNILKAEHDSILAEKAEKDSKPIKVTLPDGKQVDAESW

KTTPYQIACGISQGLADNTVIAKVNNVVWDLDRPLEEDCTLELLK.

SEQ ID NO: 8 is forward primer
5' caccagtgtgcaaccatccagctggatttccaggtgcccatcagatttaatc 3'.

SEQ ID NO: 9 is reverse primer
5' gattaaatctgatgggccactggaaatccagctggatggttgcacactggtg 3'.

DETAILED DESCRIPTION

Angiogenesis is involved in many cellular functions and processes including in diseases and conditions such as tissue or organ implants, ischemia, cardiac infarction, tissue trauma, cartilage to bone transformation, stroke, surgery, pregnancy, macular degeneration, vascular occlusion, which may be characterized by the presence of insufficient angiogenesis and/or a for which it may be desirable to increase angiogenesis as a treatment. In addition, TARS activity has now also been found to be associated with immune system activity and methods of the invention, in part, include in some aspects treatments that increase TARS activity in order to enhance immune system activity and treat an immune system disease or condition. Thus, methods of the invention can be used to treat angiogenic and/or immune system diseases or conditions. As used herein an "angiogenic" disease or condition is also referred to as an "angiogenesis-associated" disease or condition.

It has now been identified that threonyl-tRNA synthetase (TARS) plays a role in angiogenesis and can be used in methods to treat diseases and conditions characterized by abnormal (e.g., decreased) levels of TARS. As used herein with respect to TARS molecule activity and quantitation, the terms "decrease", "reduced", and "lower" are used interchangeably. As used herein, with respect to TARS activity, the terms: "increased", "elevated", and "higher" are used interchangeably.

The development of vasculature, e.g., angiogenesis, involves changes in protein synthesis and may be initiated by environmental stress such as hypoxia or starvation in a cell. Aminoacyl tRNA synthetases are believed to function in some aspects of angiogenesis. It is now understood that levels of TARS expression and function can be modulated in methods to treat angiogenic diseases and conditions that are characterized at least in part by decreased TARS activity. Diseases and conditions that have decreased TARS activity may include angiogenic and/or immune system diseases and conditions, examples of which are provided herein. Thus, the improved understanding the role of TARS in early angiogenesis signaling and immune function have now been used to identify novel treatment targets to recognize and treat angiogenic and immune system conditions, and to increases angiogenesis and immune system function, thus improving the likelihood of successful treatment.

Protein synthesis is known to include activities of aminoacyl tRNA synthetases, which are enzymes that catalyze the aminoacylation of tRNA by their cognate amino acids. Threonyl-tRNA synthetase (TARS) is an aminoacyl tRNA synthetase that is known to charge tRNA with threonine during protein synthesis. Protein synthesis plays a role in many different activities of cells and tissues such as growth and development, differentiation, replication, signaling, etc. and alterations in aminoacyl tRNA synthetase activities and functions may result in disruption of cell processes and disease. One non-limiting example of a disorder that TARS activity may play a role in is cancer.

Cancer cells respond to environmental stress and the tumor microenvironment plays a role in determining cancer cell survival and growth responses. Cancer cells rely on these responses because they rapidly outgrow their blood supply and must survive under conditions of hypoxia, starvation, and metabolic stress. Cells relieve these stresses by decreasing protein translation through the unfolded protein response and increasing blood supply through secretion of angiogenic cytokines and growth factors. A novel connection between these metabolic and angiogenic responses has now been identified and features, in part, the ability of tRNA synthetase inhibitors to alter the angiogenesis signaling pathway through a novel mechanism. In addition to having a role in cancer, angiogenesis also occurs physiologically during fetal development, wound healing, pregnancy, weight gain, and ischemic preconditioning, and is a feature found numerous additional diseases and conditions. In addition, it has now been identified that increased TARS activity is associated with increased immune system activity and that in some immune system diseases and conditions in which activity of the immune system is too low, methods of the invention that include increasing TARS activity may be used to treat such immune system disease and conditions. Thus, some aspects of the invention include methods to treat an immune system disease or condition. Examples of immune system conditions that can be treated with methods and TARS-activity-enhancing compounds of the invention, include, but are not limited to conditions such as infections, for example, by microbial agents; eukaryotic pathogens (for example, of fungal origin) or viral infections, non-limiting examples of which include infection by HIV-1 or other viruses that suppress the immune system. In some embodiments of the invention, administering an effective amount of a TARS-activity-enhancing compound enhances the immune system, which in some cases includes increasing T cell development in the subject. A TARS-activity-enhancing compound of the invention may be administered to a subject in conjunction with, or in series with, one or more additional immune system-enhancing compounds, and in some embodiments, the resulting effect in the subject includes a synergistic enhancement of the immune system in the subject.

TARS is an aminoacyl-tRNA synthetase that selectively catalyzes the ATP-dependent formation of threonyl-tRNA, a substrate for the protein translation machinery. Aside from their canonical functions in protein synthesis, aminoacyl-tRNA synthetases have been implicated in autoimmune and cytokine function, recovery from hypoxic stress, and angiogenesis. (Brown, M. V. et al. (2010) *Vascul Pharmacol* 52 (1-2), 21-26). Secretion and cytokine activities of extracellular TARS have now been examined and it has now been identified that TARS is secreted under conditions of exposure to cytokines (e.g., TNF-α and VEGF) and that one or more specific domains of TARS, including the N-terminal domain of TARS (the TGS domain), are regulatory in nature and able to confer cytokine activity.

Threonyl-tRNA synthetase (TARS) is a metabolic workhorse that functions to charge tRNA with threonine during protein synthesis. TARS is ubiquitously expressed in a number of prokaryotic and eukaryotic organisms. TARS is alternatively known as threonine tRNA ligase 1; Threonine-tRNA ligase, threonyl-transfer ribonucleate synthetase, threonyl-transfer RNA synthetase, threonyl-transfer ribonucleic acid synthetase, threonyl ribonucleic synthetase, threonine-transfer ribonucleate synthetase, threonine translase, TRS, and ThrRS. An example of a human TARS protein sequence is provided as GENBANK™ Accession No. P26639. Examples of TARS polypeptide sequences of other species include: *Mus musculus*: GENBANK™ Accession No. Q9D0R2; *C Elegans*: GENBANK™ Accession No. P52709; *S cerevisiae*: GENBANK™ Accession No. P04801. A human TARS nucleic acid sequence is provided as GENBANK™ Accession No. NM_152295.

It has now been discovered that TARS acts in a previously unknown manner to promote angiogenesis. Studies have now shown that inhibition of TARS reduces both the hypoxic response of cancer cells and, unexpectedly, that application of exogenous purified TARS also stimulated angiogenesis in an in vivo angiogenesis assay. Thus, TARS may have dual functions as a metabolic regulator and as an angiogenic cytokine, and may be secreted from cells exposed to ischemic stress. It has also now been found that TARS mRNA and TARS polypeptide may be selectively overexpressed in various cancers, including but not limited to ovarian tumors, which are highly angiogenic. An association between TARS polypeptide expression and activity levels are positively correlated with angiogenesis. It has also now also been identified that levels and/or activity of TARS mRNA and TARS polypeptide may be lower than normal in certain diseases and conditions, examples of which are described herein.

It has now been shown that an increase in expression and/or activity of TARS is correlated with an increase in angiogenesis of cells and also that an increase in expression and/or activities of TARS (potentially including GTPase and Ap4A synthetic functions) is correlated with metastasis of a cancer compared to a lower level of expression and/or activity of TARS in a poorly metastatic or non-metastatic cancer. It has been identified that TARS polypeptides and TARS-encoding nucleic acids provide targets for treatments to enhance angiogenesis and for treatments in diseases and conditions that have an insufficient (e.g., less than desired) amount of angiogenesis and/or an insufficient (e.g., less than desired) immune system response. Thus, treatment to increase a reduced level of TARS, which may be a level of TARS polypeptide or level of TARS-encoding nucleic acid, for example, may increase angiogenesis and/or an immune system response in a cell, a tissue, and/or a subject. In some aspects, a treatment that increases TARS levels and/or function may increase angiogenesis or an immune system response in the treated subject. Further, by monitoring a subject undergoing a treatment of the invention and comparing changes in the level of a TARS polypeptide or TARS-encoding nucleic acid in the subject, one can evaluate changes in angiogenesis and/or an immune response in the subject and can assess the efficacy of a compound that is used to treat an angiogenic or immune disease or condition in the subject.

The present invention provides methods of treating a disease or condition associated with abnormal TARS activity. As used herein, the term "TARS activity" refers to a function of the TARS molecule, such as, but not limited to, aminoacylation of tRNA by threonine, association of a TARS polypeptide with a von Hippel Lindau (VHL) polypeptide to form a complex, association of a TARS polypeptide with elongation factor 1 (eEF1) to form a complex, associate of a TARS polypeptide with an E3 ubiquitin ligase, secretion of TARS protein or fragment of protein, binding of TARS to membrane receptors, or binding of TARS to extracellular matrix proteins.

In some embodiments of the invention, a disease or condition may be characterized by decreased TARS activity compared with a control level of TARS activity. It will be understood that an increase in TARS activity (e.g., resulting from a treatment of the invention) may be due to an increase in the amount of TARS expressed in a cell, tissue, or subject, an increase in the function or activity of TARS that is expressed in a cell, tissue, or subject, and/or an increase in the secretion of TARS by a cell, tissue, or subject. Thus, in some embodiments of the invention, an increase in TARS activity may be a result of an increase in the amount of TARS polypeptide in a cell, tissue, or fluid and in some embodiments the amount of TARS polypeptide may be unchanged (e.g., normal compared with a normal control) but the functional activity of the TARS that is present in the cell, tissue, or subject may be increased. The altered activity may the result of an increase in availability of a post-translationally modified version of TARS, which may be differentially secreted from one or more relevant cell types (including HUVEC cells, pre-vascular cells, angioblasts, endothelial cells, vascular cells, or cells of the innate immune system). It has been identified that altered TARS activity in cells and/or tissues is correlated with various diseases and conditions.

In certain diseases and conditions a level of TARS activity is statistically significantly lower in cells and/or tissues having the disease or condition compared to the level of TARS activity in cells and/or tissues that do not have the disease or condition. A level of TARS activity in a disease or condition characterized by a significantly lower activity compared to a normal control level may have a level of TARS activity that is less than 99%, 95%, 90%, 85%, 80%, 75%, 70%, 65%, 60%, 55%, 50%, 45%, 40%, 35%, 30%, 25%, 20%, 15%, 10%, 5%, or 1%, of a level in a normal control of TARS activity, e.g., a level in an equivalent sample that does not have a disorder or condition characterized by reduced, e.g., lower levels of TARS activity.

Examples of diseases and conditions that may be characterized by reduced TARS activity include, but are not limited to diseases or conditions such as is a tissue implant, organ implant, ischemia, cardiac infarction, tissue trauma, cartilage to bone transformation, stroke, surgery, pregnancy, macular degeneration, or vascular occlusion. In some aspects of the invention, assessing a change in the level of TARS activity in a disease or condition characterized by reduced (e.g., lower compared to a control) TARS activity may be desirable and methods of the invention may be used to monitor the level of TARS activity over time to assess changes. As used herein, a disease or condition that may be characterized by reduced TARS activity may also be referred to as a disease or condition associated with reduced TARS activity.

Treatment methods of the invention may include administering one or more compounds to a subject in need of such treatment, to increase a level of TARS in a cell or tissue sample to treat the disease or condition. Thus, in some aspects the invention includes methods of increasing angiogenesis and/or an immune system response in a cell, tissue or subject, wherein the method includes contacting the cells, tissues, or subject with an effective amount of a threonyl-tRNA synthetase (TARS) activity-enhancing compound to increase angiogenesis in the cell, tissue, or subject. As used herein, a TARS-activity-enhancing compound means a compound that increases TARS activity. A TARS activity-enhancing compound may increase TARS activity directly, e.g., by interacting directly with a TARS molecule, or may increase TARS activity indirectly, e.g., by modulating activity of another molecule that in turn is important in TARS activity. Examples of TARS-activity-enhancing compounds include, but are not limited to compounds such as a TARS polypeptide, a TARS-encoding nucleic acid, a small molecule TARS activity enhancer, a TARS-specific nucleic acid aptamer, etc.

Some aspects of the invention include contacting a cell with a TARS-activity-enhancing compound that increases an interaction of threonyl-tRNA synthetase (TARS) with VHL, or increases the effect of TARS on VHL function in the cell. The cell may be one of a plurality of cells. The contact with the TARS-activity-enhancing compound increases angiogenesis in the cell or plurality of cells. In some embodiments, the interaction of TARS with VHL comprises the formation, maintenance, or activity of a TARS/VHL complex. In some embodiments of the invention, increasing the interaction of the TARS/VHL complex comprises increasing the formation of a TARS/VHL complex in the plurality of cells. In certain embodiments, the increase in the formation of the TARS/VHL complex is sufficient to decrease an ubiquitination function of VHL on HIF-1α. In certain embodiments of the invention, increasing the interaction of the TARS/VHL complex comprises increasing the activity of a TARS/VHL complex in the plurality of cells. In some embodiments of the invention, increasing the interaction of the TARS/VHL complex comprises increasing the maintenance of a TARS/VHL complex in the plurality of cells. In some embodiments of the invention increasing the maintenance of the TARS/VHL complex activity comprises decreasing disassociation of the TARS/VHL complex. In certain embodiments of the invention, the plurality of cells is in a subject and is contacted with a TARS-activity-enhancing compound or a VHL-activity-enhancing compound that is administered to the subject. In the context of the present invention, a VHL-activity-enhancing compound may be a compound that indirectly enhances TARS activity, and thus may also be referred to as a TARS-activity-enhancing compound.

Identification of Candidate TARS-Activity-Enhancing Compounds

In some aspects of the invention, methods are provided to identify candidate compounds for treating an angiogenic or immune system disease or condition as are methods to determine the efficacy of a compound for the treatment of the disease or condition. Such methods may include, for example, determining one or more levels of TARS in a cell, tissue or subject and comparing the TARS secondary activity levels (e.g. including, but not limited to GTPase and Ap4A synthetic functions) in a cell, tissue, or subject contacted with the compound or treatment of the invention, with a cell, tissue, or subject not contacted with the compound or treatment of the invention.

A TARS level can be determined using methods of the invention to measure the amount and/or activity of a TARS molecule in an in vitro assay of a biological sample that has been obtained from the subject. As used herein, the term "measure" may refer to a determination of the presence or absence of a TARS molecule, may refer to a determination of a quantity a TARS molecule, or may refer to a determination of an activity level of a TARS molecule. Methods of measuring polypeptides or nucleic acids are known in the art, and non-limiting examples of measuring means are provided herein.

Detection methods suitable for use in methods of the present invention can be used to detect TARS polypeptide or nucleic acid molecules in a biological sample in vitro as well as in vivo. For example, in vitro techniques for detection of TARS mRNA include reverse transcriptase quantitative polymerase chain reaction (RT-qPCR), Northern hybridizations, in situ hybridizations, DNA or oligonucleotide array, and next generation sequencing. In vitro techniques for detection of TARS DNA include polymerase chain reaction (PCR) and Southern hybridizations. In vitro techniques for detection of TARS polypeptide include, but are not limited to enzyme linked immunosorbent assays (ELISAs), Western blots, immunoprecipitations and immunofluorescence, and other known suitable techniques. Alternatively, TARS polypeptide can be detected in vivo in a subject by introducing into the subject a labeled anti-TARS antibody. For example, the antibody can be labeled with a detectable marker such as a colorimetric marker, enzymatic marker, radioactive marker, etc. whose presence and location in a subject can be detected by standard imaging techniques.

Treatments to Increase TARS Activity

The invention in some aspects relates to methods for modulating angiogenesis or an immune response in a cell, tissue, and/or subject. As used herein the term "modulating" means changing a level of angiogenesis or the immune response. In some embodiments of the invention, changing angiogenesis includes changing a level of angiogenesis in a cell or tissue. As used herein, the term "modulating" used in reference to angiogenesis or an immune response using a treatment of the invention, means increasing angiogenesis or the immune response, respectively. Thus, methods of the invention may include, in some embodiments, treatments to increase angiogenesis and/or an immune response in a cell, tissue or subject. In some embodiments of the invention, angiogenesis and/or an immune system response may be increased by increasing the level and/or activity of a threonyl-tRNA synthetase (TARS) in the cell, tissue, and/or subject. In some embodiments of the invention methods may include increasing the level of a TARS polypeptide-encoding nucleic acid in a cell, tissue, or subject, which may result in increased activity of TARS in the cell, tissue, or subject. Certain embodiments of the invention methods may include directly increasing the level of TARS polypeptide in a cell, tissue, or subject, for example, by administering to a cell, tissue, or subject an effective amount of a small molecule TARS enhancing molecule, or TARS molecule such as a TARS polypeptide or fragment thereof, or a TARS-encoding nucleic acid molecule, etc. each of which increases TARS activity in a cell, tissue, and/or subject. Such methods may be used to treat a disease characterized by an abnormally low level of TARS activity that results in an undesirable level of angiogenesis and/or an immune system response.

In some aspects of the invention, a treatment includes administration of a TARS-activity-enhancing compound increases secreted TARS activity. As used herein, "secreted TARS activity" refers to activity of TARS outside its cell of origin. For example, in certain embodiments of treatment methods of the invention, a TARS-activity-enhancing compound is administered to a cell or subject and the compound increases TARS activity by increasing TARS secretion. In some embodiments of treatment methods of the invention, a TARS-activity-enhancing compound is administered to a cell or subject and the compound increases non-secreted TARS activity—for example, increases TARS activity within the cell in which it was produced.

Non-limiting examples of angiogenic diseases or conditions that may be treated with methods and compounds of the invention include, but are not limited to: is a tissue implant, organ implant, ischemia, cardiac infarction, tissue trauma, cartilage to bone transformation, stroke, surgery, pregnancy, macular degeneration, vascular occlusion, conditions for which it is desirable to have a stronger immune response such as in (a) some types of cancers; (b) viral infection, particularly HIV infected individuals with weakened immune systems; (b) bacterial or eukaryotic pathogen infection, etc. Examples of immune system diseases and conditions that may be treated with methods and compounds of the invention include, but are not limited to conditions such as infections, for example, by microbial agents; eukaryotic pathogens (for example, of fungal origin) or viral infections, non-limiting examples of which include infection by HIV-1 or other viruses that suppress the immune system.

As used herein, the terms "treat", "treated", or "treating" when used with respect to a disorder such as an angiogenic or immune system disease or condition that may be characterized by abnormal TARS polypeptide activity may refer to a prophylactic treatment that decreases the likelihood of a subject developing the angiogenic or immune system disease or condition, and also may refer to a treatment after the subject has developed the disease or condition in order to eliminate or reduce the level of the disease or condition, prevent the disease or condition from becoming more advanced (e.g., more severe), and/or slow the progression of the disease compared to in the absence of the therapy.

In certain embodiments of the invention, changing a TARS molecule activity may include increasing the activity of a TARS-encoding nucleic acid or increasing the activity of a TARS polypeptide in a cell, tissue, or subject. Thus, as used herein, a TARS molecule may refer to a TARS polypeptide or to a nucleic acid that encodes a TARS polypeptide.

In certain embodiments of the invention, changing TARS polypeptide activity includes increasing functioning of a TARS polypeptide in a cell, tissue, or subject. In some such embodiments, the level of the TARS polypeptide does not change, but the function of one or more of the TARS polypeptides in a cell may be altered, for example, increased. Examples of methods that may alter the function of a TARS polypeptide may include, but are not limited to contacting a cell, tissue, and/or subject with a TARS polypeptide or TARS-encoding nucleic acid that increases TARS function in the cell, tissue, and/or subject. For example, in some embodiments of the invention a TARS molecule may be delivered to a cell as part of a treatment regimen that increases TARS activity in the cell. In some embodiments of the invention, compounds that enhance TARS function may be administered to a cell or subject and result in a modulation of TARS polypeptide activity. Compounds that enhance a TARS polypeptide function and/or increase a TARS polypeptide level may be referred to herein as TARS-modulating compounds and TARS-activity-enhancing compounds. In some embodiments of the invention, a TARS-modulating compound may include a TARS polypeptide or functional fragment thereof, a small molecule TARS enhancer, a TARS polypeptide-encoding nucleic acid.

Compounds that increase a TARS polypeptide activity may be administered in an effective amount to a subject in need of treatment of an angiogenic or immune system disease or condition. Administering a compound that increases TARS polypeptide activity to a subject may reduce an angiogenic or immune system disease or condition in the subject.

TARS-Activity-Enhancing Compounds—Nucleic Acids and Polypeptides

A compound useful to treat an angiogenic or immune system disease or condition characterized by abnormal TARS polypeptide activity may, in some embodiments of the invention be a TARS polypeptide or nucleic acid that encodes a TARS polypeptide. A method of the invention may include administering an exogenous TARS polypeptide or exogenous TARS polypeptide-encoding nucleic acid to a subject. In some embodiments, the administered exogenous TARS polypeptide may be a full-length TARS polypeptide or may be a functional fragment of a full-length TARS polypeptide that has TARS function. In certain embodiments, the administered exogenous TARS polypeptide-encoding nucleic acid may produce a TARS polypeptide (full-length or fragment, or modified TARS polypeptide) that has TARS function.

TARS Nucleic Acid and Polypeptide Sequences and Variations (Variants)

One aspect of the invention involves isolated nucleic acid molecules that encode TARS polypeptides, TARS polypeptide variants, or biologically active portions thereof, as well as nucleic acid fragments sufficient for use to administer to a subject as a treatment or to assess candidate compound or efficacy of a treatment regimen of the invention. As used herein, the term "nucleic acid molecule" is intended to include DNA molecules (e.g., cDNA or genomic DNA) and RNA molecules (e.g., mRNA). A nucleic acid molecule may be single-stranded or double-stranded or may be a double-stranded DNA molecule. An "isolated" nucleic acid molecule is free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, may be free of other cellular material. As used herein A TARS molecule of the invention may be a TARS polypeptide or may be a TARS polypeptide-encoding nucleic acid.

In some aspects of the invention, an isolated nucleic acid molecule of the invention comprises the nucleotide sequence shown in GENBANK™ Accession No.: NM_152295 The sequence of GENBANK™ Accession No. NM_152295 corresponds to the human TARS cDNA. This cDNA comprises sequences encoding the TARS polypeptide (i.e., "the coding region", from nucleotides 1 to 2850), and 3' untranslated sequences (nucleotides 2468-2850). Alternatively, the nucleic acid molecule may comprise only the coding region of GENBANK™ Accession No NP_689508 (e.g., nucleotides 296-2467).

The invention further encompasses nucleic acid molecules that differ from the sequence set forth in GENBANK™ Accession No. NM_152295 (and portions thereof) due to degeneracy of the genetic code and thus encode the same TARS protein as that encoded by the sequence set forth in GENBANK™ Accession No. NM_152295. Accordingly, in another embodiment, an isolated nucleic acid molecule of the invention has a nucleotide sequence encoding a protein having an amino acid sequence as set forth in GENBANK™ Accession No. NM_152295. Moreover, the invention encompasses nucleic acid molecules that encode biologically active portions of the sequence set forth in GENBANK™ Accession No. NM_152295.

A nucleic acid molecule having the nucleotide sequence as set forth in GENBANK™ Accession No. NM_152295, or a portion thereof, can be isolated using standard molecular biology techniques and the sequence information provided herein. For example, a human TARS cDNA library using all or portion of the sequence set forth in GENBANK™ Accession No. NM_152295 as a hybridization probe and standard hybridization techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor, N.Y., 1989). Moreover, a nucleic acid molecule encompassing all or a portion of the sequence set forth as GENBANK™ Accession No.: NM_152295 can be isolated using any suitable method, including as a non-limiting example, use of the polymerase chain reaction using oligonucleotide primers designed based upon the sequence set forth as GENBANK™ Accession No.: NM_152295. For example, TARS mRNA can be isolated from cells using standard, art-known methods and cDNA can be prepared using reverse transcriptase and art-known methods. Synthetic oligonucleotide primers for PCR amplification can be designed based upon the nucleotide sequence set forth in GENBANK™ Accession No. NM_152295 and nucleic acids of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to TARS nucleotide sequence can be prepared by standard synthetic techniques, e.g., using an automated DNA synthesizer.

In addition to the human TARS nucleotide sequence set forth as GENBANK™ Accession No.: NM_152295, it will be appreciated by those skilled in the art that DNA sequence polymorphisms that lead to changes in the amino acid sequences of TARS may exist within a population (e.g., the human population). Such genetic polymorphism in the TARS gene may exist among individuals within a population due to natural allelic variation. Such natural allelic variations can typically result in 1-5% variance in the nucleotide sequence of a gene. Any and all such nucleotide variations and resulting amino acid polymorphisms in TARS that are the result of natural allelic variation and that do not alter the functional activity of TARS are intended to be within the scope of the invention. Moreover, nucleic acid molecules encoding TARS polypeptides from other species, and thus which have a nucleotide sequence that differs from the human sequence set forth as GENBANK™ Accession No.: NM_152295, are intended to be within the scope of the invention. Nucleic acid molecules corresponding to natural allelic variants and nonhuman homologues of the human TARS cDNA of the invention can be isolated based on their similarity or identity to the human TARS nucleic acid disclosed herein using the human cDNA, or a portion thereof, as a hybridization probe—according to standard hybridization techniques under stringent hybridization conditions, which are recognized in the art.

In some aspects of the invention, an isolated nucleic acid molecule of the invention that hybridizes under stringent conditions to the sequence set forth in GENBANK™ Accession No.: NM_152295 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human TARS polypeptide.

In addition to naturally-occurring allelic variants of the TARS sequence that may exist in the population, the skilled artisan will further appreciate that changes may be introduced by mutation into the nucleotide sequence set forth as GENBANK™ Accession No. NM_152295 thereby leading to changes in the amino acid sequence of the encoded TARS protein, without altering the functional ability of the TARS protein. For example, nucleotide substitutions leading to amino acid substitutions at "non-essential" amino acid residues may be made in the sequence set forth as GENBANK™ Accession No. NM_152295. A "non-essential" amino acid residue is a residue that can be altered from the wild-type sequence of TARS polypeptide (e.g., the sequence set forth as GENBANK™ Accession No. NM_152295)

without altering the activity of TARS, whereas an "essential" amino acid residue is required for TARS activity.

Accordingly, another aspect of the invention pertains to nucleic acid molecules encoding TARS polypeptides that contain changes in amino acid residues that are not essential for TARS activity, e.g., residues that are not conserved or only semi-conserved among members of the subfamily. Such TARS polypeptides differ in amino acid sequence from the sequence set forth as GENBANK™ Accession No. NM_152295 yet retain TARS activity. In one embodiment, the isolated nucleic acid molecule comprises a nucleotide sequence encoding a protein, wherein the protein comprises an amino acid sequence with at least 70%, 75%, 80%, 85%, 90%, 95%, 97%, or at least 99%, identity to the amino acid sequence set forth as GENBANK™ Accession No.: NM_152295 and retains a level of TARS activity. In some aspects of the invention, a TARS polypeptide with full or partial TARS function may be administered to a subject or cell, to increase TARS activity in the subject or cell respectively.

To determine the percent identify of two amino acid sequences (e.g., GENBANK™ Accession No. NM_152295 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., GENBANK™ Accession No. NM_152295) is occupied by the same amino acid residue as the corresponding position in the other sequence (e.g., a mutant form of TARS), then the molecules have identity or similarity at that position. The percent identity between the two sequences is a function of the number of identical positions shared by the sequences (i.e., % identity=number of identical positions/total number of positions×100). Such an alignment can be performed using any one of a number of well-known computer algorithms designed and used in the art for such a purpose.

An isolated nucleic acid molecule encoding a TARS polypeptide having a percent identity or percent similarity to the protein of GENBANK™ Accession No.: NM_152295 can be created by introducing one or more nucleotide substitutions, additions or deletions into the nucleotide sequence of GENBANK™ Accession No.: NM_152295 such that one or more amino acid substitutions, additions or deletions are introduced into the encoded polypeptide. Mutations can be introduced into the sequence set forth as GENBANK™ Accession No. NM_152295 by standard techniques, such as site-directed mutagenesis and PCR-mediated mutagenesis. In some embodiments of the invention conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in TARS may be replaced with another amino acid residue from the same side chain family. Alternatively, in another embodiment, mutations can be introduced randomly along all or part of a TARS coding sequence, such as by saturation mutagenesis, and the resultant mutants can be screened for TARS activity to identify mutants that retain TARS activity. Following mutagenesis of a sequence such as that set forth as GENBANK™ Accession No. NM_152295, the encoded protein can be expressed recombinantly and the TARS activity of the polypeptide can be determined, for example using an assay described herein or other suitable assay.

As used herein a TARS molecule of the invention may be a TARS polypeptide or may be a TARS polypeptide-encoding nucleic acid. A variant of a TARS molecule may be a TARS polypeptide that differs from SEQ ID NO:2 by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or more amino acids. A variant of a TARS molecule may be a TARS polypeptide-encoding nucleic acid that differs from SEQ ID NO:1 by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, or more nucleotides. The term "differ" when used in the context of a TARS polypeptide or TARS polypeptide-encoding nucleic acid means that a TARS polypeptide may be shorter or longer or have a sequence that is not identical to that of SEQ ID NO:2. Similarly, a TARS polypeptide-encoding nucleic acid may be shorter or longer or have a nucleotide sequence that is not identical to that of SEQ ID NO:1. A TARS polypeptide variant or a TARS polypeptide-encoding nucleic acid variant may be a functional TARS polypeptide or a functional TARS polypeptide-encoding nucleic acid variant, respectively. A functional TARS polypeptide encoding nucleic acid variant and a TARS polypeptide variant will retain at least partial function of a TARS molecule set forth as SEQ ID NO:1 or SEQ ID NO:2, respectively.

As used herein, the terms "protein" and "polypeptide" are used interchangeably and thus the term polypeptide may be used to refer to a full-length protein and may also be used to refer to a fragment of a full-length protein. As used herein with respect to polypeptides, proteins, or fragments thereof, and nucleic acids that encode such polypeptides the term "exogenous" means the compound is administered to a cell or subject and was not naturally present in the cell or subject. It will be understood that an exogenous TARS polypeptide or TARS polypeptide-encoding nucleic acid may be identical to, or different from, an endogenous TARS polypeptide or TARS polypeptide-encoding nucleic acid, respectively, in terms of its sequence, but was administered to the cell or subject.

According to some aspects of the invention, full-length TARS polypeptides or fragments of full-length TARS polypeptide may be administered in methods of the invention. Fragments of the invention may be fragments that retain a distinct functional capability of the polypeptide. Functional capabilities that can be retained in a fragment include interaction with antibodies, and interaction with other polypeptides or fragments thereof. Polypeptide fragments may be natural fragments or may be synthesized using art-known methods, and tested for function using the methods exemplified herein. Full-length TARS and functional fragments of TARS polypeptides that are useful in methods and compositions of the invention may be recombinant polypeptides.

A fragment of a full-length TARS polypeptide may comprise at least 1, 2, 3, 4, 5, 6, 7, 8, 9, 10, 11, 12, 13, 14, 15, 16, 17, 18, 19, 20, 25, 30, 35, or 50 amino acids fewer of the contiguous amino acids of TARS polypeptide having a consecutive sequence found in a wild-type TARS polypeptide or in a modified TARS polypeptide sequence as described herein. Such TARS polypeptides that are fragments of full-length TARS polypeptide may be useful for a variety of purposes, including for administration as TARS-modulating compounds and for preparing TARS-modulating compounds such as antibodies that bind specifically to synthetic and natural TARS polypeptides.

A "modified" wild-type or mutant full-length TARS polypeptide or polypeptide that is a fragment thereof may include deletions, point mutations, truncations, amino acid substitutions and/or additions of amino acids or non-amino acid moieties. Modifications of a polypeptide of the invention may be made by modification of the nucleic acid that encodes the polypeptide or alternatively, modifications may be made directly to the polypeptide, such as by cleavage, addition of a linker molecule, addition of a detectable moiety, such as a fluorescent label, and the like. Modifications also embrace fusion proteins comprising all or part of the polypeptide's amino acid sequence.

In some embodiments of the invention modified polypeptides (e.g. modified TARS wild-type or mutant polypeptides) may include polypeptides that are modified specifically to alter a feature of the polypeptide related or unrelated to its physiological activity. TARS polypeptides can be synthesized with modifications and/or modifications can be made in a TARS polypeptide by selecting and introducing an amino acid substitution, deletion, or addition. Modified polypeptides then can be tested for one or more activities (e.g., modulating TARS-polypeptide activity in a cell or subject, treatment of an angiogenic or immune system disease or condition, etc., to determine which modification provides a modified polypeptide with the desired properties.

The skilled artisan will also realize that conservative amino acid substitutions may be made in a polypeptide to provide functionally equivalent polypeptides, i.e., a modified TARS polypeptide that retains a functional capability of an un-modified TARS polypeptide in a treatment method of the invention. As used herein, a "conservative amino acid substitution" refers to an amino acid substitution that does not alter the relative charge or size characteristics of the polypeptide in which the amino acid substitution is made. Modified TARS polypeptides can be prepared according to methods for altering polypeptide sequence and known to one of ordinary skill in the art such. Exemplary functionally equivalent TARS polypeptides include conservative amino acid substitutions of a TARS polypeptide, or fragments thereof, such as a modified TARS polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in a TARS polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis, or by chemical synthesis of a gene encoding the TARS polypeptide. Where amino acid substitutions are made to a small fragment of a polypeptide, the substitutions can be made by directly synthesizing the polypeptide. The activity of functionally equivalent fragments of TARS polypeptides can be tested by cloning the gene encoding the altered polypeptide into a bacterial or mammalian expression vector, introducing the vector into an appropriate host cell, expressing the altered polypeptide, and testing for a functional capability of the polypeptide as disclosed herein.

In some embodiments of the invention, a level or function of a TARS polypeptide in a cell, tissue, and/or subject may be modulated by genetically introducing a TARS polypeptide into a cell, tissue, and/or subject and reagents and methods are provided for genetically targeted expression of TARS polypeptides. Genetic targeting can be used to deliver TARS or other therapeutic polypeptides to specific cell types, to specific cell subtypes, to specific spatial regions within an organism, and to sub-cellular regions within a cell. Genetic targeting also relates to the control of the amount of a TARS polypeptide expressed, and the timing of the expression. Some embodiments of the invention include a reagent for genetically targeted expression of a TARS polypeptide, wherein the reagent comprises a vector that contains a nucleic acid that encodes a TARS polypeptide or encodes a functional fragment of a TARS polypeptide.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert TARS polypeptides into dividing and non-dividing cells and can insert TARS polypeptides to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. In certain embodiments of the invention, a vector may be a lentivirus comprising a nucleic acid or gene that encodes a TARS polypeptide of the invention or a variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of an TARS polypeptide in a wide variety of cell types—thus a promoter for a gene that is widely expressed in a variety of cell types, for example a "housekeeping gene" can be used to express a TARS polypeptide in a variety of cell types. Non-limiting examples of general promoters are provided elsewhere herein and suitable alternative promoters are well known in the art. In certain embodiments of the invention, a promoter may be an inducible promoter, examples of which include, but are not limited to tetracycline-on or tetracycline-off, etc.

Certain aspects of the invention include methods of administering a TARS molecule such as a TARS polypeptide or functional fragment thereof, or a TARS-encoding nucleic acid, etc., to treat an angiogenic or immune system disease or condition characterized by abnormally low TARS polypeptide activity. In some embodiments of the invention such antibodies or antigen-binding fragments thereof may be administered to a cell and/or subject to enhance TARS polypeptide activity in the cell and/or subject.

Additional TARS-Activity-Enhancing Compounds

Additional compounds that may be administered in treatment methods of the invention include small molecules or chemicals that enhance TARS polypeptide activity. Methods of identifying and testing such small molecules and chemicals may include use of art-known library screening and testing procedures in conjunction with the teaching provided herein.

It will be understood that in addition to compounds set forth herein, additional TARS-modulating compounds can be identified and used in methods of the invention. For example, candidate compounds can be can be tested for their ability to increase TARS polypeptide activity (level and/or function) and their ability to treat an angiogenic or immune system disease or condition using assays and methods presented herein.

TARS-Activity-Enhancing Compound Administration

TARS polypeptide modulating compounds of the invention may be administered singly or in combination with one or more additional compounds. In some embodiments, a compound of the invention may act in a synergistic manner with one or more other therapeutic agents or treatments and increase the effectiveness of the one or more therapeutic agents or activities, thus a TARS enhancer compound may act synergistically to increase the effectiveness of one or more agents or treatments that can be administered to treat an angiogenic or immune system disease or condition.

Compositions, compounds, and methods of the invention may be enhanced by utilization in combination with other procedures for treating an angiogenic or immune system disease or condition. In some instances a treatment procedure may involve administration of another therapeutic agent or treatment such a medicament and/or a behavioral treatment, surgery, etc. Thus, in some embodiments of the invention, administration of a compound of the invention (e.g., administration of a TARS polypeptide-encoding nucleic acid, TARS polypeptide (or functional fragment thereof), or a small molecule TARS enhancer, etc.) may be performed in conjunction with therapies for treating the angiogenic or immune system disease or condition such as surgery, etc. Treatment methods of the invention that include administration of a TARS-modulating compound can be used at any stages of pre-angiogenic or pre-immune system disease or condition or when the angiogenic or immune system disease or condition is at a later stage, including but not limited to early-stage, mid-stage, and late-stage of the angiogenic or immune system disease or condition, including all times before and after any of these stages. Methods of the invention may also be used for subjects who have previously been treated with one or more other medicaments or therapy methods that were not successful, were minimally successful, and/or are no longer successful at slowing or stopping progression of the angiogenic or immune system disease or disorder in the subject.

TARS-modulating compounds of the invention (such as compounds comprising a functional TARS molecule, a small molecule TARS enhancer, etc.) described herein can be used alone or in conjugates with other molecules such as targeting agents, labeling agents, and/or cytotoxic agents in treatment methods of the invention.

Targeting agents useful according to the methods of the invention are those that direct a compound of the invention to a specific cell type, an example of which, though not intended to be limiting are cells of the immune system, for example, a Th17 cell. A targeting compound of choice will depend upon the nature of the angiogenesis-associated disease or condition. In some instances it may be desirable to target the agent to skeletal muscle, cardiac muscle, kidney, liver, brain, implanted tissue, transplanted tissue, etc. Those of ordinary skill in the art will be aware of and able to select and use suitable targeting agents for use in methods of the invention.

Labeling agents may be used in methods of the invention to determine the location of TARS polypeptides in cells and tissues and also, may be used to assess the cell, tissue, or organelle location of treatment compounds that have been administered. Procedures for attaching and utilizing labeling agents such as enzymatic labels, dyes, radiolabels, etc. are well known in the art.

Effective Amounts for Treatments

TARS-modulating compounds of the invention, (e.g., a TARS polypeptide-encoding nucleic acid, TARS polypeptide, or a small molecule TARS enhancer, etc.) are administered to the subject in an effective amount for treating the angiogenic or immune system disease or condition. An "effective amount for treating an angiogenic or immune system disease or condition is an amount necessary or sufficient to realize a desired biologic effect. For example, an effective amount of a compound of the invention could be that amount necessary to (i) slow or halt progression of the disease or condition; or (ii) reverse one or more symptoms of the angiogenic or immune system disease or condition. According to some aspects of the invention, an effective amount is that amount of a compound of the invention alone or in combination with another medicament or treatment, which when combined or co-administered or administered alone, results in a therapeutic response in the angiogenic or immune system disease or condition, either in the prevention or the treatment of the angiogenic or immune system disease or condition. The biological effect may be the amelioration and or absolute elimination of symptoms resulting from the angiogenesis-associated disease or condition. In another embodiment, the biological effect is the complete abrogation of the angiogenic or immune system disease or condition, as evidenced for example, by a diagnostic test that indicates the subject is free of the disease or condition.

Typically an effective amount of a compound or drug to increase the function or level of a TARS polypeptide will be determined in clinical trials, establishing an effective dose for a test population versus a control population in a blind study. In some embodiments, an effective amount will be that results in a desired response, e.g., an amount that diminishes one or more symptoms of an angiogenic or immune system disease or condition in cells or tissues in a subject with the angiogenic or immune system disease or condition. Thus, an effective amount to treat an angiogenic or immune system disease or condition characterized by a decreased TARS polypeptide activity may be the amount that when administered increases the amount of TARS polypeptide activity in the subject, cell or tissue to an amount that that is above the amount that would occur in the subject, cell, or tissue, respectively without the administration of the composition. In the case of treating an angiogenic or immune system disease or condition the desired response may be reducing or eliminating one or more symptoms of the disease or condition in the cell, tissue, and/or subject. The reduction or elimination may be temporary or may be permanent. The status of the disease or condition can be monitored using methods of determining TARS polypeptide activity or levels of nucleic acids that encode a TARS polypeptide, etc. In some aspects of the invention, a desired response to treatment of the angiogenic or immune system disease or condition also can be delaying the onset or even preventing the onset of the angiogenic or immune system disease or condition.

An effective amount of a compound that modulates (e.g., increases) TARS polypeptide activity (also referred to herein as a pharmaceutical compound) may also be determined by assessing physiological effects of administration on a cell or subject, such as a decrease of an angiogenic or immune system disease or condition following administration. Assays suitable to determine efficacy of a pharmaceutical compound of the invention will be known to those skilled in the art and can be employed for measuring the level of the response to a treatment and an amount of a pharmaceutical compound administered to a subject can be modified based, at least in part, on such measurements. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner. For example, an effective amount may depend upon the degree to which an individual has abnormally low levels of TARS polypeptide activity.

The effective amount of a compound of the invention in the treatment of an angiogenic or immune system disease or condition or in the reduction of the risk of developing an angiogenic or immune system disease or condition may vary depending upon the specific compound used, the mode of delivery of the compound, and whether it is used alone or in combination. The effective amount for any particular application can also vary depending on such factors as the angiogenic or immune system disease or condition being treated, the particular compound being administered, the size of the subject, or the severity of the disease or condition. A skilled artisan can empirically determine the effective amount of a particular compound of the invention without necessitating undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular subject.

A pharmaceutical compound dosage may be adjusted by an individual health care provider or veterinarian, particularly in the event of any complication. A therapeutically effective amount typically varies from 0.01 mg/kg to about 1000 mg/kg, from about 0.1 mg/kg to about 200 mg/kg, or from about 0.2 mg/kg to about 20 mg/kg, in one or more dose administrations daily, for one or more days. The absolute amount will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g., a TARS polypeptide-encoding nucleic acid, TARS polypeptide, or a small molecule TARS enhancer, etc.) can be administered at least daily, every other day, weekly, every other week, monthly, etc. Doses may be administered once per day or more than once per day, for example, 2, 3, 4, 5, or more times in one 24 hour period.

Pharmaceutical compounds of the invention may be administered alone, in combination with each other, and/or in combination with other drug therapies, or other treatment regimens that are administered to subjects with an angiogenic or immune system disease or condition. Pharmaceutical compositions used in the foregoing methods preferably are sterile and contain an effective amount of a therapeutic compound that will modulate a TARS polypeptide activity to a level sufficient to produce the desired response in a unit of weight or volume suitable for administration to a subject.

The doses of a composition to modulate the TARS polypeptide activity that is administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Administration Methods

A variety of administration routes for a TARS-modulating compound are available. The particular delivery mode selected will depend, of course, upon the particular condition being treated and the dosage required for therapeutic efficacy. Methods of this invention, generally speaking, may be practiced using any mode of administration that is medically acceptable, meaning any mode that produces effective levels of protection without causing clinically unacceptable adverse effects. In some embodiments of the invention, a compound of the invention may be administered via an oral, enteral, mucosal, percutaneous, and/or parenteral route. The term "parenteral" includes subcutaneous, intravenous, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, a compound of the invention may be placed within a slow release matrix and administered by placement of the matrix in the subject. In some aspects of the invention, a compound (such as a TARS polypeptide-encoding nucleic acid, TARS polypeptide, or a small molecule TARS or enhancer, etc.) may be delivered to a subject cell using nanoparticles coated with a delivery agent that targets a specific cell or tissue.

Compounds of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a pharmaceutical composition. In general, a pharmaceutical composition comprises the compound of the invention and a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the compound such as a TARS polypeptide-encoding nucleic acid, TARS polypeptide, or a small molecule TARS enhancer, etc. to treat the angiogenic or immune system disease or condition.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Compounds of the invention may be administered directly to a tissue. In some embodiments, the tissue to which the compound is administered is a tissue in which the angiogenic or immune system disease or condition is likely to arise. Direct tissue administration may be achieved by direct injection. Compounds may be administered once, or alternatively they may be administered in a plurality of administrations. If administered multiple times, the compounds may be administered via different routes. For example, the first (or the first few) administrations may be made directly into the affected tissue while later administrations may be systemic.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain formulatory agents such as suspending, stabilizing and/or dispersing agents.

Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of compounds.

In yet other embodiments, a delivery vehicle is a biocompatible microparticle or implant that is suitable for implantation into the mammalian recipient. Exemplary bioerodible implants that are useful in accordance with this method are described in PCT Publication No. WO 95/24929 (incorporated by reference herein), which describes a biocompatible, biodegradable polymeric matrix for containing a biological macromolecule. Such delivery means are well known in the art and can be used to achieve sustained release of a compound of the invention in a subject, and may be selected not to degrade, but rather, to release by diffusion over an extended period of time.

Both non-biodegradable and biodegradable polymeric matrices can be used to deliver the compounds of the invention to the subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, compounds of the invention may be delivered using the bioerodible implant by way of diffusion, or by degradation of the polymeric matrix. Exemplary synthetic polymers for such use are well known in the art. Biodegradable polymers and non-biodegradable polymers can be used for delivery of compounds of the invention using art-known methods. Bioadhesive polymers such as bioerodible hydrogels (see H. S. Sawhney, C. P. Pathak and J. A. Hubell in Macromolecules, 1993, 26, 581-587, the teachings of which are incorporated herein) may also be used to deliver compounds of the invention for treatment. Additional suitable delivery systems can include time-release, delayed release or sustained release delivery systems. Such systems can avoid repeated administrations of the compound, increasing convenience to the subject and the physician. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be particularly suitable for prophylactic treatment of subjects and for subjects at risk of developing a recurrent angiogenic or immune system disease or condition. Long-term release, as used herein, means that the implant is constructed and arranged to delivery therapeutic levels of the active ingredient for at least 30 days, 60 days, 90 days or longer. Long-term sustained release implants are well-known to those of ordinary skill in the art and include some of the release systems described above.

Therapeutic formulations of compounds of the invention may be prepared for storage by mixing the compound having the desired degree of purity with optional pharmaceutically acceptable carriers, excipients or stabilizers [Remington's Pharmaceutical Sciences 21$^{st}$ edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

In Vivo Imaging Techniques

A molecule used in a treatment method of the invention, (e.g., a TARS polypeptide or fragment thereof, a small molecule that binds to TARS or to TARS in association with another polypeptide, etc.—(also referred to herein as "a therapeutic molecule of the invention") may also be used for imaging purposes, for example, to detect location of the treatment activity. Suitable labels that may be attached to a treatment molecule and used in methods of the invention include, but are not limited to, radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin, and nano- or microparticles.

In some embodiments a therapeutic molecule (e.g., a TARS polypeptide, etc.) used for a treatment method of the invention may be labelled, or otherwise modified, to permit detection. Such labeled treatment molecules can be used for real-time in vivo imaging using sample that remains within (e.g., is not removed from) a subject or for in vitro imaging using a sample that is removed from a subject. Detectable labels that can be used in conjunction with a therapeutic molecule of the invention may be any that do not substantially interfere with the therapeutic molecule function to treat the angiogenic or immune system disease or condition, but that allow external detection. Examples of detectable labels and methods suitable for use in in vitro treatment methods of the invention are described in detail elsewhere herein. Suitable in vivo detectable labels may include those that may be detected by X-radiography, NMR or MRI. For X-radiographic techniques, suitable detectable labels include any radioisotope that emits detectable radiation but that is not overtly harmful to the patient, such as barium or cesium, for example. Suitable detectable labels for NMR and MRI generally include those with a detectable characteristic spin, such as deuterium, which may be incorporated into the antibody by suitable labeling of nutrients for the relevant hybridoma, in the case of an antibody, for example.

The size of the subject, and the imaging system used, will determine the quantity of imaging moiety needed to produce in vivo images. In the case of a radioisotope moiety, for a human subject, the quantity of radioactivity injected will normally range from about 5 to 20 millicuries of technetium-99m. The labeled therapeutic molecule (for example, labeled antibody or antibody fragment thereof or other TARS molecule) will then preferentially accumulate at the location of sample cells that contain TARS. The labeled therapeutic molecule can then be detected using known techniques.

Assessing Treatments of TARS-Associated Diseases and Conditions

In some aspects of the invention methods are provided that include comparing a level of TARS determined or measured a sample obtained from a subject to a control value for determining the efficacy of a treatment of the invention. In addition, the effectiveness of a treatment of the invention can be assessed by measuring TARS levels in samples obtained from a subject. Thus, methods of the invention, in some aspects include, assessing the onset, progression, or regression of an angiogenic or immune system disease or condition that is characterized by decreased TARS activity, by measuring TARS levels in samples obtained from or tested in the subject at two, three, four, five, or more different times, e.g., before, during and after a treatment regimen of the invention. Thus, for example, in a method that utilizes two or more samples obtained from a subject at different times, values obtained from a sample obtained at one time can be compared to values obtained at other times as a measure of the efficacy of a treatment of the invention. For example, a first level obtained from the subject may serve as a baseline level or control level for that subject, thus allowing comparison of the TARS level and the determination of change or stability of the TARS level over time and across a treatment regimen. Thus, in some aspects of the invention TARS levels may be measured after a specific course of treatment for an angiogenic or immune system disease or condition has been initiated, with the intent of determining the efficacy of that treatment or the onset of relapse as a consequence of resistance to the treatment.

The status of the angiogenic or immune system disease or condition can be monitored using methods of determining TARS polypeptide activity or levels of nucleic acids that encode a TARS polypeptide, etc. In some aspects of the invention, a desired response to treatment of the angiogenic or immune system disease or condition also can be delaying the onset or even preventing the onset of the angiogenic or immune system disease or condition.

The invention, in some aspects, includes methods and assays (e.g. binding assays, gel electrophoresis; mass spectrometry; NMR; etc.) to determine changes in TARS level and/or activity in a subject or cell sample (e.g., cell culture) over time. This allows monitoring of TARS levels and/or activity in a subject who is to undergo a treatment of the invention for an angiogenic or immune system disease or condition and also enables to monitoring in a subject who is currently undergoing therapy for the angiogenic or immune system disease or condition. Thus, methods of the invention may be used to treat an angiogenic or immune system disease or condition in a subject and may also be used to assess the efficacy of a therapeutic treatment of the disease or condition and for assessment of the activity or level of a TARS molecule in a subject at various time points. For example, a subject's TARS level and/or activity can be determined prior to the start of a therapeutic regimen (either prophylactic or as a treatment of an angiogenic or immune system disease or condition), during the treatment regimen and/or after a treatment regimen, thus providing information on the status of the angiogenic or immune system disease or condition in the subject.

Methods of Detection

Thus, in addition to the treatment methods of the invention, in some aspects, the invention includes detection methods useful for assessing treatment methods and for identifying candidate compounds for use in treatment methods of the invention. Detection methods may permit detecting the presence of a TARS molecule in a biological sample. The methods may comprise contacting the biological sample with an agent capable of detecting TARS polypeptide or nucleic acid molecules (e.g., TARS mRNA or DNA, etc.) such that the presence of TARS is detected in the biological sample. An agent for detecting TARS mRNA using methods of the invention may be a labeled or labelable nucleic acid probe capable of hybridizing to TARS mRNA. The nucleic acid probe may be, for example, the full-length TARS cDNA of GENBANK™ Accession No. NM_152295 or a portion thereof, such as an oligonucleotide of at least 15, 30, 50, 100, 250 or 500 nucleotides in length and sufficient to specifically hybridize under stringent conditions to TARS mRNA.

Detection methods useful in methods of the invention, including but not limited to those described above herein can be used to monitor efficacy of a treatment that is administered to a subject. In some embodiments of the invention, methods include contacting a biological sample obtained from the subject (or isolate of the sample) who has undergone a treatment of the invention, with an agent capable of detecting TARS polypeptide or nucleic acid such that the presence and/or level of TARS polypeptide or nucleic acid is detected in the biological sample or isolate, thereby permitting the practitioner to assess the efficacy of the treatment. In certain embodiments, methods of the present invention may include comparing the level of TARs polypeptide or nucleic acid in a sample or isolate with the level of TARS polypeptide or nucleic acid in a control sample. A control sample may be a sample from the subject prior to, or at an earlier stage of the subject's treatment and a difference in the TARS activity in the subsequent sample can indicate whether there has been a change in the status of the disease or condition in response to the treatment of the invention. For example, if a treatment of the invention results in an increase in TARS activity that is detected in a follow up assessment, it is an indication of the efficacy of the treatment to treat the angiogenic or immune system disease or condition. Such a determination of the efficacy of the treatment can also include a step of determining an appropriate treatment for a subject by a health-care provided based at least in part on the determination of the TARS level in a sample from the subject and the efficacy of the treatment the subject has received.

In some embodiments of the invention, a control level of TARS activity is a level determined from cells that do not have the disease or condition associated with altered TARS activity that is being tested for in the subject's sample. For example, in some embodiments, a control level of TARS is a level determined in normal cells that do not have an angiogenic or immune disease or condition that is suspected to be in the biological sample obtained from the subject. In such a case, the efficacy of the treatment of a compound or treatment of the invention can be determined based on an increase in the TARS activity in the subject's sample as compared to the control that is free of the disease or condition.

Thus, some aspects of the invention include methods of assisting a health care provider to select a treatment to enhance angiogenesis or the immune system in a subject in need of such treatment. In some embodiments of the invention, such methods may include obtaining a cell sample from a subject having or at risk of having an angiogenic or immune system disease or condition, determining the threonyl-tRNA synthetase (TARS)/von Hippel Lindau factor (VHL) interaction in the cell sample; comparing the determined TARS/VHL interaction to a control TARS/VHL interaction, and selecting a treatment for the angiogenic or immune system disease or condition in the subject based at least in part on the difference between the determined TARS/VHL interaction and the control TARS/VHL interaction, wherein if the determined TARS/VHL interaction is less than the control interaction, the selected treatment is a treatment that enhances the TARS/VHL interaction in the subject and increases angiogenesis and/or enhances the immune system in the subject. The interaction of TARS with VHL may include the formation, maintenance, or activity of a TARS/VHL complex, and increasing the interaction of the TARS/VHL complex may include: 1) increasing the formation of a TARS/VHL complex in the subject; 2) increasing the activity of a TARS/VHL complex in the subject; 3) increasing the maintenance of a TARS/VHL complex in the subject. In some embodiments increasing the maintenance of the TARS/VHL complex activity comprises decreasing disassociation of the TARS/VHL complex. A control value for a TARS/VHL interaction may be a predetermined standard TARS/VHL, which may be a normal control or a disease control. In certain embodiments of the invention, methods of selecting a treatment may include determining the level of the TARS/VHL complex in a tissue sample from a subject, comparing the level of the TARS/VHL complex with a control level of TARS/VHL complex and basing the selection at least in part on the comparison; comparing the level of HIF-1α in the subject to a control level of HIF-1α and basing the selection at least in part on the comparison; comparing the level of ubiquitination of HIF-1α in the subject to a control level of ubiquitination and basing the selection at least in part on the comparison; or comparing the level of vascular endothelial growth factor (VEGF) in the subject to a control level of VEGF and basing the selection at least in part on the comparison. A treatment of the angiogenic or immune system disease or condition may include administering to the subject an effective amount of a TARS-activity-enhancing compound to increase angiogenesis and/or the immune system response in the subject.

Identifying Candidate Compounds

The invention, in some aspects also includes methods to identify candidate compounds that increase TARS activity when administered to a cell, tissue, or subject, and methods to assess the efficacy of candidate TARS-modulating compounds to increase expression of TARS polypeptide-encoding nucleic acid or a TARS polypeptide in a cell or tissue. Such methods may be carried out in vivo in human or animal subjects; or using in vitro assays of the invention such as in cells from culture—e.g., as screening assays to assess candidate TARS-modulating compounds to modulate TARS polypeptide activity. TARS-modulating compounds that alter TARS polypeptide activity in a cell, tissue, or subject may be used in the treatment of an angiogenic or immune system disease or condition or as a pretreatment for an angiogenic or immune system disease or condition (e.g., to prepare a cell or subject for subsequent treatment).

It will be understood that a therapeutic regimen may be either prophylactic or a treatment of an angiogenic or immune system disease or condition in a subject. The invention in some aspects provides methods that may be used to monitor a subject's response to prophylactic therapy and/or treatment for an angiogenic or immune system disease or condition provided to a subject. Methods of the invention (e.g. binding assays, gel electrophoresis; mass spectrometry; NMR; etc.) may also be useful to monitor the efficacy of a treatment of the invention. TARS polypeptide levels and/or activity or TARS-encoding nucleic acid levels may be determined in two, three, four, or more biological samples obtained from a subject at separate times. The TARS polypeptide levels and/or activity or the TARS-encoding nucleic acid levels determined in the samples may be compared and changes in the levels and/or activity over time may be used to assess the status and stage of an angiogenic or immune system disease or condition in the subject (or in a cell or tissue sample) and/or the effect of a treatment strategy on the angiogenic or immune system disease or condition in a subject (or a cell or tissue sample). Some embodiments of methods of the invention can be used to assess treatments for an angiogenic or immune system disease or conditions and can be used to select a therapy for the subject, for example, to select a drug therapy, behavioral therapy, surgical therapy, etc.

Assays for assessing TARS levels in embodiments of the invention may include determining one or more TARS levels and/or activities, including but not limited to determining levels of nucleic acids that encode TARS polypeptides and/determining levels of TARS polypeptides in cells, tissues, and subjects. Levels of TARS polypeptide-encoding nucleic acids and TARS polypeptides can be determined in a number of ways when carrying out the various methods of the invention. In some embodiments of the invention, a level of a TARS polypeptide-encoding nucleic acid or TARS polypeptide is measured in relation to a control level of TARS polypeptide-encoding nucleic acid or TARS polypeptide, respectively, in a cell, tissue, or subject. One possible measurement of the level of TARS polypeptide-encoding nucleic acid or polypeptide is a measurement of an absolute level of TARS polypeptide-encoding nucleic acid or TARS polypeptide. This could be expressed, for example, in the level of TARS polypeptide-encoding nucleic acid or polypeptide per unit of cells or tissue. Another measurement of a level of TARS polypeptide-encoding nucleic acid or TARS polypeptide is a measurement of the change in the level of the TARS polypeptide-encoding nucleic acid or TARS polypeptide over time. This may be expressed in an absolute amount or may be expressed in terms of a percentage increase or decrease over time. Antibodies or antigen-binding fragments or other compounds that specifically bind a TARS polypeptide or a nucleic acid that encodes a TARS polypeptide may be used in embodiments of methods of the invention to assess TARS polypeptide and TARS polypeptide-encoding nucleic acid molecules to assess the status of an angiogenic or immune system disease or condition and/or the efficacy of treatments for an angiogenic or immune system disease or condition.

In some aspects, the invention includes methods that provide information on the efficacy of a method of the invention used to treat an angiogenic or immune system disease or condition. In certain aspects, the invention includes to assess activity and efficacy of compounds administered in treatment methods of the invention. Information about the stage or status of a disease or condition and the efficacy of a compound or treatment of the invention can be used to assist a health-care provided to select a treatment for administration to the subject or can be used by a health-care professional to adjust (e.g., increase, decrease, or stop) a treatment that is being provided to the subject.

As used herein a "subject" refers to any warm-blooded animal, such as, but not limited to a human, a non-human primate, a rodent, a dog, cat, or other animal. Thus, in addition to human medical application, some aspects of the invention include veterinary application of methods described herein. A subject may be known to have a disease or condition characterized by an altered TARS activity as compared to a control level, and thus may be a subject diagnosed with the disease or condition. In some embodiments, a subject may not have been previously or currently diagnosed with such a disease or condition, but may be considered to be at risk of for having the disease or condition, for example, a subject who may be free of a detectable disease or condition in which TARS activity is altered. In some embodiments of the invention, a subject may have previously been diagnosed with a disease, for example diagnosed with an angiogenic disease or condition, or immune system disease or condition but the subject may be in remission at the time a treatment is performed using methods of the invention.

In some embodiments of the invention, a biological sample comprises a cell or tissue or extracellular material from a subject. A tissue sample or tumor sample may comprise tissue or a suspension of cells. A tissue section, for example, a freeze-dried, paraffin embedded, or fresh frozen section of tissue removed from a subject. Moreover, a biological sample may be a biological fluid obtained from a subject (e.g., blood, aqueous humour and vitreous humour, bile, blood, serum, breast milk, cerebrospinal fluid, lymph, female or male ejaculate, gastric fluid, mucus, peritoneal fluid, plural fluid, saliva, sebum, semen, sweat, tears, vaginal secretion, urine, ascites, spinal fluid, etc.).

In some aspects of the invention, a biological sample includes one or more pre-vascular cells, angioblasts, vascular cells, immune cells, including T cells; fibroblasts; neuronal cells, glial cells, cells of the lymphatic system, tumor cells, stem cells, progenitor cells, and inflammatory cells. In certain embodiments of the invention, a biological sample that includes vascular cells includes endothelial cells, adventitial cells, pericytes and/or smooth muscle cells. In some aspects of the invention, a biological sample may comprise TARS that has been secreted from the cell in which it was produced. In certain aspects of the invention, a biological sample may comprise a TARS molecule that is a non-secreted molecule, which as used herein, is a TARS molecule that was produced in a cell but not secreted by that cell into the extracellular environment.

Biological samples for use in methods of the invention (e.g., for assessing a treatment, etc.) may be obtained from any number of sources. As used herein, the term "isolated", when used in the context of a biological sample, is intended to indicate that the biological sample has been removed from a subject. In some embodiments of the invention, a biological sample comprises a sample that has been isolated from a subject and is subjected to a method of the present invention without further processing or manipulation subsequent to its isolation. In some embodiments of the invention, a biological sample can be processed or manipulated subsequent to being isolated and prior to being subjected to a method of the invention. For example, a sample can be refrigerated (e.g., stored at 4° C.), frozen (e.g., stored at −20° C., stored at −135° C., frozen in liquid nitrogen, or cryopreserved using any one of many standard cryopreservation techniques known in the art). Furthermore, a sample can be purified subsequent to isolation from a subject and prior to subjecting it to a method of the present invention.

As used herein, the term "purified" when used in the context of a biological sample, is intended to indicate that at least one component of the isolated biological sample has been removed from the biological sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a tissue or tumor sample can be purified such that substantially only the polypeptide or mRNA component of the biological sample remains.

Furthermore, it may be desirable to amplify a component of a biological sample such that detection of the component is facilitated. For example, the mRNA component of a biological sample can be amplified (e.g., by RT-PCR) such that detection of TARS mRNA is facilitated. As used herein, the term "RT-PCR" (an abbreviation for reverse transcriptase-polymerase chain reaction) involves subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase for its amplification action. Alternative amplification methods include: self-sustained sequence replication (Guatelli, J. C. et al., 1990, Proc. Natl. Acad. Sci. USA 87: 1874-1878), transcriptional amplification system (Kwoh, D. Y. et al., 1989, Proc. Natl. Acad. Sci. USA 86: 1173-1177), Q-Beta Replicase (Lizardi, P. M. et all, 1988, Bio/Technology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

TARS Nucleic Acid Binding Agents

Types of binding agents that can be used in treatments and assays of the invention include, but are not limited to cDNA, riboprobes, RNAi compounds, and synthetic oligonucleotides, etc. The type of binding agent used in a treatment of the invention or to assess a treatment or treatment compound of the invention will generally be dictated by the particular situation, such as riboprobes for in situ hybridization, and cDNA for Northern blotting, antisense probe for binding, for example. Methods of the invention, in some embodiments, include identifying a candidate therapeutic compound and/or include assessing the efficacy of a therapeutic compound. In some embodiments of the invention a binding agent or probe can be directed to nucleotide regions unique to the polypeptide. Detection of the TARS-encoding gene, per se, may be useful for treatment methods of the invention and for assessing treatment methods and treatment compounds of the invention. Other forms of assays to detect TARS activity to determine efficacy of compounds of the invention that reduce activity of TARS transcripts and other expression products—will generally be useful as well. An RNA binding agent that is useful in a treatment of the invention may be as short as is required to differentially recognize TARS mRNA transcripts, and may be as short as, for example, 15 bases; however, agents of at least 17 bases, 18 bases, 19, bases, 20 bases, or more may be used.

An RNA or cDNA binding agent useful in methods of the invention may be reverse-engineered by one skilled in the art, for example using the amino acid sequence of GENBANK™ Accession No.:NM_152295. However use of such agents may be more limited than the native DNA sequence, as it will be appreciated that any one given reverse-engineered sequence will not necessarily hybridize well, or at all, with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

The form of labeling of a binding agent or probe used in an embodiment of the invention may be any that is appropriate, such as the use of radioisotopes, for example, $^{32}P$ and $^{35}S$, etc. Labeling with radioisotopes may be achieved, whether the agent or probe is synthesized chemically or biologically, by the use of suitably labeled bases using methods well known in the art.

TARS Detection Techniques

Some aspects of the invention include detection methods useful to assess treatments of the invention. In addition, certain methods of the invention may include detection methods to identify a candidate therapeutic compound and/or may to assess the efficacy of a therapeutic compound. For example, the efficacy of compounds and treatments of the invention to increase TARS activity can be assessed by detecting and measuring TARS molecules (for example, TARS polypeptides and nucleic acids that encode TARS polypeptides). For such methods of the invention TARS molecules can be detected and measured using any suitable means known in the art. In some embodiments of the invention, a detection or measurement means for TARS molecules includes an immunological assay, nucleotide determination (mRNA or DNA), mass spectrometry assessment, TARS aminoacylation, GTPase, or Ap4A synthesis assay, TARS active site determination assay, or a TARS binding assay that may include a TARS-binding reporter molecule. Examples of immunological assays suitable for use to assess treatment methods of the invention may include, but are not limited to ELISA assays, assays that utilize an anti-TARS antibody (or FV derivative) to which is conjugated a detectable label, (examples of which include but are not limited to a radiolabel, non-limiting examples of which are technicium and indium). In some aspects of the invention, TARS levels may be measured in complex mixtures using an amino acid (threonine) activation assay, aminoacylation assay, or binding of a threonine specific tRNA, or a nucleic acid aptamer designed and selected to bind to threonyl-tRNA synthetase.

In some embodiments of the invention, levels of a TARS polypeptide may be detected in complex protein mixtures using mass spectrometry methods, which may include a TARS-specific peptide as an internal standard to allow quantitation. Methods of measuring levels of nucleic acids encoding TARS (i.e. TARS mRNA) may include, but are not limited to, real-time polymerase chain reaction (qRT-PCR), DNA array, and next generation sequencing methods.

The present invention features agents that are capable of detecting and/or quantitating a TARS polypeptide or a TARS-encoding nucleic acid such that the presence and/or level of TARS are determined. As defined herein, an "agent" refers to a substance that is capable of identifying or detecting TARS in a biological sample (e.g., identifies or detects TARS mRNA, TARS DNA, TARS polypeptide, TARS activity, etc.). In some embodiments of the invention, the agent is a labeled or a labelable antibody or molecule (e.g., a binding partner) that specifically binds to a TARS polypeptide. It will be understood that as used herein, the term "polypeptide" is used in reference to an amino acid sequence of a full-length TARS protein or a portion of a TARS protein. As used herein, the terms "labeled" or "labelable" refers to the attaching or including of a label (e.g., a marker or indicator) or ability to attach or include a label (e.g., a marker or indicator). Markers or indicators useful in methods of the invention may include, but are not limited to, for example, radioactive molecules, colorimetric molecules, and enzymatic molecules that produce detectable changes in a substrate.

In some embodiments of the invention, an agent is an antibody that specifically binds to all or a portion of a TARS polypeptide. As used herein, the phrase "specifically binds" refers to binding of, for example, an antibody to an epitope or antigen or antigenic determinant in such a manner that binding can be displaced or competed with a second preparation of identical or similar epitope, antigen or antigenic determinant. In an exemplary embodiment, the agent is an antibody that specifically binds to all or a portion of the human TARS polypeptide. In some embodiments of the invention, an ELISA is used in conjunction with the antibody to determine the presence and/or level of TARS polypeptide in a biological sample. Methods of the invention for detecting the presence and/or quantity of a TARS molecule may also include procedures such as an immunological assay, a polymerase chain reaction, real-time polymerase chain reaction (qRT-PCR), mass spectrometry, a TARS aminoacylation assay, TARS active site determination assay, or a TARS binding assay comprising a TARS-binding reporter molecule. In addition, embodiments of the invention include may include nucleic "aptamers", i.e. nucleic acids (DNA, RNA or peptide nucleic acids [PNAs]) that possess high affinity for TARS derived polypeptides and can be readily labeled for high throughput binding assays. Aptamers can be produced by standard molecular biological techniques by those skilled in the art by repeated rounds of binding, selection, and affinity, and amplification (Hamaguchi, et al. *Anal. Biochem.* (2001) 294; pt 2, pages 126-131).

In some embodiments of the invention an agent is a labeled or labelable nucleic acid probe capable of hybridizing to a TARS nucleic acid, (e.g., a TARS RNA or DNA). For example, the agent can be an oligonucleotide primer for the polymerase chain reaction that flanks or lies within the nucleotide sequence encoding human TARS. In some embodiments of the invention, the biological sample being tested is an isolate, for example, RNA. In yet another embodiment, the isolate (e.g., the RNA) is subjected to an amplification process that results in amplification of TARS nucleic acid. As defined herein, an "amplification process" is designed to strengthen, increase, or augment a molecule within the isolate. For example, where the isolate is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

TARS RNA Detection Techniques

To identify a candidate therapeutic compound or to assess the efficacy of a therapeutic compound for treatment of an angiogenic or immune system disease or condition, RNA transcripts may be detected using art known methods. For example, Northern blotting, can be performed in which a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using known amplification methods. For example, it is within the scope of the present invention to reverse transcribe mRNA into cDNA followed by real-time polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR). Each of these methods is well known and routinely used in the art. Other known amplification methods can also be utilized in methods of the invention, including, but not limited to:

In situ hybridization visualization may also be employed, wherein a radioactively labeled antisense RNA probe is hybridized with a thin section of a biopsy sample, washed, cleaved with RNase and exposed to a sensitive emulsion for autoradiography. Biological samples may be stained with haematoxylin to demonstrate the histological composition of the sample, and dark field imaging with a suitable light filter shows the developed emulsion. Non-radioactive labels such as digoxigenin, etc. may also be used.

An isolated TARS polypeptide, or fragment thereof, can be administered in a treatment of the invention to treat an angiogenic or immune system disease of condition. The full-length TARS polypeptide can be used or, alternatively, the invention provides peptide fragments of TARS for administration in methods of the invention. A TARS polypeptide suitable for use in a method of the invention may comprise at least 8 amino acid residues of the amino acid sequence shown in GENBANK™ Accession No.: NM_152295 and encompasses an epitope of TARS such that an antibody raised against the peptide forms a specific immune complex with TARS. Polypeptides that may be used as immunogens include but are not limited to the sequence set forth as SEQ ID NO:7 RAELNPWPEYIYTRLEMYNILKAEHDSILAEKAEKDSKPIKVTLPDGKQV-DAESW KTTPYQIACGISQGLADNTVIAKVNNV-VWDLDRPLEEDCTLELLK, which is a portion of the sequence set forth in GENBANK™ Accession No.: NM_152295. In some aspects of the invention, an antigenic peptide may comprise at least 10, 11, 12, 13, 14, 15, 16, 17, 18, 19, 20, 21, 22, 23, 24, 25, 26, 27, 28, 29, 30, or more residues. Antigenic polypeptides comprising at least 50, 100, 150, 200 or 250 amino acid residues are also within the scope of the present invention. Preferred epitopes encompassed by the antigenic peptide are regions of TARS that are located on the surface of the polypeptide, e.g., hydrophilic regions. Antibodies that bind to TARS can be tested using routine methods to assess whether they are candidate compounds that may be administered to a subject to increase TARS activity in a cell, tissue, or subject in a treatment method of the invention.

A TARS immunogen typically may be used to prepare antibodies by immunizing a suitable subject, (e.g., rabbit, goat, mouse or other mammal) with the immunogen. An appropriate immunogenic preparation can contain, for examples, recombinantly expressed TARS polypeptide or a chemically synthesized TARS polypeptide. The preparation can further include an adjuvant, such as Freund's complete or incomplete adjuvant, or similar immunostimulatory agent. Immunization of a suitable subject with an immunogenic TARS preparation induces a polyclonal anti-TARS antibody response. The immunogen may further include a portion of non-TARS polypeptide, for example, a polypeptide useful to facilitate purification.

Accordingly, another aspect of the invention pertains to the use of anti-TARS antibodies to administer to a subject in an amount suitable to increase the level and/or activity of TARS polypeptides and to treat an angiogenic or immune system disease or condition. The term "antibody" as used herein refers to immunoglobulin molecules and immunologically active portions of immunoglobulin molecules, i.e., molecules that contain an antigen binding site which specifically binds (immunoreacts with) an antigen, such as TARS. The invention may include use of polyclonal and monoclonal antibodies that bind TARS. The term "monoclonal antibody" or "monoclonal antibody composition", as used herein, refers to a population of antibody molecules that contain only one species of an antigen binding site capable of immunoreacting with a particular epitope of TARS. A monoclonal antibody composition thus typically displays a single binding affinity for a particular TARS polypeptide with which it immunoreacts.

Polyclonal antibodies generated by the above or another technique may be used directly, or suitable antibody producing cells may be isolated from the animal and used to form a hybridoma by known means [Kohler and Milstein, Nature 256:795. (1975)]. Selection of an appropriate hybridoma will also be apparent to those skilled in the art, and the resulting antibody may be used in a suitable assay to identify and/or quantify a TARS molecule.

TARS Protein Detection Techniques

Methods of the invention may include the use of TARS binding molecules (e.g., antibodies, antibody equivalents, small molecules, etc.) to detect TARS polypeptides to permit identification of candidate therapeutic compounds and/or for assessment of the efficacy of a therapeutic compound of the invention. Thus, TARS binding molecules can be used to measure whether the activity of a TARS molecule in a subject or cell is altered by contact with a candidate compound or by a treatment regimen of the invention. Methods for the detection of polypeptides are well known to those skilled in the art, and include ELISA (enzyme linked immunosorbent assay), RIA (radioimmunoassay), Western blotting, and immunohistochemistry. Methods for immunoassays are routinely used and are well known in the art.

ELISA and RIA procedures may be conducted such that a TARS standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, TARS in the sample is allowed to react with the corresponding immobilized antibody, radioisotope- or enzyme-labeled anti-TARS antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay may involve contacting antigen with immobilized antibody and, without washing, contacting the mixture with labeled antibody. A "two-step" assay may involve washing before contacting the mixture with labeled antibody. Other conventional methods may also be employed as suitable.

Enzymatic and radiolabeling of a detection agent (e.g., antibodies, binding molecules, etc.) may be carried out by conventional means. Such means will generally include covalent linking of the enzyme to the detection agent, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of an assay system on a support, thereby allowing other components of the system to be brought into contact with the component and readily removed without laborious and time-consuming labor. It is possible for a second phase to be immobilized away from the first, but one phase may be sufficient.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled detection agent with the substrate under controlled conditions well-known in the art.

Other techniques may be used to detect TARS molecules according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-TARS antibodies (unlabeled) are then brought into contact with the support and assayed by a secondary immunological reagent, such as labeled protein A or anti-immunoglobulin (suitable labels including but not limited to $^{125}$I, horseradish peroxidase and alkaline phosphatase). Chromatographic detection may also be used.

Immunohistochemistry may be used to detect expression of human TARS in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay may be scored visually, using microscopy, or using any other suitable methods. Using detection methods one can determine efficacy of a treatment of the invention and can identify additional candidate agents for use in treatments of the invention.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Threonyl tRNA Synthetase (TARS) is an Angiogenic Chemokine Secreted by Endothelial Cells in Response to VEGF Materials and Methods for Example 1

Cell Culture, Reagents and Antibodies—

Human umbilical vein endothelial cells (HUVEC) (a gift from C. Holmes, University of Vermont) were grown in Clonetics® EGM®-2 complete media (Lonza, Annandale, N.J.). Borrelidin analog BC194 was a gift from Dr. Barrie Wilkinson, (Biotica). Purified basic-fibroblast growth factor (bFGF) was a gift from J. Spees, Univ. of Vermont. Retinoic acid and cycloheximide were purchased from Sigma-Aldrich, and VEGF and TNF-α were purchased from Cell Signaling Technology, Danvers, Mass. and Calbiochem, San Diego, Calif., respectively.

Western Blot—

After treatments, cells were harvested into sample buffer containing: 0.2 M Tris-HCL, 4% SDS, 4% β-mercaptoethanol, 40% glycerol, 4 µM pyronin Y. Extracts were sheared through a 24-gauge syringe. Samples were separated by 10% SDS-PAGE and transferred to nitrocellulose membrane and probed with specific antibody as described (Lounsbury, Beddow et al. 1994). Primary antibodies are as follows: Rabbit monoclonal anti-P-eIF2α (1:1000; Cell Signaling Technology, Danvers, Mass.), rabbit monoclonal anti-Cleaved Caspase-3 (1:1000; Cell Signaling Technology, Danvers, Mass.), rabbit polyclonal anti-TARS (1:500; Santa Cruz Biotechnology, Santa Cruz, Calif.). Loading control antibodies were rabbit monoclonal anti-β-actin and anti-β-tubulin (1:1000; Cell Signaling Technology, Danvers, Mass.). Secondary antibodies were HRP-goat-anti-mouse and HRP-goat-anti-rabbit (1:5,000; Jackson Laboratories, Bar Harbor, Me.).

In Vitro Tube Formation Assay—

Tube formation assays were performed as described (Arnaoutova and Kleinman 2010; Cassavaugh, Hale et al. 2011). Human Umbilical Vein Endothelial Cells (HUVECs) were seeded in 48-well plates (1.5×104 cells/well) coated with 100 μl of Matrigel™ Basement Membrane Matrix Growth Factor Reduced (BD Biosciences, San Jose, Calif.) and incubated in Clonetics® EGM®-2 complete media (Lonza, Annandale, N.J.) or EGM®-2 with reduced serum (0.2% fetal bovine serum). Cells were incubated at 37° C. for 6 h then fixed in 10% formalin. Fixed samples were imaged by phase-contrast microscopy or stained with Oregon Green 488 Phalloidin (Molecular Probes, Eugene, Oreg.) then imaged with fluorescence microscopy (2× objective). Number of tubes and tube lengths (in pixels) were quantified using the Simple Neurite Tracer (Longair, Baker et al. 2011) plug-in on ImageJ software (NIH). Statistical analysis of one-way ANOVA was performed with GraphPad Software. Multiple comparisons were performed using the Tukey Test.

Cell Viability—

Cell viability was measured by counting cells in a hemacytometer with Trypan Blue exclusion (Sigma-Aldrich, St. Louis, Mo.) according to manufacturer's instructions. Measurements were normalized to untreated cells.

Nascent Protein Synthesis Assay—

Nascent protein synthesis was measured using Invitrogen Click-iT® metabolic labeling reagents [Dieterich, D. C., et al., Nat Protoc 2, 532-40 (2007)]. HUVEC cultures were pre-incubated in methionine-free Dulbecco's Modified Eagle Medium (D-MEM) high glucose (Invitrogen, Life Technologies, Grand Island, N.Y.) supplemented with 10% dialyzed fetal bovine serum (Invitrogen) containing the control or test compounds. Cycloheximide (50 μM) was used as a positive control. After 45 minutes, 25 μM Click-iT® AHA (L-azidohomoalanine) (Invitrogen) was added and cultures were incubated for 3 h. Cells were lysed with 1% SDS in 50 mM Tris-HCl with protease and phosphatase inhibitors: 1 mM phenyl-methylsulfonamide, 20 mg/ml aprotinin, and 4 mg/ml leupeptin. Extracts were sonicated and protein concentration was determined by Bradford assay. Protein samples were labeled with biotin alkyne (PEG4 carboxamide-propargyl biotin) (Invitrogen) using the Click-iT® Protein Reaction Buffer Kit (Invitrogen) according to manufacturer's instructions. Equal concentrations of protein were run on a 10% SDS-PAGE and transferred to nitrocellulose membrane, incubated with streptavidin-HRP reagent (Pierce Thermo Scientific, Rockford, Ill.) followed by reaction with ECL reagent (Pierce) and exposed on film.

Expression and Purification of Human Aminoacyl tRNA Synthetases—

Figure 5:
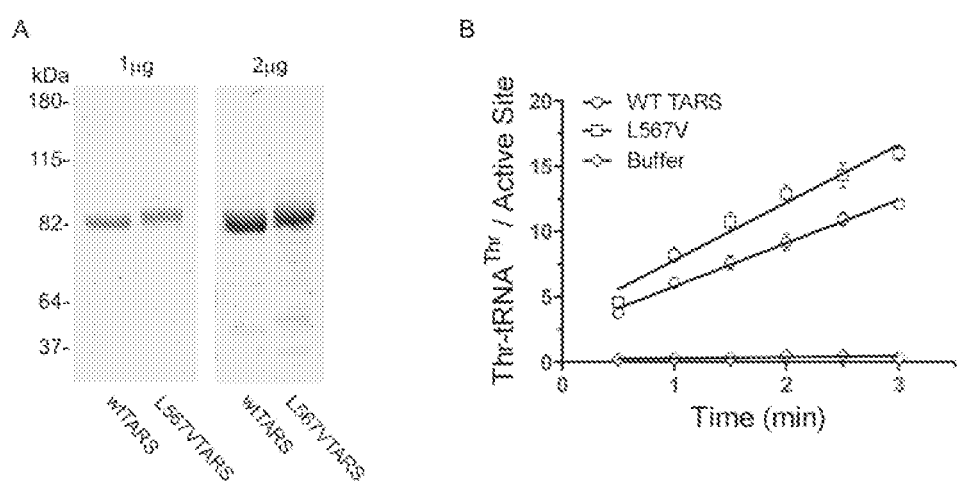
FIG. 5 provides a blot and graphs indicating expression and activity of human TARS and L567V TARS. Proteins were expressed and purified from E. coli Rosetta™ cells as described in Examples section.

N-terminal $His_6$-tagged human TARS (ThRS) was expressed and purified from *E. coli* Rossetta™ 2 (DE3) pLysS competent cells (EMD Millipore, Billerica, Mass.) transformed with derivatives of plasmid pET28a hctThrRS. Transformant cultures were grown in terrific broth supplemented with 100 mg/ml kanamycin and 100 mg/ml chloramphenicol at 37° C. to a cell density of A600=0.6. Expression of TARS was induced with 1 mM isopropyl 1-thio-β-D-galactoside overnight at 15° C. The bacterial pellet was lysed by sonication in buffer A (20 mM potassium phosphate buffer pH 8.0, 100 mM KCl, 35 mM imidazole, and 5 mM β-mercaptoethanol) and cleared by centrifugation at 17050×g for 30 minutes. Nucleic acids were precipitated by the addition of protamine sulfate to a final concentration of 0.3% followed be centrifugation. The supernatant was loaded onto a HisTrap™ FF column (GE Healthcare, Pittsburgh, Pa.) in buffer A and eluted by an imidazole gradient of 35-250 mM in buffer A over 20 column volumes. TARS containing fractions were identified by SDS-PAGE and GelCode™ Blue (Thermo Scientific, Rockford, Ill.), pooled, and dialyzed into buffer B (100 mM potassium phosphate buffer pH 6.8 and 5 mM β-mercaptoethanol). The sample was loaded onto a CHT-Tricorn Hydroxyapatite column and eluted over 20 column volumes by using a gradient of buffer B to buffer C (500 mM potassium phosphate pH 8.0 and 5 mM β-mercaptoethanol). TARS-containing fractions were determined by SDS-PAGE. Buffer B (10 mM HEPES pH 8.0, 100 mM KCl, 2.5 mM β-mercaptoethanol, and 40% glycerol), and stored at −20° C. TARS-containing fractions were pooled and dialyzed into buffer D (10 mM HEPES pH 8.0, 100 mM KCl, 2.5 mM β-mercaptoethanol, and 40% glycerol), and stored at −20° C. Protein concentration was determined by Abs260. The protein purity and stability were evaluated by Coomassie stain following SDS-PAGE, and concentration of active sites was determined using a steady state aminoacylation assay (FIG. 5).

The L567V mutant was derived from the wildtype TARS plasmid using Quikchange II Site-Directed Mutagenesis (Stratagene, Cedar Creek, Tex. [Agilent Technologies Inc., Santa Clara, Calif.]) with the forward primer 5' cac cag tgt gca acc atc cag ctg gat ttc cag gtg ccc atc aga ttt aat c 3' (SEQ ID NO:8) and its reverse compliment [5'-gat taa atc tga tgg gcc act gga aat cca get gga tgg ttg cac act ggt g-3' (SEQ ID NO:9)] and transformed into XL1-Blue cells. Colonies positive for the mutation were isolated, grown in LB media, and the plasmid purified via Qiagen miniprep kit. The plasmid was then transformed into Rosetta II cells for use in protein expression using the same protocol as for wildtype TARS.

Figure 9:
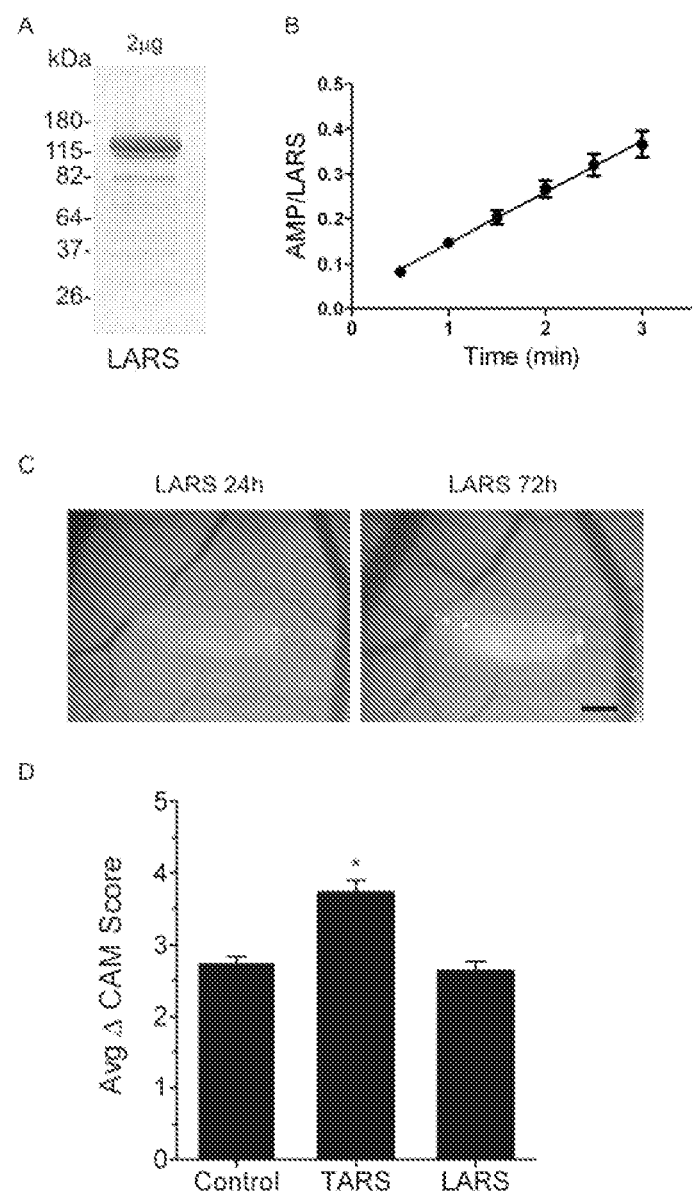
FIG. 9 provides a blot, graph, photomicrographic image, and a histogram showing the purification, activity, and lack of CAM effects of Leucyl tRNA synthetase (LARS). Human LARS was purified from $E.$ $coli$ as described in Materials and Methods in Examples section

N-terminal $HIS_6$-tagged human leucyl tRNA synthetase (LARS) was expressed using the plasmid pPROEX hTb-LARS and purified using a similar purification scheme to the TARS purification with minor modifications described in (Francklyn, First et al. 2008). The protein purity and stability were confirmed using SDS-PAGE and Coomassie stain (FIG. 9).

Steady State Aminoacylation Assay—

The aminoacylation activities of the TARS constructs were determined using modifications to established procedures (Francklyn et al 2008). Briefly, reaction mixtures consisted of 20 mM Tris-HCl pH 8.0, 100 mM KCl, 10 mM MgCl2, 1 mM dithiothreitol, 2 mM ATP, 2.5 U pyrophosphatase (Roche), 80 μM threonine, 20 μM [14C]-threonine, and 5 μM of *E. coli* or human tRNAThr. Reactions were initiated with the addition of 0.25-0.75 μM TARS and run at 37° C. Aliquots were taken at varying time points and spotted onto Whatmann 3MM paper filters pre-soaked in 5% trichloroacetic acid (TCA). Upon completion, the filters were washed 3 times in excess TCA, once in 95% ethanol, and dried under a heating lamp. The formation of Thr-tRNAThr was detected by scintillation counter and the activity determined by linear regression of threonyl-tRNAThr formed per active site per unit time.

LARS steady state ATPase activity was determined using the same procedure as for TARS aminoacylation with the following modifications. The reaction mixture did not include labeled threonine or tRNAThr and 1 nM [α-32P]

ATP (PerkinElmer, Waltham, Mass.) was added. Reactions were incubated for 3 minutes at 37° C. and initiated with the addition of 1 μM human LARS. At various time points 5 μl aliquots were quenched in 45 μl of 500 mM sodium acetate and 0.1% sodium dodecyl sulfate. For each sample, 1 μl was spotted onto a CCM cellulose PEI F plates (EMD) and resolved via thin-layer chromatography in 0.75 M potassium phosphate buffer mobile phase. Radioactive signals were detected via phosphorimaging and AMP production overtime was quantified using Quantity One v 4.6.6 software (Bio-Rad, Hercules, Calif.).

Chick Chorioallantoic Membrane Assay—

Fertilized chicken eggs (Sunrise Farms, Catskill, N.Y.) day 1-2 post-laying were incubated in a humidified incubator at 37° C. for 72 h. Cleaned eggs were cracked and plated in a sterile 10 cm$^2$ tissue culture-treated dish and incubated at 37° C. for another 7 days. On developmental day 10, 1 mm$^3$ sterile gelatin sponge pieces (Surgifoam®; Johnson & Johnson Wound Management, Somerville, N.J.) were placed within the outer one-third of the membrane between large vessels. 40 μg/ml human bFGF and 2 μg/ml human VEGF were used as pro-angiogenic control compounds; 100 μg/mL retinoic acid (Sigma-Aldrich, St. Louis, Mo.) diluted in phosphate-buffered saline (PBS) was used as an angiostatic control. All compounds were applied in 10 μl to the CAM every 24 h for 72 h. Images were taken using a Leica MZ6 stereomicroscope every 24 h. Compounds were scored according to a modified version of Intensity Scoring as previously described (Ribatti, Nico et al. 2006). Briefly, each experimental condition was given a blinded score from 0-5 based on the change in the extent of vessel convergence and formation in proximity to the sponge from day 0 to day 3. Total score is averaged individual experimental condition scores from at least 15 replicates.

ELISA and Lactate Dehydrogenase Assays—

Confluent HUVEC cultures (passage 4) were incubated at 37° C. in Clonetics® EGM®-2 modified with 0.2% fetal bovine serum with the addition of 50 ng/ml human VEGF or 50 ng/ml human TNF-α for 6 h as indicated. Culture media supernatants were tested for levels of secreted TARS protein using the Threonyl tRNA Synthetase (TARS) ELISA Kit (USCN Life Science, Wuhan, Hubei, PRC) according to manufacturer's instructions. Cell membrane integrity was confirmed using the lactate dehydrogenase assay CytoTox-ONE™ Homogeneous Membrane Integrity Assay (Promega, Madison, Wis.) according to manufacturer's instructions and reported as percent cytotoxicity relative to a lysis control. Levels of secreted VEGF were measured using the Human VEGF ELISA kit (Thermo Scientific) per manufacturer's instructions.

Quantitative RT-PCR—

Total RNA was extracted from cells using the RNeasy column protocol and cDNA was generated using an Omniscript reverse transcriptase assay according to the manufacturer's instructions (Qiagen, Frederick, Md.). Primers and probes for TARS and β2-microglobulin were Assays-on-Demand (Applied Biosystems, [Life Technologies, Carlsbad, Calif.]). RT-qPCR was performed using an ABI prism 7700 Sequence Detection System (Applied Biosystems). The relative quantity of mRNA level was determined using the comparative CT (ΔΔCT) method using β2-microglobulin to normalize mRNA level (Cassavaugh, Hale et al. 2011).

Endothelial Cell Proliferation Assay—

The MTT-based alamarBlue® (Invitrogen) reagent was used to assess cell proliferation (Ahmed, Gogal et al. 1994). HUVECs were seeded in a 96-well dish (1×10$^3$ cells/well) and grown for 48 h in EGM®-2 media. Cells were incubated in 0.2% FBS EGM®-2 media or EGM®-2 complete media as indicated; VEGF (50 ng/ml) and media alone served as controls. After 48 h, 72 h, or 96 h in culture, 10 μl/well premixed alamarBlue® (Invitrogen) was added and after 3 h at 37° C. the amount of reduced alamarBlue® was quantified by fluorescence (excitation at 530 nm, emission at 590 nm) on a microplate reader (Synergy™ HT, BioTek, Winooski, Vt.).

Transwell Migration Assay—

Migration was assessed using transwell inserts (Svensson, Kucharzewska et al. 2011). HUVEC cultures were serum-depleted overnight in Clonetics® EGM®-2 modified with 0.2% fetal bovine serum then 5×10$^4$ cells were plated in 90% EBM®-2, 10% EGM®-2 in the upper chamber of 0.2% gelatin-coated 24-well 8 μm Transwell® inserts (Corning, Tewksbury, Mass.) with 90% EBM®-2, 10% EGM®-2 media plus 50 ng/ml VEGF, 1-100 nM TARS protein, or 10 nM BC194 in the lower chamber. Cultures were incubated for 4 h, fixed in 10% formalin, and stained with 10 μg/ml DAPI solution (Roche) following removal of cells from the top layer of the chamber with a cotton swab. Migrated cells were imaged using a 4× objective on the Olympus IX70 Inverted microscope (Olympus). DAPI-stained nuclei were counted using ImageJ software.

Statistical Analysis—

Data are presented as mean±SEM, and p<0.05 is considered significant. Except where indicated, one-way ANOVA for multiple comparisons was performed on all data. A Kruskal-Wallis adjustment was used where necessary. All pairwise comparisons were assessed using the Student's t-test.

Results for Example 1

Concentration-Dependent Effects of a TARS Inhibitor Reveal a Specific Angiogenic Function for TARS.

Figure 2:
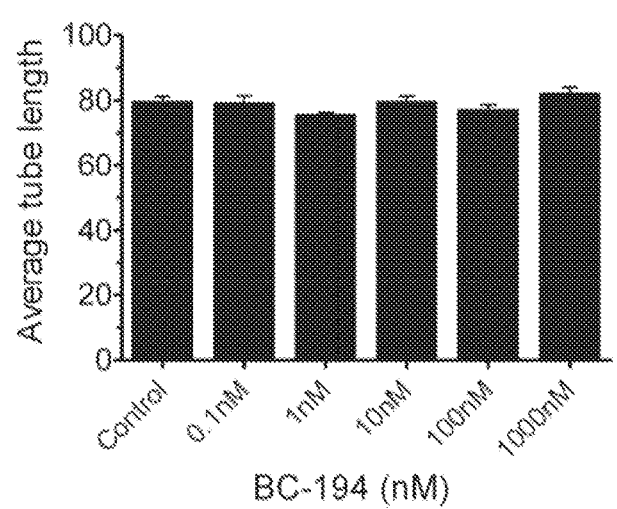
FIG. 2 is a graph showing that BC194 does not affect endothelial tube branch length. HUVECS were treated with the indicated concentration of the TARS inhibitor BC194. Graph shows quantification of branch length in pixels over a range of BC194 concentrations using the Simple Neurite Tracer plug-in on ImageJ software. Multiple comparisons of one-way ANOVA were performed using the Tukey Test; n=3.
Figure 3:
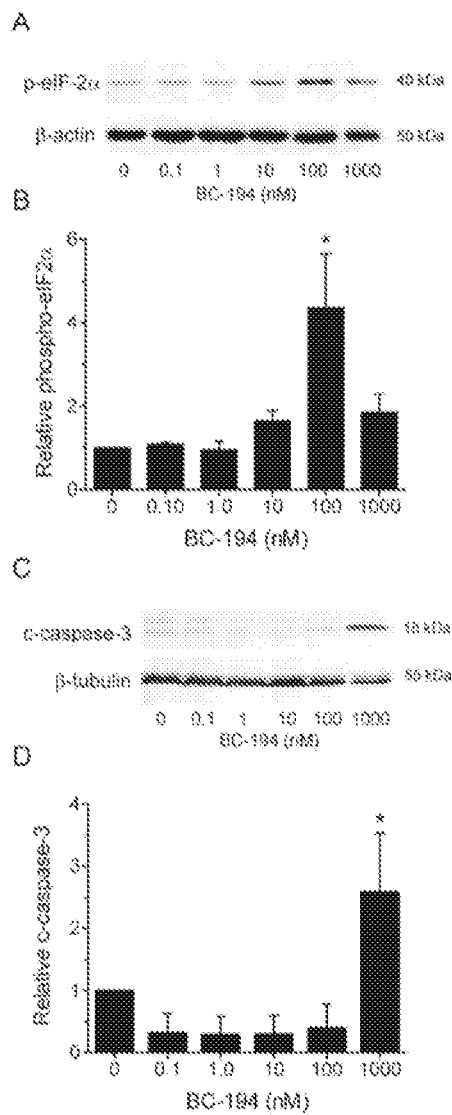
FIG. 3 shows Western blots and graphs that indicate that high concentrations of BC194 are required to stimulate the unfolded protein response and apoptosis. HUVECs grown in full serum media were exposed to the indicated concentrations of BC194, followed by Western Blot of cell extracts using antibodies recognizing phospho-eIF2α (FIG. 3A), cleaved caspase-3 (FIG. 3B) and β-actin or β-tubulin as a loading control. Quantification of phospho-eIF2α and c-caspase-3 relative to the loading controls were determined using Quantity One software and average data are shown in FIGS. 3C and 3D; respectively *p<0.05, n=3.
Figure 4:
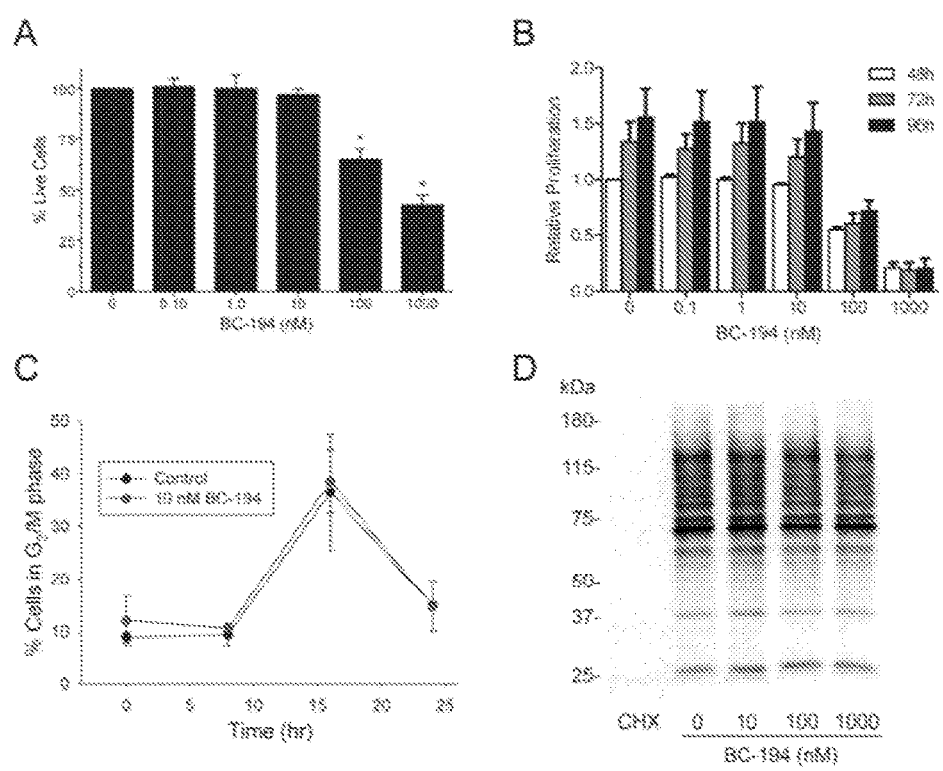
FIG. 4 provides graphs and an SDS-PAGE illustrating a lack of effect of BC194 on cell viability and protein synthesis.
Figure 8:
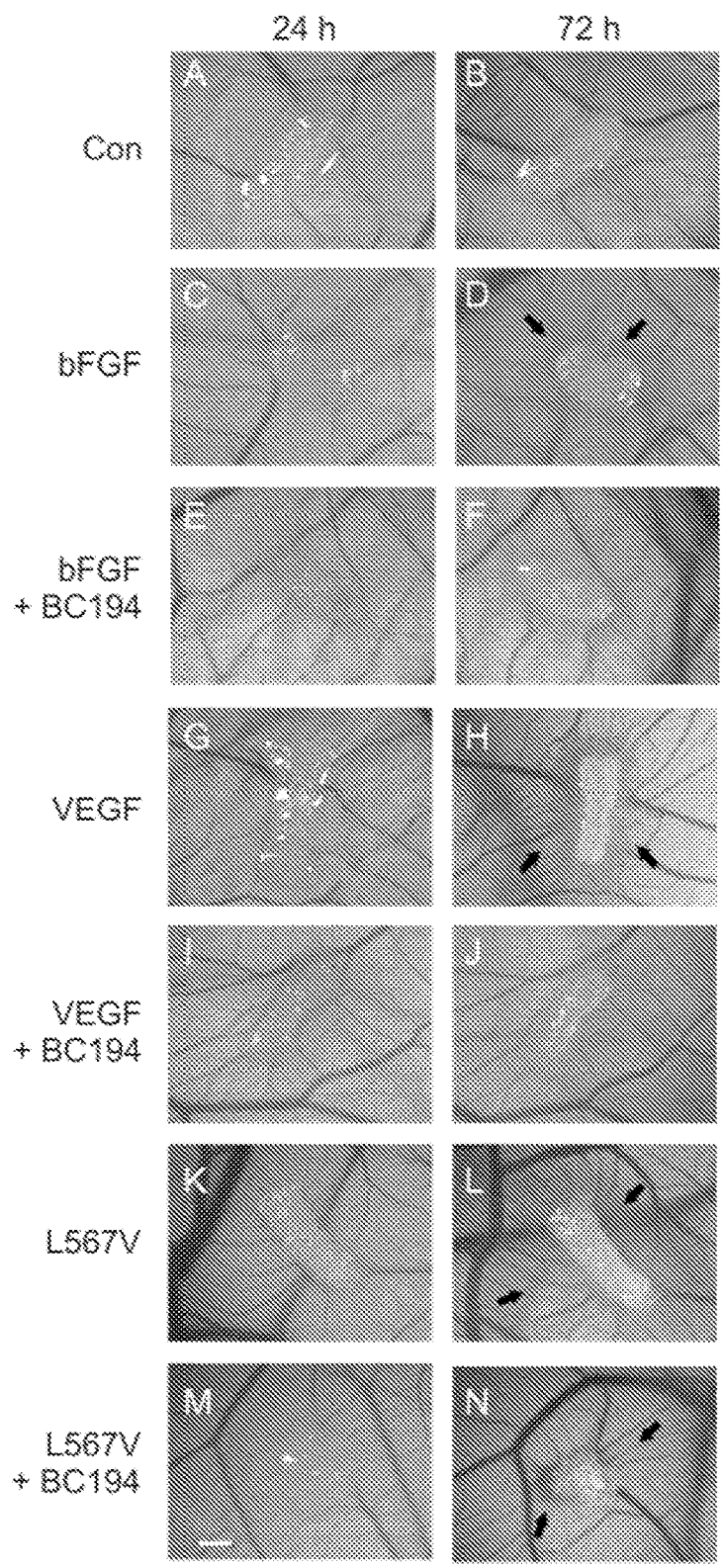
FIG. 8 provides representative photomicrographic images for the graphs shown in FIGS. 7A and 7B. Fertilized chicken embryos were cultured ex-ova and, starting at developmental day 10, agents were applied daily to gelfoam sponges on the CAM. Left panels represent images taken at 24 h and right panels at 72 h for PBS Control (FIGS. 8A and 8B), bFGF (FIGS. 8C-F), VEGF (FIGS. 8G-J) and L567V TARS (FIGS. 8K-N). BC194 (100 ng/sponge) was included where indicated. Arrows indicate spoke-wheel response; Scale bar=1.0 mm.

Inhibition of TARS by BC194 has been shown previously to reduce in vitro endothelial tube formation (Wilkinson, Gregory et al. 2006); however, because TARS is a component of the protein synthesis machinery, this effect could be explained by cell toxicity through the unfolded protein response or apoptosis pathways. By using a range of BC194 concentrations, the sensitivity of HUVECs to the anti-angiogenic versus cell stress effects of BC194 was compared. As shown in FIG. 1, the number of branches formed by endothelial cells in a tube formation assay was sensitive to subnanomolar concentrations of BC194, although tube length was unaffected (FIG. 2). The concentration of BC194 required to affect tube formation was 100-fold lower than that required to detect the unfolded protein response (phospho-eIF2α) and apoptosis (cleaved caspase-3) (FIG. 3). Effects on cell viability, proliferation, and nascent protein synthesis were also unaffected by BC194 at concentrations below 100 nM (FIG. 4). These data suggest that TARS may serve a secondary function in angiogenesis signaling that is separate from its function in protein synthesis and is highly sensitive to inhibition by BC194. (FIG. 8 provides photomicrographic images representative for the data shown in FIG. 4).

Exogenously Added TARS Stimulates Angiogenesis.

Figure 6:
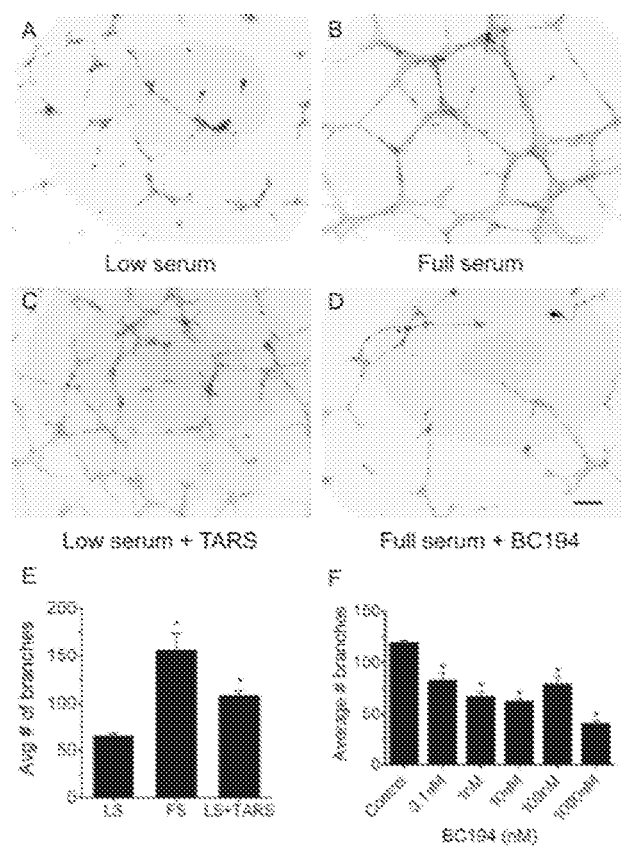
FIG. 6 provides photomicrographic images and a graph providing evidence that exogenous application of TARS promotes angiogenesis by an in vitro endothelial tube formation assay.

In light of the potential role for TARS in angiogenic signaling and the secreted activity of select other aminoacyl tRNA synthetases (Wakasugi and Schimmel 1999; Greenberg, King et al. 2008), the ability of purified TARS to stimulate angiogenesis was tested using the in vitro tube formation assay. Human His-tagged TARS was expressed in *E. coli* and purified by nickel chromatography followed by sequential column chromatography to produce an active and pure preparation (FIG. 5). As shown in FIG. 6, addition of TARS to low-serum media significantly increased the number of tube branches, suggesting that TARS itself is angiogenic and implicating an extracellular effect for BC194's anti-angiogenic effect on endothelial cells.

Figure 7:
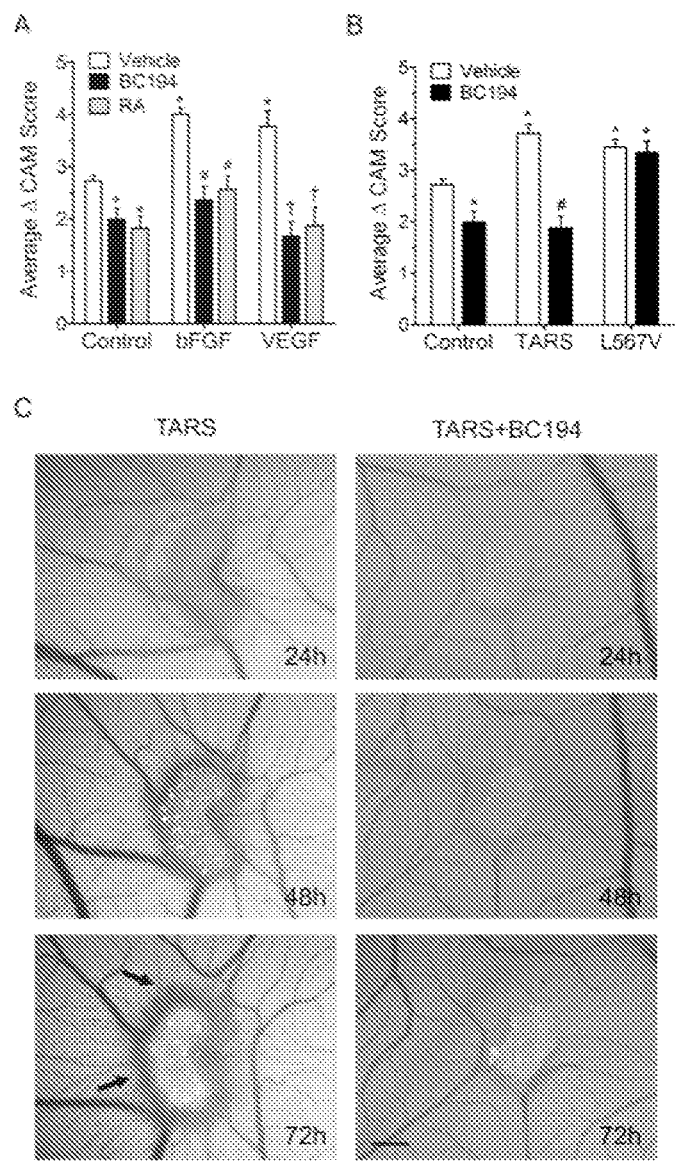
FIG. 7 provides graphs and a photomicrographic image demonstrating that TARS induces in vivo angiogenesis in a CAM assay. Fertilized chicken embryos were cultured ex-ova and, starting at developmental day 10, agents were applied daily to gelfoam sponges on the CAM. Images were recorded daily over 72 h and scored blindly according to a modified version of Intensity Scoring as previously described (Ribatti et al, 2006). Graphs represent the change in CAM vascularity score over 72 h.

To confirm and expand these results, a chorioallantoic membrane (CAM) assay was used to examine a role for TARS in an in vivo angiogenesis environment. Daily application of BC194 to a gel sponge on the CAM over 4 days inhibited vessel formation at both the basal level and after stimulation with either bFGF or VEGF (FIG. 7A). Application of TARS to the CAM stimulated vessel formation and the angiogenic effect was sensitive to BC194, suggesting that the inhibition of angiogenesis by BC194 is not due to off-target effects (FIG. 7B,C). This conclusion was further supported by the finding that a BC194-resistant mutant of TARS, L567V TARS, stimulated vessel formation that was not inhibited by application of BC194 (FIG. 7C). Application of Leucyl tRNA synthetase (LARS) to the CAM had no observable effect on vascularization, suggesting that the angiogenic effect is not a property of all tRNA synthetases (FIG. 9). Together these data support a specific role for extracellular TARS in the activation of the in vivo endothelial angiogenic response.

TARS is Secreted in Response to VEGF and TNF-α.

Figure 10:
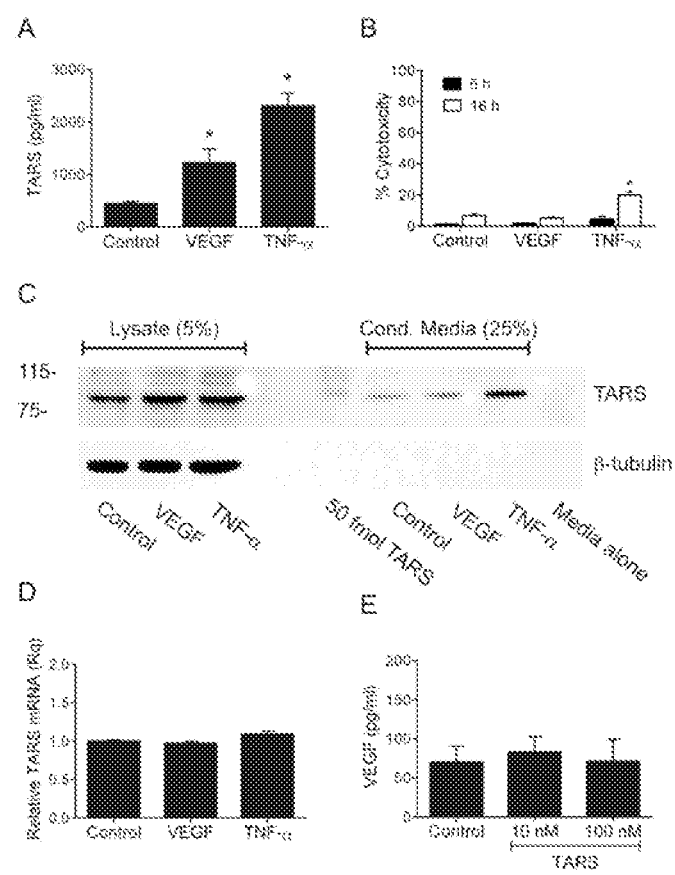
FIG. 10 provides graphs and a Western blot demonstrating that TARS is secreted by endothelial cells in response to VEGF and TNF-α.

Although TARS exerts significant pro-angiogenic effects, there was no prior evidence that TARS is physiologically present in the extracellular space except as a result of cell lysis. To explore the possibility that TARS is actively secreted, endothelial cells were treated with VEGF or TNF-α followed by measurement of TARS in the media using ELISA. As shown in FIG. 10A, both VEGF and TNF-α stimulated a significant increase in TARS in the media, in an excess of 1000 pg/ml. The TARS present in the media was not due to cell lysis as confirmed by a cytotoxicity assay (FIG. 10B). The presence of TARS in the media was also not due to an increase in TARS expression since neither VEGF nor TNF-α induced an increase in TARS mRNA (FIG. 10D). Furthermore, adding purified recombinant TARS to the cell media did not induce secretion of VEGF as measured by ELISA (FIG. 10E). These results support a mechanism whereby TARS secretion is increased following stimulation of endothelial cell signaling through VEGF or TNF-α receptors.

TARS Stimulates Endothelial Cell Migration.

Figure 11:
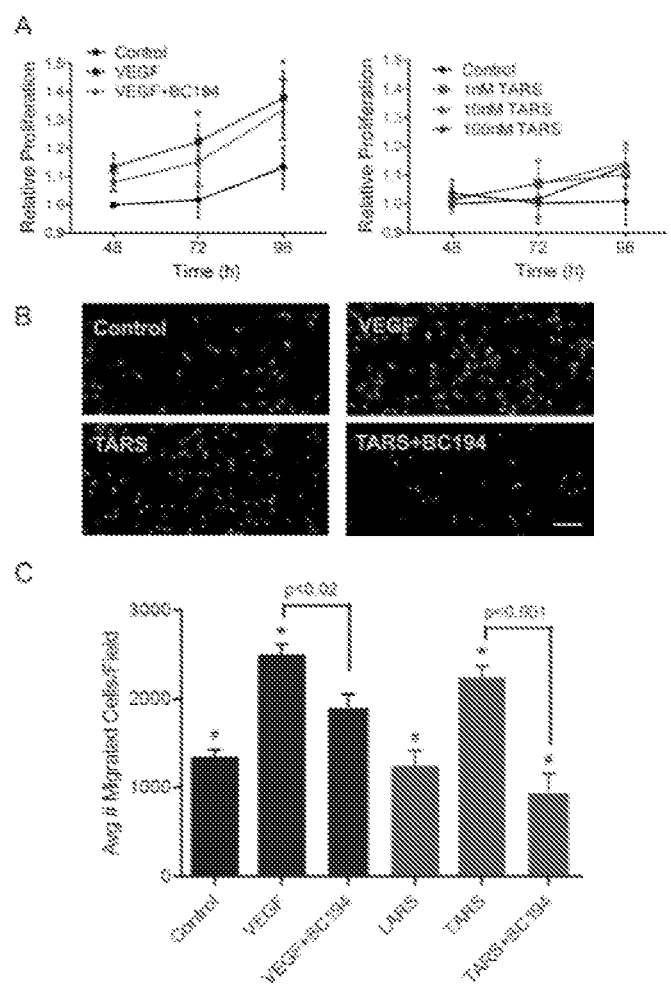
FIG. 11 provides graphs, photomicrographic images and a histogram showing that TARS selectively induces migration of endothelial cells that is sensitive to BC194.

An increase in angiogenesis by TARS signaling to endothelial cells could have resulted through either an increase in cell proliferation or an increase in cell migration. Unlike VEGF, TARS did not exert a significant effect on cell proliferation, and BC194 did not significantly reduce the VEGF proliferative response (FIG. 11A). However, TARS significantly increased migration of endothelial cells in a transwell assay to an extent that was similar to VEGF (FIG. 11B). LARS did not affect migration, indicating that the TARS-mediated effect was not a non-selective result of synthetase activity. Importantly, BC194 reduced both the migration effects of VEGF and TARS, although the VEGF effect was less pronounced, suggesting that TARS may play a significant role in VEGF-mediated endothelial cell migration. This evidence supports a mechanism for TARS that includes stimulation of endothelial cell migration that contributes to its angiogenic effect.

Figure 12:
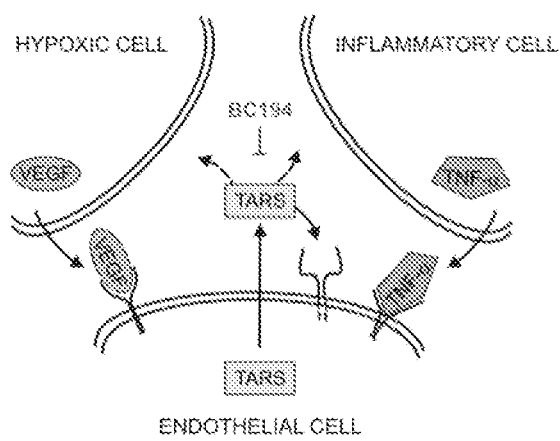
FIG. 12. Is a schematic diagram of a proposed model for TARS signaling and angiogenic activity. VEGF and TNF-α secretion by hypoxic and cells of the tumor microenvironment leads to VEGF receptor activation on endothelial cells and secretion of TARS. Secreted TARS has autocrine and possibly paracrine functions that promote angiogenic signaling. BC194 binds and inactivates TARS, preventing its angiogenic function. Thus, TARS present in patient serum could be an indicator of the angiogenic potential of tumors.

TARS may be playing a substantial role in normal and pathogenic angiogenesis as a proangiogenic chemokine activated by endothelial cells in response to VEGF or TNF-α stimulation (FIG. 12). With this as the first report of the novel angiogenic function of TARS, much remains to be uncovered about how TARS signals to endothelial cells, other processes beyond migration and angiogenesis secreted TARS may be affecting, and linkages between TARS and tumorigenesis.

Example 2

Database Assessment of TARS in Disease

Database analysis was used to assess TARS expression in cancers including Cancer Gene Anatomy Project (CGAP) (Strausberg 2001), GEO database, and Human Protein Atlas (Uhlen, Oksvold et al.). Using the CGAP database, TARS mRNA was found to be over-expressed in cells derived from prostate carcinoma, colon adenocarcinoma, ovarian carcinoma, and in certain stem cell lines. Furthermore, whereas other synthetases were found to be relatively unchanged, TARS protein was found to be selectively upregulated in ovarian tumors from tissue arrays displayed in the Human Protein Atlas. (www.proteinatlas.org/ENSG00000113407).

A preliminary investigation using GEO data from a prostate cancer progression study by Tomlins et al. (Tomlins, Mehra et al. 2007) revealed that mRNA levels of TARS exhibited a 2.9 fold increase in prostate carcinoma versus normal ($p<0.0001$). To expand on these findings, GEO dataset GSE6919, 171 sample CEL files (scanned chip image files) were downloaded. GSE6919 is a GEO Super-Series that includes GSE6604 (normal prostate tissue from 18 patients), GSE6605 (metastatic prostate tumor included 25 samples from 4 patients and 9 sites, some paired), and paired sets GSE6606 (primary prostate tumor from 65 patients), and GSE6608 (normal prostate tissue adjacent to tumor from 63 of those patients). Probe-level intensities were background-corrected, normalized, and summarized, and Robust Multichip Average (RMA) statistics are calculated for each probe set and sample as is implemented in Partek Genomic Suites, version 6.6 Beta (Copyright 2009, Partek Inc., St. Louis, Mo., USA). Sample quality was assessed based on the 3':5' ratio, relative log expression (RLE), and normalized unscaled standard error (NUSE). Principal Component Analysis (PCA) was also used to look for outlier samples that would potentially introduce latent variation into the analysis of differential expression across sample groups. Based on these analyses, 13 samples were eliminated from further analysis. Additional analysis included assessment of GEO datasets. Results of the analysis, which included a comparison of samples of normal and metastatic prostate cancer tumors, indicated that TARS mRNA was found to be significantly elevated. These findings were selective for TARS in that other aminoacyl tRNA synthetases were not elevated in prostate cancer.

Example 3

Analysis of TARS Expression in Prostate Cancer Patients

Patient Selection for IHC Studies—

Using an IRB protocol (CHRMS #:08-218) approved by UVM Committee on Human Subjects, FAHC patient registries were searched to identify patients with high grade PCa from 2008-2010 for whom archived tissue samples were available. The search was confined to those patients for whom a clinical record was available, and who had all undergone prostatectomies, and for whom there were clinical samples available. An initial set of 54 cases with PC surgeries from October 2008 to March 2010 was collected in this way. A second group of 79 patients with high-grade disease was identified with surgeries over the interval December 1999-August 2002.

Immunohistochemistry—

The immunohistochemistry procedures were conducted essentially as described (Conant, Penz, et al., 2011). Slide mounted 5 μm tissue sections cut from formalin-fixed, paraffin-embedded (FFPE) prostate carcinoma specimens were dewaxed by 3×5 mins washes in xylene followed by rehydration through graded ethanol washes (100%, 95%, 70% and 50%; 2×3 mins in each). After rinses in Milli-Q ultra-pure water (EMD Millipore, Billerica, Mass.), heat induced epitope retrieval (HIER) was performed by immersing the slides in Target Retrieval solution pH 6.0 (Dako North America Inc., Carpenteria, Calif.) and heating at 100° C. for 15 mins in a Decloaking Chamber™ Pro pressure cooker (Biocare Medical, Concord, Calif.). Slides were then allowed to cool in the pressure cooker unit for another 20 minutes. After 3×5 minute rinses in TBST (25 mM Tris, 0.15M NaCl, 0.05% Tween 20), slides were immersed in 3% $H_2O_2$/TBST for 15 mins as to inactivate any endogenous peroxidase in the tissues. After 3×5 min washes in TBST slides were immersed in protein block, serum-free ((Dako North America Inc., Carpenteria, Calif.) for 15 minutes to block non-specific protein binding sites in the tissues. Primary antibody (anti-TARS, mouse monoclonal clone 1A9, Abnova, Walnut, Calif.) at a 1:200 dilution was then applied for 30 min at room temperature. As a negative control test, IHC was also performed substituting primary antibody with a mouse monoclonal (mAb) IgG1 antibody to *Aspergillus niger* glucose oxidase (Dako North America Inc., Carpenteria, Calif.). After TBST washes, secondary detection was performed by incubating the slides for 30 mins RT with EnVison+ Dual Link polymer HRP (horseradish peroxidase) reagent (Dako North America Inc., Carpenteria, Calif.). Following a further series of TBTS washes, slides were incubated for ~6 minutes with DAB+ chromogen substrate (Dako North America Inc., Carpenteria, Calif.) and then rinsed with tap water. Tissues were then counterstained with hematoxylin for ~7 minutes, rinsed with TBST and water and the dehydrated through 50%, 70%, 95% and 100% ethanol. Finally, slides were cover-slipped with Cytoseal mountant (ThermoFisher Scientific, Waltham, Mass.) for viewing by bright-field microscopy.

Imaging Details—

Figure 13:
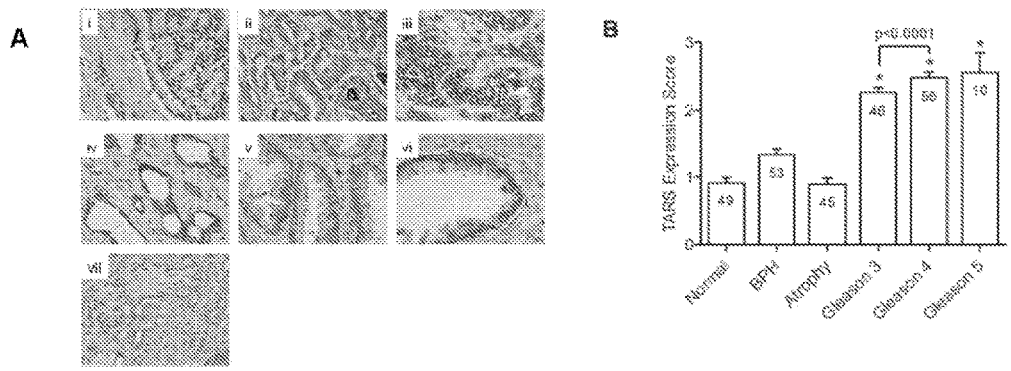
FIG. 13 provides photomicrographs and a histogram of statistical analysis correlating TARS levels in prostate cancer tissue sections with Gleason score, and a table depicting the results of initial ELISA measurements on serum samples from prostate cancer patients. The images in FIG. 13A show results of immunohistochemistry of TARS within patient tissue sections showing examples of the scoring rubric. (i=TARS+1, ii=TARS+2, iii=TARS+3, iv=Atrophy, v=benign prostate hyperplasia (BPH) TARS+1, vi=BPH TARS negative, and vii=TARS negative).

Images of IHC were captured at the Micrscopy Imaging Center at the UVM College of Medicine using an Olympus BX50 light microscope, QImaging Retiga 2000R camera, and QCapture Pro Software. The final images used for standards in grading are seen in FIG. 13A.

Immunohistochemistry Scoring—

The stained slides were initially scored by a primary pathologist, and then a secondary review was provided two other expert pathologists. In the scoring procedure, the pathological grade and the intensity of TARS immunochemical staining were evaluated independently. In the pathological grading, each slide was evaluated by assigning different region of the slide to benign (non-tumor) and tumor. The total tumor area was further subdivided into Gleason primary pattern 3, 4, or 5, and a % of tumor region estimated for each. (There are no Gleason scores below 2, because such patients were never subjected to prostatectomies.) The AJCC criteria were used to make these pathological assessments. The pathological assessment also included the recording and grading of HGPIN (a precursor lesion to PCa) and several benign controls, including BPH and atrophy (characterized by small, hyperchromatic nuclei with no prominent nucleoli). The experimental analysis also noted tissue staining pattern (diffuse, focal, or scattered), and any additional notes (such as tertiary Gleason grade, lymph node metastasis, or extraprostatic extension (EPE). In cases where there were uncertainties and/or ambiguities, the original H&E stained slides corresponding to each case were referenced. The TARS IHC staining intensity was graded independently, using a semiqualitative scale from 0-3 (0=negative, 1=mild, 2=moderate, and 3=strong). A set of reference slides that served to calibrate the scoring procedure is shown in FIG. 13A. The regions of each slide corresponding to the various Gleason scores were each independently scored for TARS, as was the "benign" region.

Statistical Analysis.

Univariate statistics were used to determine the significance between TARS staining and tumor type. Secondary t-tests were done to correlate TARS intensity with progression from Gleason 3 to 4 and to correlate TARS intensity with PSA and biochemical failure.

ELISA Assays. TARS ELISA was perform on neat serum samples, according the manufacturer's (CUSABIO Biotech, Wuhan, P.R. China) instructions. The serum samples from four age matched male non-cancer subjects was used as the control group.

Results for Example 3
Immunohistochemical Analysis of TARS Expression in Prostatectomy Sections.

To assess the relationship between TARS expression and prostate cancer progression, patient tumor samples were analyzed by immunohistochemistry and scored by intensity as shown in FIG. 13A. Statistical analysis of the data concluded that TARS protein levels are increased in tumors with Gleason score of 3 and above (FIG. 13B). In addition, a post-analysis of the TARS intensity found a significant increase in expression during progression from Gleason score 3-4 with a mean difference of 0.304, and a p-value of 0.0001.

TARS expression was also compared with 10-year outcome. When TARS staining of the various anatomical grades was examined, there was a strong relationship between Gleason 5 staining and elevated PSA at 10-years. Specifically, a one unit increase in TARS staining on the Gleason 5 portion of the slide increases the odds by a factor of 2.211 that subject will experience biochemical failure. Taken together these results suggest that TARS expression correlates with diagnosis of prostate cancer, progression of disease and likelihood of biochemical failure.

Analysis of Circulating TARS Levels in Prostate Cancer Patients.

The essential features of a useful human biomarker are that it be present in medium that can be readily obtainable in a non-invasive fashion (e.g. serum or urine), that it be readily quantifiable using a robust and repeatable assay, and that it provide useful information that reflects on subject disease state. As part of the very initial process of TARS biomarker discovery, serum samples were collected from 10 consenting subjects of the Fletcher Allan Urology Clinic. This small set included patients at various points along the prostate cancer diagnosis/treatment continuum, including immediately after diagnosis prior to treatment; under active surveillance; and under androgen deprivation therapy following prior radiation or prostatectomy surgery. Serum samples from four age and gender matched control subjects were also analyzed. All samples were measured in duplicate, and the values reported in FIG. 13C are mean values.

The mean value of circulating TARS concentration in the control samples was 105±19.5 pg/mL. Two patients (TARS 0012 and TARS 0013) had values higher than the controls, and the other eight patients all exhibited values lower than the controls. In three cases (TARS 0014, TARS 0016, and TARS0018) the levels of circulating TARS were undetectable, and significantly decreased levels were seen in three others (TARS0011, TARS0014, and TARS 0017). In three of the six cases where TARS levels were significantly decreased or not detectable, the patients were on androgen deprivation therapy. In one patient under androgen deprivation therapy, TARS levels were increased 50% relative to the controls. Notably, the two patients with TARS levels closest to the controls had either received no treatment or were under active surveillance. These data allow several important conclusions regarding the potential utility of TARS as a prostate cancer biomarker to be drawn. First, the TARS enzyme can be readily detectable in human serum samples by a conventional and commercially ELISA kit without any extensive modification or adaptation. Secondly, the variation in levels among different subjects is within the dynamic detection range of the kit. Thirdly, the values seen in untreated or active surveillance patients were closer to the values seen in the controls than samples derived from patients who had undergone past surgery/radiation treatments and were currently under androgen deprivation therapy. This provides initial support for the hypothesis that circulating TARS levels change in prostate cancer patients in response to treatment. It is noteworthy that the significant drop in TARS levels seen with patients under androgen deprivation suggests that TARS expression is at least partially under the control by the androgen receptor.

Example 4

TARS Interacts with VHL and its Inhibition Interferes with the Ovarian Cancer Cell Response to Hypoxia
Materials and Methods for Example 4
Co-Immunoprecipitation—
Plasmids expressing biotinylatable TARS (pTARS) and myc-tagged VHL (pVHL) were transfected into HEK293 cells, and then extracts were prepared. Biotin-TARS was precipitated using streptavidin-coupled beads. Myc-VHL was precipitated using anti-myc antibodies. Precipitates were separated by SDS-PAGE, transferred and blots probed with anti-TARS antibody or anti-myc (VHL) antibody.
Western Blot—
After treatments, cells were harvested into sample buffer containing: 0.2 M Tris-HCL, 4% SDS, 4% β-mercaptoethanol, 40% glycerol, 4 µM pyronin Y. Extracts were sheared through a 24-gauge syringe. Samples were separated by 10% SDS-PAGE and transferred to nitrocellulose membrane and probed with rabbit polyclonal anti-TARS (1:500; Santa Cruz Biotechnology, Dallas, Tex.) or monoclonal anti-HIF-1α (BD Transduction Laboratories, [BD Biosciences, San Jose, Calif.]) (Lounsbury, Beddow et al. 1994). Secondary antibodies were HRP-goat-anti-mouse and HRP-goat-anti-rabbit (1:5,000; Jackson Laboratories, Bar Harbor, Me.).
Mass Spectrometry.
Culture dishes were seeded with $2 \times 10^6$ human embryonic kidney cells (HEK293) and maintained in DMEM (Mediatech, Manassas, Va.) supplemented with 10% fetal bovine serum (Gibco, Carlsbad, Calif.), penicillin/streptomycin (Gibco), and L-glutamine (Gibco) at 37° C. and 5% $CO_2$ in a humidified incubator. Cells were transfected by polyethylenimine with plasmids encoding a TARS construct with C-terminal HA tag and BirA biotinylation site, BirA, and C-terminally myc-tagged VHL. Control experiments substituted an empty vector plasmid for the TARS construct. Following a 48 hour incubation, cells were lysed with 1% Triton X, 0.5% NP-40, 140 mM NaCl, 25 mM Tris-HCl pH 7.6, and 1 Complete Mini protease inhibitor tablet (Roche) per 10 ml. TARS was then "pulled-down" with streptavidin immobilized on magnetic beads (Invitrogen, Dynabeads MyOne Streptavidin) and unbound proteins were washed away with three exchanges of lysis buffer. The bound proteins were eluted from the beads through boiling and resolved on a reducing, SDS-PAGE gel. Major bands and their empty vector counterparts were detected using Silver-SNAP Stain Kit II (Pierce) and excised. Fragments were typically digested using the in gel procedure for Protease-MAX Surfactant (Promega, Madison, Wis.) according to the manufacturers specifications. Briefly, free cysteines were alkylated by incubation with 55 mM iodoacetamide:50 mM $NH_4HCO_3$ followed by trypsin digestion (2 ng/µl) in 0.01% ProteaseMAX surfactant:50 mM $NH_4HCO_3$. Peptides were analyzed by electospray ionization (ESI) liquid chromatography mass spectrometry (LC-MS). Samples were resolved over a fused-silica microcapillary MagicC18 LC column (12 cm×100 µm i.d.) using a 5-50% acetonitrile gradient in 0.1% formic acid. Spectra were obtained using collision-induced dissociation with an LTQ linear quadrupole ion trap-Orbitrap mass spectrometer (Thermo Electro, San Jose, Calif.) and analyzed using SEQUEST (Bioworks software package, version 3.3.1; Thermo Electron, San Jose, Calif.). Acquired TARS data were compared to empty vector equivalents in order to identify non-specific interactions.

Results for Example 4

Figure 14:
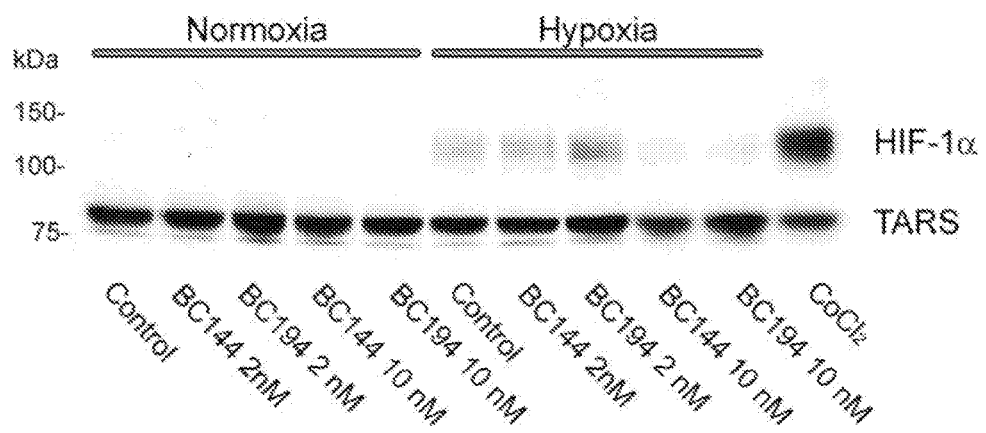
FIG. 14 shows a Western blot demonstrating that TARS inhibitors reduce HIF-1α stabilization in hypoxia. SKOV-3 cells were exposed to hypoxia (2% $O_2$) for 6 h in the presence of the indicated concentrations of the TARS inhibitors: borrelidin (BC144) or BC194. $CoCl_2$ was used as a positive control for HIF-1α stabilization. HIF-1α and TARS proteins were detected by Western blot.

An interaction between TARS and VHL may affect hypoxia signaling. VHL is the E3 ubiquitin ligase for Hypoxia inducible factor-1α (HIF-1α), thus if TARS interferes with VHL activity, it may influence the induction of HIF-1α by hypoxia. Shown in FIG. 14, the TARS inhibitors BC144 and BC194 diminished the levels of HIF-1α protein stabilization in SK-OV3 ovarian cancer cells responding to hypoxia. The effect was through stabilization as there was no change in HIF-1α transcription. Accordingly, it was hypothesized that the lowering of HIF-1α levels by BC194 occurs as a consequence of a TARS' interaction with VHL.

Figure 15:
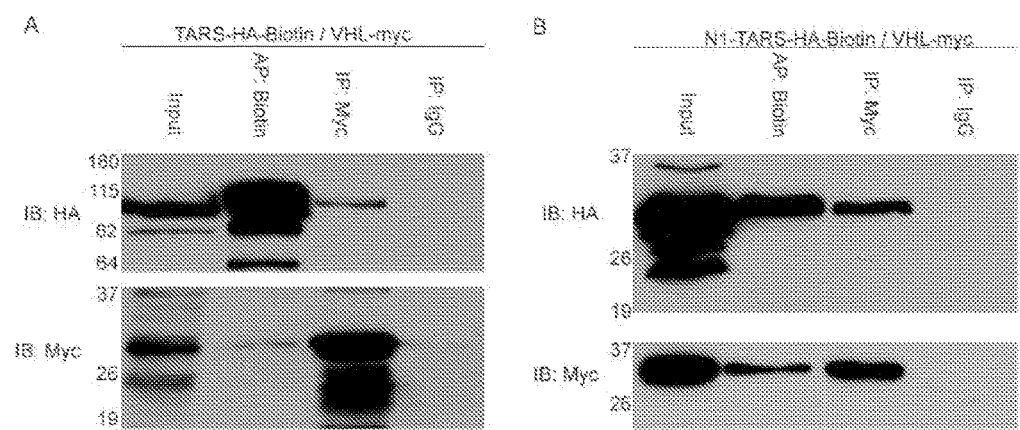
FIG. 15 provides evidence for an interaction between TARS and the von Hippel Lindau protein (VHL). Plasmids expressing biotinylatable TARS (TARS-HA-Biotin) and myc-tagged VHL (VHL-myc) were transfected into HEK293 cells, and then extracts were prepared. Biotin-TARS was precipitated using streptavidin-coupled beads. Myc-VHL was precipitated using anti-myc antibodies. Shown in FIG. 15A is an interaction between full-length TARS and VHL by co-immunoprecipitation. Top panels are blots probed with antibody against HA (anti-TARS), bottom panels are blots probed with antibody against myc (VHL) antibody. The various lanes indicate input lysates (Input), streptavidin affinity purified (AP:Biotin), anti-Myc immunoprecipitates (IP:Myc), naïve IgG immunoprecipitates IIP: IgG). Shown in FIG. 15B is the same experiment as FIG. 15A, only the N1 domain of TARS is used in place of the full length enzyme. See FIG. 16 for structural details.

A large-scale study examining protein-protein interactions in human cells featured the immunoprecipitation of flag tagged bait proteins, followed by the LC-ESI/MS analysis of interacting proteins. Using the Von Hippel Lindau tumor suppressor as bait, TARS was identified as a potential binding partner. This result was confirmed in two independent approaches. In the first of these experiments, HEK cells were transfected with expression plasmids for TARS-[hemagglutinin tag]-[biotinylation recognition] and VHL-[myc-tag]. The TARS construct possessed an appended peptide tail that served as recognition site for the E. coli biotin ligase, whose gene was also transfected into cells. As shown in FIG. 15A, when biotinylated TARS is precipitated incubation of the extracts with streptavidin beads, the VHL protein is co-precipitated. Conversely, immunoprecipitated VHL will also co-precipitate full-length TARS. The region of TARS that interacts with VHL was explored by a comparison of the structure of the VHL-ElonginB-ElonginC complex to TARS. ElonginB which is a component of the complex, can be readily superimposed with the N-terminal domain of TARS (106 residues aligned; 2.71 r.m.s.d.; p value=0.0019). To confirm the significance of this structural relationship, HEK cells were transfected with plasmids expressing the N-terminal domain of TARS-[hemagglutinin tag]-[biotinylation recognition] and VHL-[myc-tag], and then TARS N1 domain was precipitated with streptavidin beads. This analysis showed that the N1 domain precipitated VHL more efficiently than the full length TARS (FIG. 15B). Hence, the N1 domain is likely to be one of the major interaction domains with VHL.

In order to provide additional validation of the proposed VHL-TARS interaction, and perform the converse experiment of the original Ewing et al experiment (Ewing, Chu, et al. 2007), the proteins that associate with TARS in vivo were identified by precipitating biotinylated TARS, resolving all proteins by SDS polyacrylamide gel electrophoresis, and then subjecting isolated bands to mass spectrometry analysis. The resulting TARS binding partners that were identified are shown in FIG. 16. As a control, a parallel lane was run with proteins precipitated from HEK cells transfected with an "empty" plasmid that does not over produce TARS, or any other protein that can be biotinylated. All peptides that were common to both the TARS plus and control were subtracted from the final results. The "TARS plus" experiments were performed in the presence and absence of plasmids expressing VHL. These experiments identified a number of partners for TARS, including VHL, the glutamyl-prolyl tRNA synthetase (EPRS), poly[ADP-ribose] polymerase 1 (PARP), and elongation factor 1 alpha 1 (eEF1A1). Several other proteins were also detected as single peptides.

Example 5

Angiogenesis Related Secondary Functions of Human Threonyl-tRNA Synthetase

Materials and Methods for Example 5.

TARS Preparation and Nucleotide Assays—

Figure 17:
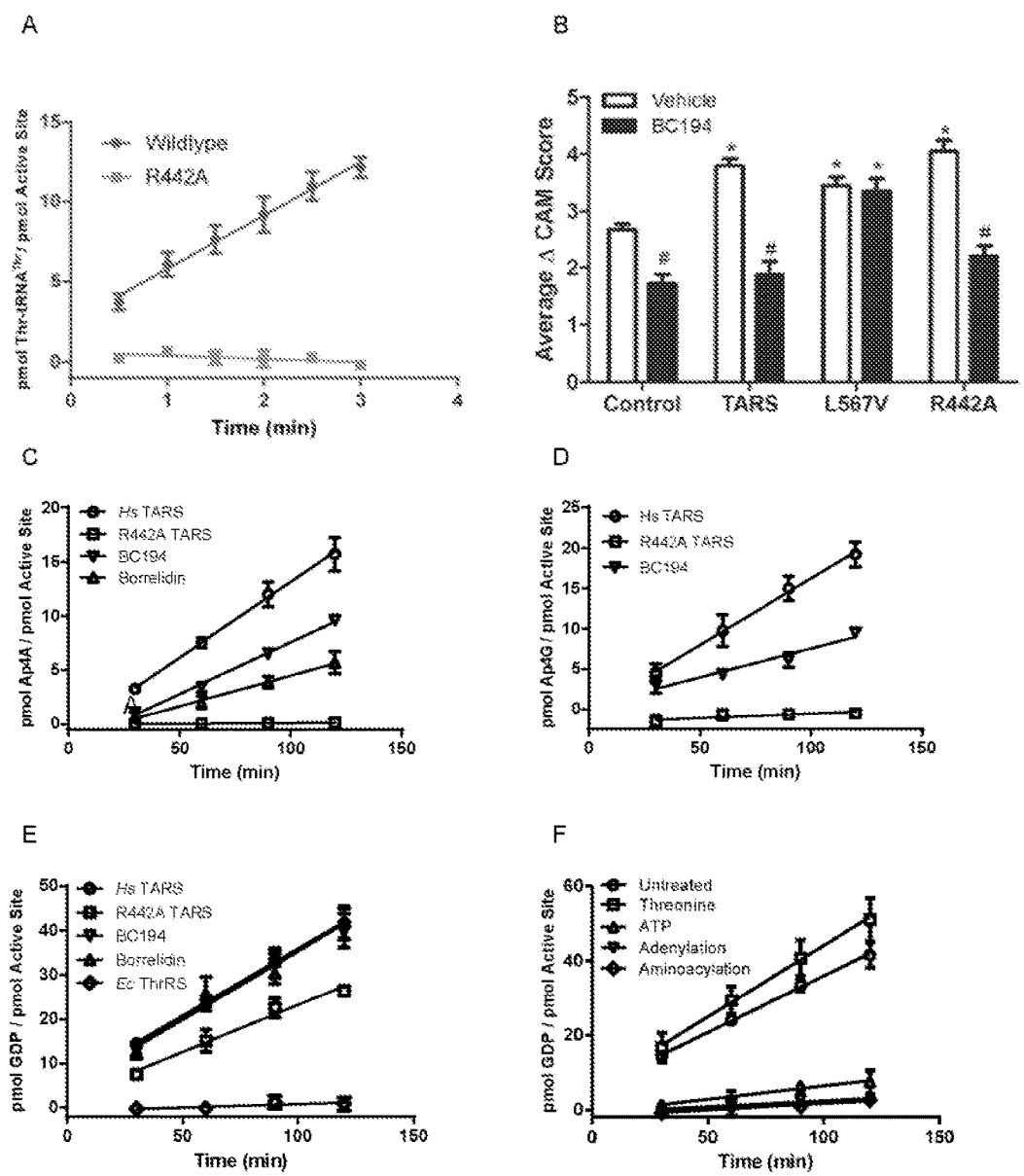
FIG. 17 provides graphs and histogram showing that human TARS does not require aminoacylation activity to stimulate angiogenesis activity, and is capable of catalyzing nucleotidase and nucleotide synthesis reactions distinct from aminoacylation. Wild type and R442A mutant TARS were produced as described in Materials and Methods, in Examples section. The R442A mutant substitution exchanges an essential catalytic arginine in the TARS active site for an alanine. The CAM assays were performed as described in Material and Methods in Examples section.

TARS purification and active site determination were performed as previously described (Williams, Mirando et al., 2013). TARS non-canonical catalytic activities were characterized using modifications from published methods (Guo, Chong et al. 2009). For Ap4A reactions 5 µM of wildtype TARS or R442A TARS were incubated for 10 minutes on ice with 2 mM threonine, and 10 µM BC194 or borrelidin as indicated in FIG. 17C. Reactions were initiated using 2 mM ATP with trace amounts of [α-$^{32}$P]-ATP as label. At specific time points aliquots were quenched in 3 volumes of 0.1% SDS, 400 mM sodium acetate and resolved on polyethyleneimine-cellulose plates by thin-layer chromatography (TLC) in 3 M $NH_4$ $(SO_4)_2$ and 2% EDTA. Radioactive counts were identified by phosphorimaging and products quantified as fractions of total ATP added. The quantitation of product was normalized to take into account the fact that each Ap4A molecule has two equivalents of radioactive phosphorus.

Ap4G and GTPase assays were performed as above with the following exceptions: Ap4G reactions always included 2 mM ATP and 2 mM threonine and 10 µM BC194 where indicated in FIG. 17D. For GTPase assays, ATP and threonine were not present in all reactions but were included in combination with, 10 µM tRNA$^{Thr}$, 10 µM BC194, and 10 µM borrelidin according to FIG. 17F. Adenylation conditions consisted of ATP and threonine and aminoacylation conditions further included tRNA$^{Thr}$. Reactions were initiated using 2 mM GTP with trace amounts of [α-$^{32}$P]-GTP. The components were resolved by TLC using the mobile phases 750 mM $KH_2PO_4$, pH 3.5 for GTPase data and 3 M $NH_4$ $(SO_4)_2$ and 2% EDTA for Ap4G. Unlike with Ap4A, Ap4G involves only the incorporation of one labeled nucleotide and does not require the 0.5 correction factor.

CAM Assays—

Fertilized chicken embryos were cultured ex-ova and, starting at developmental day 10, agents were applied daily to gelfoam sponges on the CAM. Images were recorded daily over 72 h and scored blindly according to a modified version Intensity Scoring as previously described (Ribatti, Nico et al. 2006). Additional details regarding methods are provided in the Methods and Materials section of Example 1.

Results for Example 5

An important scientific question is the extent to which the pro-angiogenic functions of TARS are directly linked to aminoacylation function. Alternatively, stimulation of angiogenesis might be linked to alternate catalytic functions, employing substrates and products that are distinct from those aminoacylation. To directly test whether aminoacylation is required for stimulation of angiogenesis, a mutant version of hTARS was produced in which an essential arginine in the active site (Arg442) was substituted with alanine. As shown in FIG. 17A, the resulting mutant protein displayed essentially no aminoacylation activity. Next, the chorioallantoic membrane (CAM) assay was used to investigate whether loss of aminoacylation was associated with loss of angiogenesis stimulating activity. As shown in FIG. 17B, R442A TARS demonstrated angiogenesis stimulating abilities that were virtually indistinguishable from wild type. Notably, the uninhibited version of R442A TARS had an average CAM score that was equal to that of wild type, and R442A displayed a similar level of inhibition of angiogenesis stimulus in the presence of BC194. On the basis of these experiments, it was concluded that aminoacylation function is not required for the stimulation of angiogenesis.

In light of the previous observation that aminoacylation activity is not required to stimulation of angiogenesis, the hypothesis that an alternative catalytic function might be involved was explored. One such alternative is the production of diadenosine tetraphosphate (Ap4A), which is produced by human lysyl-tRNA synthetase in immune cells that become activated by antigen. The Ap4A produced by LysRS binds to Hint, liberating the associated microphthalmia transcription factor (MITF) to execute a complicated program of gene expression (Lee, Nechushtan et al. 2004; Ofir-Birin, Fang et al. 2013). This confirms the role of Ap4A as an intracellular signaling molecule. There is also data to suggest that Ap4A can function as an extracellular signaling molecule (McLennan 2000) (Delicado, Miras-Portugal et al. 2006). Significantly, Ap4A is released extracellularly from platelets, and is capable interacting with the P2Y and P2× receptors. These interactions have the potential of modulating angiogenesis in endothelial cells (Chang, Yanachkov et al. 2010; Roedersheimer, Nijmeh et al. 2011).

As shown in FIG. 17C, significant production of Ap4A was observed for wildtype TARS (0.1391 Ap4A/active site/min) and *E. coli* ThrRS (0.5612 Ap4A/active site/min; data not shown). In contrast, no appreciable activity was observed for the aminoacylation-deficient, R442A TARS or in absence of threonine, suggesting that the adenylate intermediate is essential for dinucleotide formation. Treatment with BC194 and borrelidin resulted in a 31.0% and 59.4% decrease in activity respectively. This reduction in activity is not unsurprising as previous reports indicate that borrelidin compounds inhibit aminoacylation at the level of adenylate formation (Ruan, Bovee et al. 2005). However, the 10 µM concentration used for both compounds is in great excess of the calculated $K_i$ values (4.1 nM for BC194; see Williams, Mirando et al. 2013) and 4.6 nM for borrelidin, data not shown) suggesting that maximum inhibition still allows for reduced formation of the adenylate intermediate. A possible explanation for this modest drop in activity compared to the nearly complete inhibition of aminoacylation at similar concentrations is that borrelidin compounds block tRNA$^{Thr}$ binding as well; encouraging the small amount of adenylate that does form to be used in the synthesis of dinucleotide compounds. Similar results were observed (FIG. 17D) in studies of Ap4G: rates for wildtype TARS and *E. coli* ThrRS (data not shown) were comparable to Ap4A data (0.1639 and 0.5612 Ap4G/active site/min respectively). The reaction was not catalyzed by R442A TARS and required the presence of both ATP and threonine, suggesting that adenylate formation was still a requirement. Since threonine alone was not sufficient to form a significant dinucleotide product, Gp4G formation is unlikely. Once again, treatment with BC194 reduced the reaction rate by 57%. Given the similarities between the two processes, it is likely that Ap4A and Ap4G formation occurs at the same site in the enzyme; however, the exact residues involved remains to be determined.

Another reaction in which aminoacyl-tRNA synthetases can potentially modulate signaling is GTP hydrolysis. Recent published work indicates that LeuRS may contribute amino acid sensing properties to the Mammalian Target of Rapamycin complex (mTOR) by virtue of interactions with the Rag GTPase a mediator of amino acid signaling to mTORC1 (Bonfils, Jaquenoud et al. 2012; Han, Jeong et al. 2012). In contrast to the dinucleotide synthesis, TARS GTPase activity differs greatly in response to similar treatments. As shown in FIGS. 17E and 17F, a direct stimulation of GTP hydrolysis by TARS was observed in both the wildtype and R442A TARS (0.3033 and 0.2137 GDP/active site/min respectively) but not in *E. coli* ThrRS. Furthermore, there was no observable change upon treatment with either BC194 or borrelidin. Taken together, these data would suggest that TARS GTPase activity is specific to the human enzyme (relative to *E. coli*) and does not require the same catalytic residues as aminoacylation. Despite this apparent disconnect to aminoacylation, GTPase activity is responsive to the availability of canonical substrates. While threonine appears slightly stimulating (26% increase in activity) ATP, adenylation, and aminoacylation conditions decrease activity by 77%, 90%, and 89% respectively. Given that all of these conditions require ATP, it may be that the two nucleotides compete for the same site. However, there is not enough information to rule out an allosteric form of inhibition as well. Interestingly, the formation of Ap4G requires ATP to be present but maintains the same activity of Ap4A, suggesting that the use of GTP in the synthesis of dinucleotides is not similarly regulated.

Example 6

TARS is Overexpressed in Ovarian Cancer
Materials and Methods for Example 6
Ovarian Cancer Study Group—

The ovarian cancer studies were approved by the University of Vermont's institutional review board (CHRMS 01-026 and M12-004). The study group consisted of 58 patients diagnosed with epithelial ovarian cancer at Fletcher Allen Health Care/University of Vermont between 1999 and 2001. The control group consisted of 16 women who underwent oophorectomies for gynecologic reasons (other than ovarian cancer) and the final pathology demonstrated normal ovarian tissue. Serum and paraffin embedded samples from both the study and control group were obtained after an adequate portion of the samples were evaluated for pathologic diagnosis. Histological subtype was based according to the WHO criteria and grading of tumors. Formalin-fixed, paraffin embedded tissue samples from each patient were retrieved. Three serial sections (6 µm) from each specimen were cut and transferred to slides, then analyzed using immunohistochemistry to measure the expression of VEGF and TARS as previously described (Wong, Wellman et al. 2003). After deparaffinization and rehydration, slides were incubated at 97° C. for 15 min with DAKO target retrieval solution, containing 100 mM Tris base, pH 10.5 and 0.1% Triton X-100. Immunoperoxidase staining was performed using the mouse ImmunoCruz staining system (Santa Cruz Biotechnology, Santa Cruz, Calif.) according to the manufacturer's protocol. Antibodies were mouse monoclonal anti-VEGF (1:100, Santa Cruz Biotechnology) and mouse monoclonal anti-TARS (1:100, Clone 1A9 Abnova, Taipei City, Taiwan). Normal mouse IgG was used as a negative control. After immunoperoxidase staining, cells were lightly stained with Mayers' hematoxylin and eosin. Slides were dehydrated through xylenes then mounted with coverslips using Cytoseal 60 (Richard-Allan Scientific, Kalamazoo, Mich.). Images were obtained using an Olympus BX50 light microscope coupled to a CCD camera and Metamorph image capture software. Slides were scored for the expression of VEGF and TARS on a scale of 1-4 where 1=no staining and 4=intense staining TARS ELISA was performed on undiluted serum following the manufacturer's instructions (Cusabio Biotech). Statistical significance between groups was determined using Kruskal-Wallis test. Correlation between TARS and VEGF expression was evaluated using multiple regression correlation coefficient.
Results for Example 6

Figure 18:
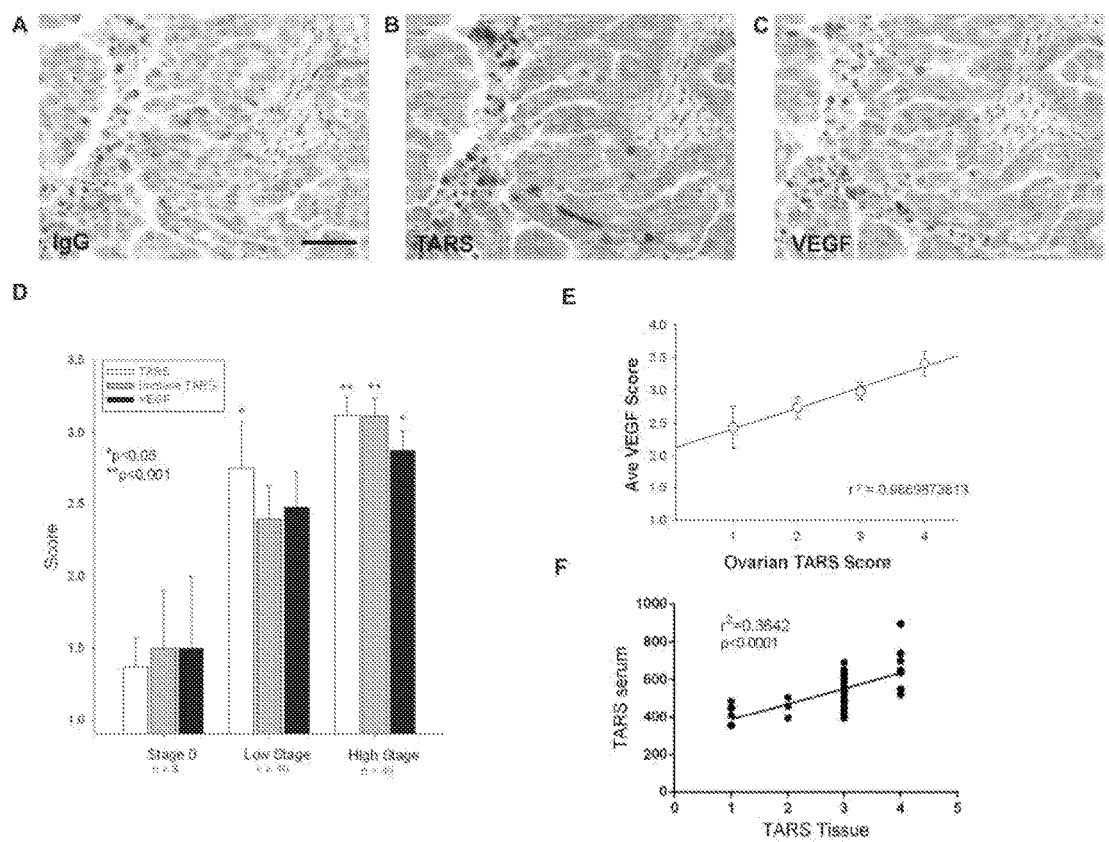
FIG. 18 provides photomicrograph images and graphs showing TARS expression by immunohistochemistry (IHC) is increased in human serous papilloma ovarian cancer and colocalizes with VEGF. Patient tumor samples were sectioned, and stained using anti-TARS (FIG. 18B) or anti-VEGF (FIG. 18C) antibodies. Control (FIG. 18A) for staining had no primary antibody (No Ab). Slides were lightly stained with hematoxylin and eosin for visualizing cell structures. Statistical analysis shows expression of TARS is significantly increased in ovarian cancer (FIG. 18D), and regression analysis correlates TARS in tumor tissue with levels of VEGF (FIG. 18E) and serum levels of TARS (FIG. 18F) as measured by ELISA.

It has previously been shown that VEGF is overexpressed in ovarian cancer and correlates with progression of disease (Wong, C. et al. (2003) *Gynecol Oncol* 91 (3), 513-517). To determine whether TARS is dysregulated in human ovarian cancer, immunohistochemical staining for TARS was performed on patient tumor sections and correlated with staining of VEGF and serum levels of TARS. In the samples analyzed, TARS staining colocalized with VEGF and was selectively overexpressed in the tumor cells (FIG. 18). In addition, TARS serum levels significantly correlated with TARS tissue levels, supporting further analysis of TARS as an indicator of ovarian cancer (FIG. 18). Scoring and statistical analyses of data from all of the patients is ongoing and additional patients will be recruited to determine if TARS levels correlate with stage of disease as well as patient outcome leading to Example 7.

Example 7

Identifying a Clinical Relationship Between Cancer and TARS Protein Level and Activity in Tissue and Serum Results of these experiments better define the newly discovered pathway whereby cells regulate angiogenesis through unconventional signaling by an aminoacyl tRNA synthetase. These experiments also determine the anti-angiogenic activity of TARS inhibitors, which suggest their development for and use as a therapeutic in ovarian and other angiogenesis-dependent cancers. Furthermore, these experiments determine if TARS secretion can be used as a means of detecting angiogenic ovarian cancer to assist in earlier diagnosis and improved treatment regimens for ovarian cancer patients.

Studies are performed that include measuring TARS expression in tumors and serum obtained from cancer patients, including but not limited to ovarian cancer patients, prostate cancer patients, etc. In the studies, angiogenesis markers such as PECAM are compared with control levels and the cancer's status, stage, and progression and the subject's prognosis is determined. Additional types of cancers tested are metastatic carcinoma of the cervix; sarcoma of the kidney; renal cell carcinoma; prostate cancer; androgen independent prostate cancer; Kaposi's sarcoma; colorectal cancer, hepatobilliary cancer, gastric cancer, epithelial ovarian cancer; lung cancer, and/or mesothelioma.

Experiments are performed and TARS activity and/or expression is measured in samples from one or more subjects that have or are suspected of being at risk of having additional diseases and conditions such as angiogenesis-associated disorder in which the level of TARS is increased as compared to a normal control level. A TARS level is determined to assess a cancer, a tumor, a hemangioma, a vascular overgrowth, a venous malformation, an arterial malformation, overweight, macular degeneration, an inflammatory disease, psoriasis, diabetes, or rheumatoid arthritis.

Additional studies are performed and TARS activity and/or expression is determined in samples from one or more subjects that have or are suspected of being at risk of having additional diseases and conditions such as angiogenesis-associated disorder in which the level of TARS is decreased as compared to a normal control level. A TARS level is determined for a tissue implant, an organ implant, ischemia, cardiac infarction, tissue trauma, cartilage to bone transformation, stroke, surgery, pregnancy, macular degeneration, and/or vascular occlusion.

The stage and prognosis for one or more of the diseases and conditions listed above elsewhere herein are assessed by determining the level of TARS in a sample and comparing the level to a level in a control sample.

REFERENCES

Additional References are Cited in Specification and Examples

Ahmed, S. A., R. M. Gogal, Jr., et al. (1994). "A new rapid and simple non-radioactive assay to monitor and determine the proliferation of lymphocytes: an alternative to [3H]thymidine incorporation assay." *J Immunol Methods* 170(2): 211-24.

Altundag, K., O. Altundag, et al. (2005). "CA125 Nadir values as a prognostic factor in epithelial ovarian cancer." *J Clin Oncol* 23(10): 2435-6; author reply 2436.

Arnaoutova, I. and H. K. Kleinman (2010). "In vitro angiogenesis: endothelial cell tube formation on gelled basement membrane extract." *Nat Protoc* 5(4): 628-35.

Bonfils, G., M. Jaquenoud, et al. (2012). "Leucyl-tRNA synthetase controls TORC1 via the EGO complex." *Mol Cell* 46(1): 105-10.

Cassavaugh, J. M., S. A. Hale, et al. (2011). "Negative regulation of HIF-1alpha by an FBW7-mediated degradation pathway during hypoxia." *J Cell Biochem* 112(12): 3882-90.

Chang, H., I. B. Yanachkov, et al. (2010). "Agonist and antagonist effects of diadenosine tetraphosphate, a platelet dense granule constituent, on platelet P2Y1, P2Y12 and P2X1 receptors." *Thromb Res* 125(2): 159-65.

Conant, J L, Penz, Z, Evans M F, Naud S, Cooper K (2011) Sarcomatoid renal cell carcinoma is an examples of epithelial-mesenchymal transition. *J. Clin. Path.* 64(12); 1088-1092.

Delicado, E. G., M. T. Miras-Portugal, et al. (2006). "Dinucleoside polyphosphates and their interaction with other nucleotide signaling pathways." *Pflugers Arch* 452 (5): 563-72.

Ewing, R. M., P. Chu, et al. (2007). "Large-scale mapping of human protein-protein interactions by mass spectrometry." *Mol Syst Biol* 3: 89.

Francklyn, C. S., E. A. First, et al. (2008). "Methods for kinetic and thermodynamic analysis of aminoacyl-tRNA synthetases." *Methods* 44(2): 100-18.

Greenberg, Y., M. King, et al. (2008). "The novel fragment of tyrosyl tRNA synthetase, mini-TyrRS, is secreted to induce an angiogenic response in endothelial cells." *FASEB J* 22(5): 1597-605.

Guo, R. T., Y. E. Chong, et al. (2009). "Crystal structures and biochemical analyses suggest a unique mechanism and role for human glycyl-tRNA synthetase in Ap4A homeostasis." *J Biol Chem* 284(42): 28968-76.

Han, J. M., S. J. Jeong, et al. (2012). "Leucyl-tRNA synthetase is an intracellular leucine sensor for the mTORC1-signaling pathway." *Cell* 149(2): 410-24.

Lee, Y. N., H. Nechushtan, et al. (2004). "The function of lysyl-tRNA synthetase and Ap4A as signaling regulators of MITF activity in FcepsilonRl-activated mast cells." *Immunity* 20(2): 145-51.

Longair, M. H., D. A. Baker, et al. (2011). "Simple Neurite Tracer: open source software for reconstruction, visualization and analysis of neuronal processes." *Bioinformatics* 27(17): 2453-4.

Lounsbury, K. M., A. L. Beddow, et al. (1994). "A family of proteins that stabilize the Ran/TC4 GTPase in its GTP-bound conformation." *J Biol Chem* 269(15): 11285-90.

McLennan, A. G. (2000). "Dinucleoside polyphosphates-friend or foe?" *Pharmacol Ther* 87(2-3): 73-89.

Mor, G., I. Visintin, et al. (2005). "Serum protein markers for early detection of ovarian cancer." *Proc Natl Acad Sci USA* 102(21): 7677-82.

Ofir-Birin, Y., P. Fang, et al. (2013). "Structural Switch of Lysyl-tRNA Synthetase between Translation and Transcription." *Mol Cell* 49(1): 30-42.

Ribatti, D., B. Nico, et al. (2006). "The gelatin sponge-chorioallantoic membrane assay." *Nat Protoc* 1(1): 85-91.

Roedersheimer, M., H. Nijmeh, et al. (2011). "Complementary effects of extracellular nucleotides and platelet-derived extracts on angiogenesis of vasa vasorum endothelial cells in vitro and subcutaneous Matrigel plugs in vivo." *Vasc Cell* 3(1): 4.

Ruan, B., M. L. Bovee, et al. (2005). "A unique hydrophobic cluster near the active site contributes to differences in borrelidin inhibition among threonyl-tRNA synthetases." *J Biol Chem* 280(1): 571-7.

Strausberg, R. L. (2001). "The Cancer Genome Anatomy Project: new resources for reading the molecular signatures of cancer." *J Pathol* 195(1): 31-40.

Svensson, K. J., P. Kucharzewska, et al. (2011). "Hypoxia triggers a proangiogenic pathway involving cancer cell microvesicles and PAR-2-mediated heparin-binding EGF signaling in endothelial cells." *Proc Natl Acad Sci USA* 108(32): 13147-52.

Tomlins, S. A., R. Mehra, et al. (2007). "Integrative molecular concept modeling of prostate cancer progression." *Nat Genet* 39(1): 41-51.

Uhlen, M., P. Oksvold, et al. (2010). "Towards a knowledge-based Human Protein Atlas." *Nat Biotechnol* 28(12): 1248-50.

Wakasugi, K. and P. Schimmel (1999). "Two distinct cytokines released from a human aminoacyl-tRNA synthetase." *Science* 284(5411): 147-51.

Williams, T. F., A. C. Mirando, et al. (2013). "Secreted Threonyl-tRNA synthetase stimulates endothelial cell migration and angiogenesis." *Scientific Reports* 3. 1317; DOI:10.1038/srep01317.

Wilkinson, B., M. A. Gregory, et al. (2006). "Separation of anti-angiogenic and cytotoxic activities of borrelidin by modification at the C17 side chain." *Bioorg Med Chem Left* 16(22): 5814-7.

Wong, C., T. L. Wellman, et al. (2003). "VEGF and HIF-1alpha expression are increased in advanced stages of epithelial ovarian cancer." *Gynecol Oncol* 91(3): 513-7.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method of increasing angiogenesis in at least one cell, the method comprising, contacting a plurality of cells with a pharmaceutical composition comprising an effective amount of a TARS-activity-enhancing compound to increase angiogenesis at least one cell of the plurality of cells, wherein the TARS-activity-enhancing compound comprises:
   (a) a threonyl-tRNA synthetase (TARS) nucleic acid molecule having the sequence of: (i) SEQ ID NO: 1, (ii) a modified SEQ ID NO: 1 that has at least 99% sequence identity to SEQ ID NO: 1, wherein each of (i) and (ii) encodes a TARS-activity-enhancing polypeptide; or
   (b) a TARS polypeptide having the sequence of (iv) SEQ ID NO: 2, (v) a modified SEQ ID NO: 2 that has at least 99% sequence identity to SEQ ID NO: 2, wherein each of (iv) and (v), is a TARS activity enhancing polypeptide.

2. The method of claim 1, wherein the plurality of cells is in a subject and contacting the cells comprises administering the TARS-activity-enhancing compound to the subject.

3. The method of claim 2, wherein the subject has or is at risk of having an angiogenesis-associated disease or condition.

4. The method of claim 1, further comprising contacting the plurality of cells with one or more additional angiogenesis-enhancing compounds.

5. The method of claim 4, wherein contacting the plurality of cells with the TARS-activity-enhancing compound and one or more of the additional angiogenesis-enhancing compounds results in a synergistic increase in angiogenesis in the plurality of cells.

6. The method of claim 2, wherein the subject is a human.

7. The method of claim 1, wherein the plurality of cells comprises one or more pre-vascular cells, angioblasts, endothelial cells, vascular cells, immune system cells.

8. The method of claim 1, wherein the threonyl-tRNA synthetase (TARS) activity-enhancing compound molecule, fragment, or variant thereof, is administered after diagnosis of an angiogenesis-associated disease or condition.

9. The pharmaceutical composition for increasing angiogenesis comprising a TARS-activity-enhancing compound and a pharmaceutically acceptable carrier wherein the TARS-activity-enhancing compound comprises: (i) SEQ ID NO: 1, (ii) a modified SEQ ID NO: 1 that has at least 99% sequence identity to SEQ ID NO: 1 (iii) SEQ ID NO:2, or (iv) a modified SEQ ID NO: 2 that has at least 99% sequence identity to SEQ ID NO: 2.

10. The pharmaceutical composition of claim 9, further comprising a detectable label and, optionally, the detectable label comprises a biotin molecule.

11. The pharmaceutical composition of claim 9 wherein the TARS-activity-enhancing compound comprises a threonyl-tRNA synthetase (TARS) polypeptide that has an amino acid sequence set forth as SEQ ID NO:2 that includes a L567V substitution, or a nucleic acid that encodes SEQ ID NO: 2 that includes an L567V substitution.

12. The pharmaceutical composition of claim 9, wherein the TARS-activity-enhancing compound comprises a threonyl-tRNA synthetase (TARS) polypeptide that has an amino acid sequence set forth as SEQ ID NO:2 that includes an R442A substitution, or a nucleic acid encoding SEQ ID NO: 2 that includes an R442A substitution.

13. The pharmaceutical composition of claim 9, comprising a TARS-activity-enhancing compound and a pharmaceutically acceptable carrier, wherein the TARS-activity-enhancing compound comprises (i) a modified SEQ ID NO: 1 or (ii) a modified SEQ ID NO: 2, wherein the modification of SEQ ID NO: 1 and SEQ ID NO: 2 consist of conservative substitutions, deletions, or additions of nucleic acids or amino acids, respectively.

14. The pharmaceutical composition of claim 9, further comprising one or more additional angiogenesis-enhancing compounds.

15. The pharmaceutical composition of claim 9, wherein the TARS-activity-enhancing compound comprises a nucleic acid molecule having the sequence set forth as SEQ ID NO: 1 or a polypeptide having the sequence set forth as SEQ ID NO: 2.

16. The pharmaceutical composition of claim 13, further comprising a detectable label, and, optionally, the detectable label comprises a biotin molecule.

17. The pharmaceutical composition of claim 13, further comprising one or more additional angiogenesis-enhancing compounds.

* * * * *